(12) United States Patent
Yu et al.

(10) Patent No.: US 11,344,261 B2
(45) Date of Patent: May 31, 2022

(54) SYSTEMS, DEVICES, AND METHODS FOR FLUID MONITORING

(71) Applicant: GastroKlenz Inc., San Francisco, CA (US)

(72) Inventors: Eric Hsiang Yu, San Francisco, CA (US); Aly R. Elbadry, San Francisco, CA (US); Carlos Rovira Borras, San Francisco, CA (US); Daniel Elliott Francis, Mountain View, CA (US)

(73) Assignee: GastroKlenz Inc., San Francisco, CA (US)

( * ) Notice: Subject to any disclaimer, the term of this patent is extended or adjusted under 35 U.S.C. 154(b) by 0 days.

(21) Appl. No.: 17/177,047

(22) Filed: Feb. 16, 2021

(65) Prior Publication Data

US 2021/0186434 A1  Jun. 24, 2021

Related U.S. Application Data

(63) Continuation of application No. 16/914,074, filed on Jun. 26, 2020, now Pat. No. 10,925,549.

(Continued)

(51) Int. Cl.
*A61B 5/00* (2006.01)
*A61M 1/36* (2006.01)
(Continued)

(52) U.S. Cl.
CPC .......... *A61B 5/7275* (2013.01); *A61B 5/0022* (2013.01); *A61B 5/0059* (2013.01); *A61B 5/1455* (2013.01); *A61B 5/4875* (2013.01); *A61B 5/6866* (2013.01); *A61M 1/3609* (2014.02); *A61B 2560/04* (2013.01);
(Continued)

(58) Field of Classification Search
CPC ........ A61M 1/84; A61M 1/28; A61M 1/1609; A61M 1/1619
See application file for complete search history.

(56) References Cited

U.S. PATENT DOCUMENTS 4,243,883 A * 1/1981 Schwarzmann ....... G01N 21/85
250/343
4,725,148 A 2/1988 Endo et al.
(Continued)

FOREIGN PATENT DOCUMENTS

CN      203263900 U   11/2013
WO  WO 2010/056740 A1   5/2010
(Continued)

OTHER PUBLICATIONS

International Search Report and Written Opinion for PCT/US2018/065853 dated May 24, 2019, 23 pages.
(Continued)

*Primary Examiner* — Leslie R Deak
(74) *Attorney, Agent, or Firm* — Cooley LLP

(57) ABSTRACT

Devices, systems, and methods herein relate to predicting infection of a patient. These systems and methods may comprise illuminating a patient fluid in a fluid conduit from a plurality of illumination directions, measuring an optical characteristic of the illuminated patient fluid using one or more sensors, and predicting an infection state of the patient based at least in part on the measured optical characteristic.

27 Claims, 60 Drawing Sheets

Related U.S. Application Data

(60) Provisional application No. 62/867,157, filed on Jun. 26, 2019.

(51) Int. Cl.
   *A61M 1/00*    (2006.01)
   *A61B 5/1455*  (2006.01)

(52) U.S. Cl.
   CPC ............ *A61B 2562/16* (2013.01); *A61M 1/84* (2021.05); *A61M 2205/3306* (2013.01)

(56) References Cited

U.S. PATENT DOCUMENTS

| | | | |
|---|---|---|---|
| 4,745,279 A * | 5/1988 | Karkar | G01N 21/05 250/343 |
| 5,601,080 A | 2/1997 | Oppenheimer | |
| 6,228,047 B1 | 5/2001 | Dadson | |
| D476,730 S | 7/2003 | Q'Mahony et al. | |
| 6,758,835 B2 | 7/2004 | Close et al. | |
| 6,913,590 B2 | 6/2005 | Sorenson et al. | |
| 7,033,539 B2 | 4/2006 | Krensky et al. | |
| 7,420,658 B2 | 9/2008 | Petterson et al. | |
| 7,659,980 B1 | 2/2010 | Mitchell et al. | |
| 7,998,115 B2 | 8/2011 | Bedingfield | |
| 8,033,157 B2 | 10/2011 | Yardimci et al. | |
| 8,211,048 B2 | 7/2012 | Szamosfalvi et al. | |
| 8,216,156 B2 | 7/2012 | Dalebout et al. | |
| 8,239,010 B2 | 8/2012 | Banet et al. | |
| 8,285,487 B2 | 10/2012 | Bergstrom et al. | |
| 8,348,844 B2 | 1/2013 | Kunjan et al. | |
| 8,440,140 B2 | 5/2013 | Nagai et al. | |
| D694,396 S | 11/2013 | Belt et al. | |
| 8,628,724 B2 | 1/2014 | Kuenstner | |
| 8,708,950 B2 | 4/2014 | Scarpaci et al. | |
| 8,728,023 B2 | 5/2014 | Landherr et al. | |
| 8,747,333 B2 | 6/2014 | Burkholz | |
| 8,777,891 B2 | 7/2014 | Landherr et al. | |
| 8,801,652 B2 | 8/2014 | Landherr et al. | |
| 8,870,769 B2 | 10/2014 | Deshpande | |
| 8,886,273 B2 | 11/2014 | Li et al. | |
| 8,924,161 B2 | 12/2014 | Moerman | |
| 9,125,979 B2 | 9/2015 | Behzadi et al. | |
| 9,215,985 B2 | 12/2015 | Gross et al. | |
| D753,313 S | 4/2016 | Kim et al. | |
| 9,381,289 B2 | 7/2016 | Hedmann et al. | |
| 9,603,622 B2 | 3/2017 | Kamen et al. | |
| 9,724,458 B2 | 8/2017 | Grant et al. | |
| 9,764,074 B1 | 9/2017 | Childers et al. | |
| D801,519 S | 10/2017 | Sabin et al. | |
| D803,387 S | 11/2017 | Bodwell et al. | |
| 9,861,733 B2 | 1/2018 | Burbank et al. | |
| 9,894,894 B2 | 2/2018 | Hassanein et al. | |
| 9,962,524 B2 | 5/2018 | Andino | |
| 9,968,725 B2 | 5/2018 | Fulkerson et al. | |
| 9,968,742 B2 | 5/2018 | Van Antwerp et al. | |
| 10,032,270 B2 | 7/2018 | Turner | |
| 10,078,438 B2 | 9/2018 | Wang et al. | |
| 10,155,081 B2 | 12/2018 | Chen et al. | |
| D850,625 S | 6/2019 | Schmid | |
| 10,332,482 B2 | 6/2019 | Yik et al. | |
| D868,957 S | 12/2019 | Chase et al. | |
| 10,925,549 B2 | 2/2021 | Yu et al. | |
| 2003/0142291 A1 | 7/2003 | Padmanabhan et al. | |
| 2005/0256447 A1 | 11/2005 | Richardson et al. | |
| 2009/0149776 A1 | 6/2009 | Adams | |
| 2011/0196304 A1 | 8/2011 | Kramer | |
| 2014/0329265 A1 | 11/2014 | Wanders et al. | |
| 2015/0005699 A1 | 1/2015 | Burbank et al. | |
| 2015/0254490 A1 | 9/2015 | Cohen et al. | |
| 2016/0139114 A1 | 5/2016 | Bollmann et al. | |
| 2016/0216150 A1 | 7/2016 | Groeber et al. | |
| 2016/0320228 A1 | 11/2016 | Hudson | |
| 2016/0370287 A1 | 12/2016 | Barnes et al. | |
| 2017/0045455 A1 | 2/2017 | Robertson et al. | |
| 2017/0128653 A1 | 5/2017 | Yuds et al. | |
| 2017/0181678 A1 | 6/2017 | Newberry | |
| 2017/0216521 A1 | 8/2017 | Kolko et al. | |
| 2017/0266031 A1 | 9/2017 | Sanchez et al. | |
| 2017/0281846 A1 | 10/2017 | Manda et al. | |
| 2018/0028794 A1 | 2/2018 | Browd et al. | |
| 2018/0043075 A1 | 2/2018 | Gerber et al. | |
| 2018/0043078 A1 | 2/2018 | Gerber et al. | |
| 2018/0043080 A1 | 2/2018 | Gerber et al. | |
| 2018/0070841 A1 | 3/2018 | Honore et al. | |
| 2018/0073991 A1 | 3/2018 | Lura et al. | |
| 2018/0193546 A1 | 6/2018 | Gerber et al. | |
| 2018/0353671 A1 | 12/2018 | Tessendorf | |
| 2019/0228526 A1 | 7/2019 | Wuepper et al. | |
| 2019/0358387 A1 * | 11/2019 | Elbadry | A61M 1/361 |
| 2020/0405243 A1 | 12/2020 | Yu et al. | |
| 2021/0186433 A1 | 6/2021 | Yu et al. | |
| 2021/0215666 A1 * | 7/2021 | Kotanko | A61M 1/28 |

FOREIGN PATENT DOCUMENTS

| | | | |
|---|---|---|---|
| WO | WO 2014/163815 A1 | 10/2014 | |
| WO | WO 2015/012990 A1 | 1/2015 | |
| WO | WO 2015/164620 A1 | 10/2015 | |
| WO | WO 2016/046634 A1 | 3/2016 | |
| WO | WO 2016/205744 A1 | 12/2016 | |
| WO | WO 2017/092871 A1 | 6/2017 | |
| WO | WO 2017/132132 A1 | 8/2017 | |
| WO | WO 2018/007013 A2 | 1/2018 | |
| WO | WO 2018/142406 A1 | 8/2018 | |
| WO | WO 2019/118929 A1 | 6/2019 | |

OTHER PUBLICATIONS

International Search Report and Written Opinion for PCT/US2020/039986 dated Nov. 13, 2020, 19 pages.

* cited by examiner

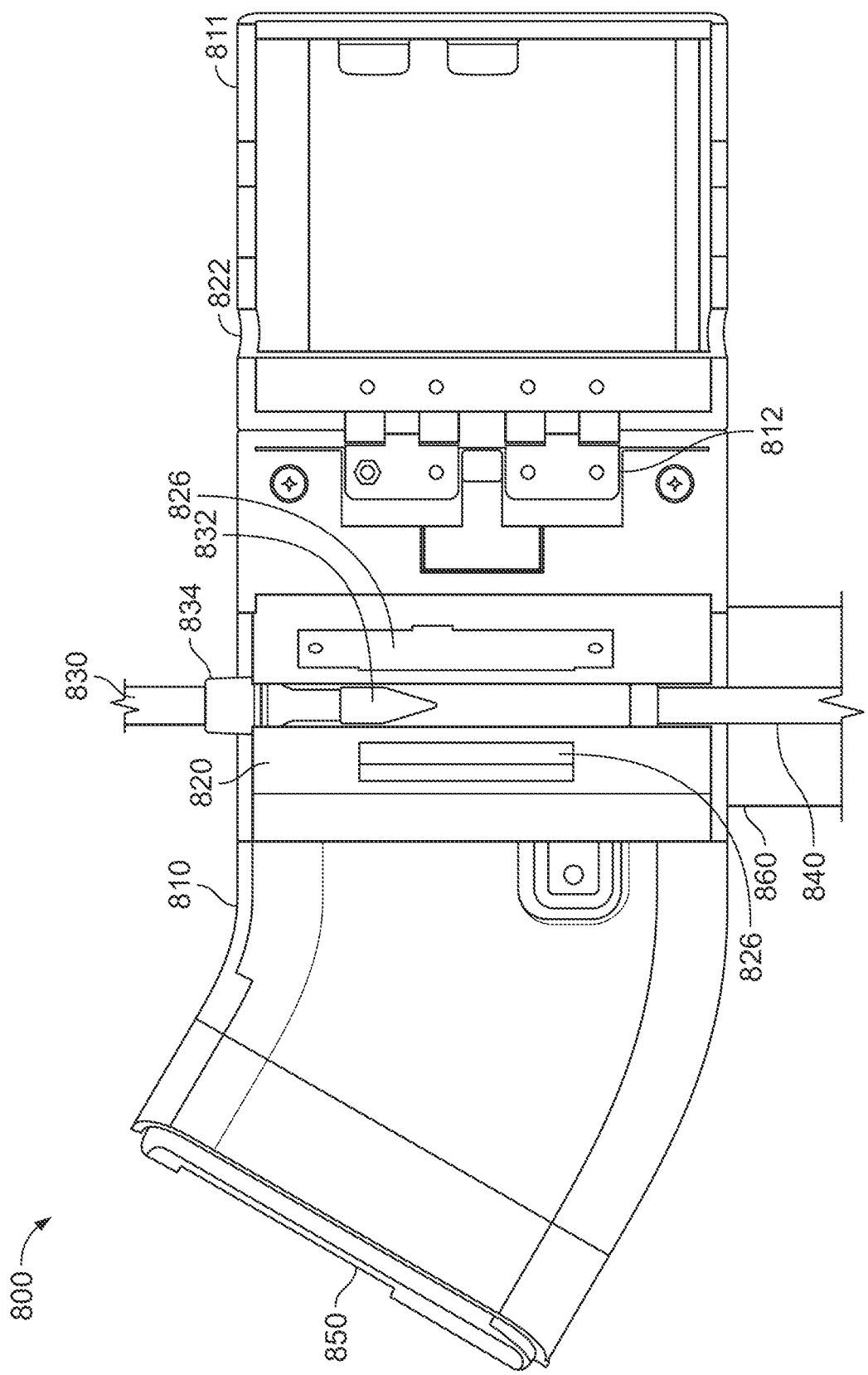

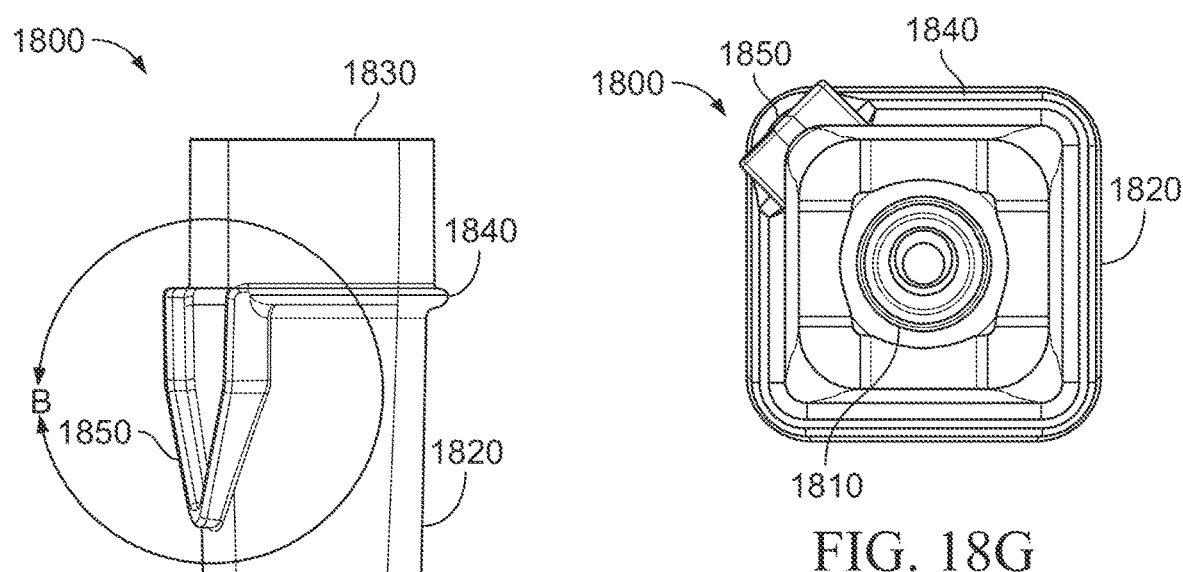
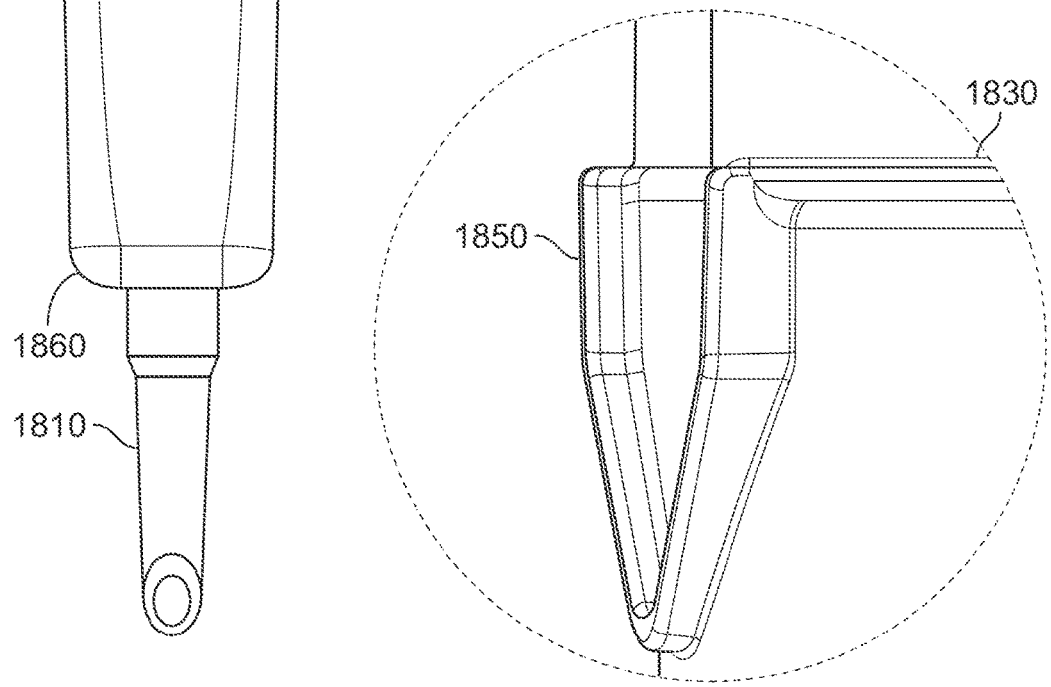
FIG. 18H
FIG. 18I

US 11,344,261 B2

SYSTEMS, DEVICES, AND METHODS FOR FLUID MONITORING

CROSS-REFERENCE TO RELATED APPLICATIONS

This application is a continuation of U.S. patent application Ser. No. 16/914,074, filed on Jun. 26, 2020, which claims priority to U.S. Provisional Application Ser. No. 62/867,157, filed on Jun. 26, 2019, the content of each of which is hereby incorporated by reference in its entirety.

FIELD

Devices, systems, and methods herein relate to fluid monitoring that may be used in diagnostic and/or therapeutic applications, including but not limited to infection prediction.

BACKGROUND

Several chronic diseases rely on patient self-administration or home caretaker administration of treatment in outpatient settings, including infusion into and/or drainage of fluids from the body via catheters or tubes. Some patients visit dialysis clinics on a weekly or monthly basis to perform a visual inspection for infections, to review patient data (e.g., manual records, night cycler data) for patient compliance, and to monitor treatment efficacy via blood draws. However, patients typically self-diagnose based on apparent signs of infection and are relied upon to timely report possible complications to a health care professional. Therefore, additional devices, systems, and methods for monitoring patient complications such as infection origination may be desirable.

SUMMARY

Described here are patient monitoring systems and devices and methods for detecting infection of a patient. These systems and methods may, for example, monitor patient fluid and analyze characteristics of the patient fluid to generate patient data that may be used to predict an infection state that may be presented to the patient and/or health care professional. This may, for example, allow the health care professional to prescribe a treatment plan at the onset of infection in order to quickly resolve the infection and reduce the need for costly hospitalization. Furthermore, the patient's response to treatment (e.g., an antibiotic regimen) may be monitored remotely over time and allow the treatment plan to be updated in real-time. The systems and devices described here are configured to retrofit a variety of existing dialysis catheters and dialysate infusion systems, including continuous cycling peritoneal dialysis (CCPD) and continuous ambulatory peritoneal dialysis (CAPD) systems.

Generally, methods of predicting infection of a patient may include the steps of illuminating a patient fluid in a fluid conduit from a plurality of illumination directions. An optical characteristic of the illuminated patient fluid may be measured using one or more sensors. An infection state of the patient may be predicted based at least in part on the measured optical characteristic.

In some variations, the plurality of illumination directions may comprise a first illumination direction and a second illumination direction orthogonal to the first illumination direction. In some of these variations, the predicted infection state of the patient may be based at least in part on one or more 90-degree scatter angle light intensity measurements from the one or more sensors. In some of these variations, the predicted infection state of the patient may further be based at least in part on one or more 180-degree attenuation light intensity measurements from the one or more sensors.

In some variations, the plurality of illumination directions may comprise a first illumination direction and a second illumination direction 180 degrees offset from the first illumination direction.

In some variations, illuminating the patient fluid may comprise illuminating the patient fluid at a first wavelength from a first illumination direction and at the first wavelength from a second illumination direction. The first and second illumination directions may extend along a first plane. In some variations, illuminating the patient fluid may comprise illuminating the patient fluid along at least the first plane and along a second plane substantially parallel to the first plane.

In some variations, the plurality of wavelengths may comprise a first wavelength between about 800 nm and about 900 nm. In some of these variations, illuminating the patient fluid may comprise illuminating the patient fluid sequentially at a plurality of wavelengths including the first wavelength. In some of these variations, the plurality of wavelengths may comprise a second wavelength between about 400 nm and about 450 nm, and a third wavelength between about 500 nm and about 550 nm. In some of these variations, illuminating the patient fluid may comprise sequentially illuminating the patient fluid at the third wavelength, the first wavelength, and then the second wavelength. In some of these variations, the plurality of wavelengths may comprise a fourth wavelength between about 230 nm and about 290 nm.

In some variations, the optical characteristic may comprise one or more of optical scatter and attenuation detection angle. In some variations, predicting the infection state may comprise generating an infection score and/or an infection probability. In some of these variations, estimating turbidity of the patient fluid may be based at least in part on the measured optical characteristic. The infection score may be based at least in part on the estimated turbidity. In some of these variations, predicting the infection state may comprise predicting infection in response to the infection score exceeding a predetermined threshold during each of one or more successive measurement time periods. In some of these variations, predicting the infection state may comprise predicting infection in response to the infection score increasing from a patient baseline over time. In some of these variations, predicting the infection state may comprise predicting infection based on a rate of change of the infection score over time.

In some variations, predicting the infection state may comprise predicting infection in response to any one or more of the following: the infection score exceeding a predetermined threshold during each of one or more successive measurement time periods, the infection score increasing from a patient baseline over time, and the infection score having an increasing rate of change over time. In some variations, predicting the infection state may comprise predicting a probability of infection.

In some variations, the fluid conduit may be coupled to a peritoneal dialysis device fluid path. In some variations, the fluid conduit may be coupled to a peritoneal dialysis device tubing set. In some variations, the fluid conduit may be coupled to an inlet of the peritoneal dialysis device tubing set. In some variations, the fluid conduit may be coupled to an outlet of the peritoneal dialysis device tubing set. In some variations, the fluid conduit may be coupled to a drain line of a peritoneal dialysis cycler tubing set. In some variations, the fluid conduit may be coupled to a drain line extension configured to couple to a peritoneal dialysis cycler tubing set drain line. In some variations, the fluid conduit may be coupled to a patient line of a peritoneal dialysis cycler tubing set. In some variations, the fluid conduit may be coupled to a peritoneal dialysis device tubing set.

In some variations, a fluid flow rate in the fluid conduit may be estimated based at least in part on the measured optical characteristic. Illuminating the patient fluid may comprise activating illumination based on the estimated fluid flow rate. In some of these variations, determining a fluid flow state may comprise detecting at least one of an ON state and an OFF state based on the estimated fluid flow rate. Illuminating the patient fluid may comprise activating illumination in response to detecting the ON state and ceasing illumination in response to detecting the OFF state.

In some variations, identifying a false positive fluid flow state may be based on the estimated fluid flow rate. In some variations, identifying the false positive fluid flow state may comprise detecting a predetermined number of pulses during less than each of one or more successive measurement time periods. In some variations, detecting the ON state may comprise detecting a predetermined number of pulses during each of one or more successive measurement time periods. In some variations, one or more successive measurement time periods may be separated by a predetermined delay time period. In some variations, estimating the fluid flow rate may be based at least in part on applying one or more of a low pass filter and a high pass filter to the measured optical characteristic. In some variations, initiating illuminating the patient fluid and measuring the optical characteristic may be based on a user input.

In some variations, detecting a bubble in the fluid conduit may be based at least in part on the optical measurement. In some variations, an indication of the predicted infection state may be provided to a user. In some variations, a particle concentration of the patient fluid may be predicted based at least in part on the measured optical characteristic. In some variations, bleeding of the patient may be predicted based at least in part on the measured optical characteristic. In some variations, an immune response of the patient may be predicted based at least in part on the measured optical characteristic. In some variations, predicting infection onset may be predicted for ascites drainage patients based at least in part on the measured optical characteristic. In some variations, a fibrin content of the patient fluid may be predicted based at least in part on the measured optical characteristic.

Also described here are vessels for use in a fluid conduit. The vessel may comprise an inlet portion, an outlet portion, and a generally optically transparent measurement portion between the inlet portion and the outlet portion. The measurement portion may comprise at least two substantially planar surfaces and a depth alignment feature.

In some variations, the measurement portion may comprise an internal volume configured to receive fluid. The internal volume may comprise radiused corners. In some of these variations, the at least two substantially planar surfaces may comprise a first planar surface generally orthogonal to a second planar surface. In some of these variations, the at least two substantially planar surfaces may comprise a first planar surface opposite to a second planar surface. In some of these variations, the measurement portion may comprise a generally square cross-section.

In some variations, at least a portion of the measurement portion may be tapered. In some variations, the measurement portion may comprise one or more of copolyester, acrylonitrile butadiene styrene, polycarbonate, acrylic, cyclic olefin copolymer, cyclic olefin polymer, polyester, polystyrene, ultem, polyethylene glycol-coated silicone, zwitterionic coated polyurethane, polyethylene oxide-coated polyvinyl chloride, and polyamphiphilic silicone.

In some variations, an opaque connector may be coupleable to the inlet portion or the outlet portion. In some of these variations, at least one of the inlet portion and the outlet portion may be coupleable to the fluid conduit. In some of these variations, one or more of a vent cap, clamp, and connector may be coupled to the fluid conduit. In some variations, the vessel may be coupled to a peritoneal dialysis drain set extension tubing.

In some variations, the vessel may be coupled to a peritoneal dialysis cycler tubing cassette. In some variations, the vessel may be coupled to an inlet of a peritoneal dialysis cycler tubing cassette. In some variations, the vessel may be coupled to a peritoneal dialysis drain bag connector. In some variations, the vessel may be coupled to a proximal end of a peritoneal dialysis drain bag connector. In some variations, the vessel may be coupled to a urinary catheter or Foley catheter drain bag. In some variations, the vessel may be coupled to a central venous drain line. In some variations, the vessel may be coupled to a hemodialysis blood circulation tube set. In some variations, the vessel may be coupled to an in-dwelling catheter. In some variations, the vessel may be coupled to a proximal end of the in-dwelling catheter Also described here are patient monitoring devices comprising a housing. The housing may comprise a holder configured to releasably receive a portion of a fluid conduit. At least one illumination source may be configured to illuminate the received portion of the fluid conduit. At least one optical sensor may be configured to generate a signal. The holder may comprise an engagement feature configured to orient the receive portion of the fluid conduit in a predetermined rotational and vertical orientation relative to the at least one illumination source and the at least one optical sensor.

In some variations, the housing may comprise a light seal. In some variations, the one or more engagement features may be configured to orient the received portion of the fluid conduit by mating with an alignment feature of the received portion of the fluid conduit. In some variations, the one or more engagement features may comprise an open slot.

In some variations, the at least one illumination source may comprises a plurality of illumination sources. In some of these variations, the illumination sources may be configured to illuminate in a first illumination direction and a second illumination direction orthogonal to the first illumination direction.

In some variations, at least two of the illumination sources may be configured to illuminate along a first plane at a first wavelength. In some variations, at least another two of the illumination sources may be configured to illuminate along a second plane substantially parallel to the first plane. In some variations, the illumination sources may be configured to illuminate in a first illumination direction and a second illumination direction opposite the first direction.

In some of these variations, the illumination sources may be configured to illuminate in a first illumination direction and a second illumination direction 180 degrees offset from the first direction. In some of these variations, the illumination sources may comprise a first illumination source configured to emit light at a first wavelength between about 800 nm and about 900 nm. In some of these variations, the illumination sources may comprise a second illumination source configured to emit light at a second wavelength between about 400 nm and about 450 nm. In some of these variations, the illumination sources may comprise a third illumination source configured to emit light at a third wavelength between about 500 nm and about 550 nm. In some of these variations, the illumination sources may comprise a fourth illumination source configured to emit light at a third wavelength between about 230 nm and about 290 nm.

In some variations, the at least one optical sensor may comprise a plurality of optical sensors. In some variations, one or more of the at least one illumination source and the at least one optical sensor may comprise an anti-reflective coating. In some of these variations, the holder may define a longitudinal axis, and the optical sensors may be spaced apart parallel to the longitudinal axis.

In some variations, a controller may be configured to generate patient data based at least in part on the signal. In some variations, the patient data may comprise an infection state. In some variations, the device may further comprise a display. In some variations, the device may further comprise a communication device. In some variations, the device may comprise a base. The housing may be offset and spaced apart from the base. In some variations, the housing may comprise a peritoneal dialysis cycler. In some variations, the housing may comprise a hemodialysis device. In some variations, the housing may be configured to couple to one or more of a patient platform and medical cart.

In some variations, the housing may comprise a peritoneal dialysis device fluid path. In some variations, the fluid conduit may be coupled to a peritoneal dialysis tubing set. In some variations, the fluid conduit may be coupled to a peritoneal dialysis cycler tubing set. In some variations, the fluid conduit may be coupled to a peritoneal dialysis drain bag connector. In some variations, the fluid conduit may comprise an inlet portion, an outlet portion, and an optically transparent measurement portion between the inlet portion and the outlet portion, wherein the measurement portion comprises at least two substantially planar surfaces, a rotational alignment feature, and a depth alignment feature.

In some variations, at least one of the rotational alignment feature and the depth alignment feature may be configured to mate with the one or more engagement features of the holder. In some variations, a controller may be configured to generate patient data based at least in part on the signal. In some variations, the controller may be located remote from the housing. The device may further comprise a communication device configured to transmit data representative of the signal to the controller. In some variations, the controller may be configured to predict an infection score of a patient based at least in part on the signal. In some variations, the controller may be configured to predict an infection state of a patient in response to any one or more of the following: the infection score exceeding a predetermined threshold during each of one or more successive measurement time periods, the infection score increasing from a patient baseline over time, and the infection score having an increasing rate of change over time. In some variations, the infection state may comprise a probability of infection. In some variations, the fluid conduit may be configured to receive a patient fluid and the controller may be configured to estimate turbidity of the patient fluid based at least in part on the signal, wherein the infection score is based at least in part on the estimated turbidity.

In some variations, the controller may be configured to monitor a trend in infection score predicting infection resolution of the patient. In some variations, the controller may be configured to monitor a trend in infection score predicting infection resolution of the patient by predicting infection resolution in response to any one or more of the following: the infection score falling below a predetermined threshold during each of one or more successive measurement time periods, the infection score decreasing from a patient baseline over time, and the infection score having a decreasing rate of change over time.

Also described are methods for remote monitoring of a patient, that may include the steps of, at one or more processors, receiving an optical characteristic measurement of a patient fluid associated with the patient over a remote communication link. An infection score may be determined for predicting infection of the patient. The infection score may be based at least in part on the received optical characteristic measurement. In some variations, the patient may be associated with one of a plurality of patient infection states based at least in part on the determined infection score. In some variations, a user may be notified of the associated patient infection state. In some variations, a user may be prompted to perform one or more predetermined patient treatment actions based on the associated patient infection state. In some of these variations, the one or more predetermined patient treatment actions may comprise administering a broad spectrum antimicrobial to the patient. In some of these variations, the one or more predetermined patient treatment actions may comprise administering a pathogen-specific antimicrobial (e.g., antibiotic, antifungal, antiviral) to the patient. In some of these variations, the one or more predetermined patient treatment actions may comprise remotely monitoring a trend in infection score predicting infection resolution of the patient (based on the resultant efficacy of the antimicrobial treatment).

In some variations, remotely monitoring the trend in infection score predicting infection resolution may comprise predicting infection resolution in response to the infection score decreasing from a patient baseline over time. In some variations, remotely monitoring the trend in infection score predicting infection resolution comprises predicting infection resolution based on a rate of change of the infection score over time. In some variations, remotely monitoring the trend in infection score predicting infection resolution comprises predicting infection resolution in response to any one or more of the following: the infection score falling below a predetermined threshold during each of one or more successive measurement time periods, the infection score decreasing from a patient baseline over time, and the infection score having a decreasing rate of change over time.

In some variations, the plurality of patient infection states may comprise a first patient infection state corresponding to a healthy patient. In some variations, the plurality of patient infection states may comprise a second patient infection state corresponding to a patient brought to a medical care provider. In some variations, the plurality of patient infection states may comprise a third patient infection state corresponding to a patient who has received a broad spectrum antimicrobial treatment. In some variations, the plurality of patient infection states may comprises a third patient infection state corresponding to a patient who has received a pathogen-specific antimicrobial treatment. In some variations, the plurality of patient infection states may comprise a fourth patient infection state corresponding to a patient who has been hospitalized. In some variations, the plurality of patient infection states may comprise a fifth patient infection state corresponding to a patient who has been transitioned to hemodialysis. In some variations, the predicted infection may be peritonitis.

BRIEF DESCRIPTION OF THE DRAWINGS

FIG. 8C depicts a side view of an illustrative variation of a patient monitoring device in an open configuration.

FIGS. 18A, 18B, and 18F are cross-sectional side views of an illustrative variation of a vessel. FIGS. 18C, 18D, 18E, and 18H are perspective views of an illustrative variation of a vessel. FIG. 18G is a bottom plan view of an illustrative variation of a vessel. FIG. 18I is a detail view of section area B of FIG. 18H.

DETAILED DESCRIPTION

Figure 1:
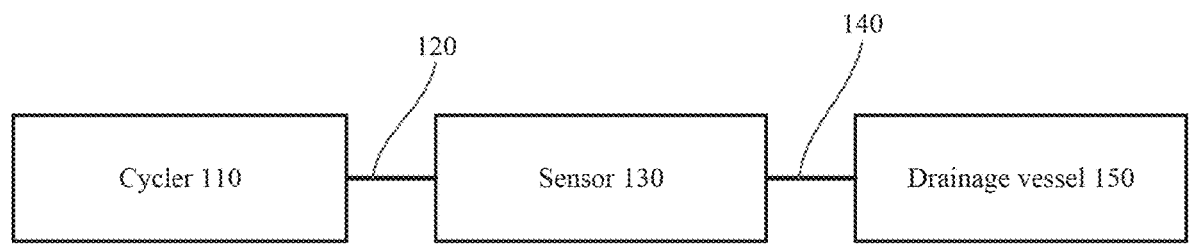
FIG. 1 depicts a block diagram of an illustrative variation of a patient monitoring system.

Described herein are methods, systems, and devices for monitoring patient fluid. The methods described herein may predict infection of a patient. In some variations, the systems and devices may monitor patients with end-stage renal disease that are prescribed peritoneal dialysis. For example, the systems described herein may comprise a patient monitoring device and a fluid conduit (e.g., disposable drain line extension) coupled between drain line tubing of a peritoneal dialysis night cycler and a drainage vessel such as a toilet. In some variations, the fluid conduit may comprise a vessel configured to be releasably received within a housing of the patient monitoring device. The fluid conduit may be independent of or integrated with another fluid conduit (e.g., drain line of a tubing set, other drain line extension, indwelling catheter, cassette). The patient monitoring device may comprise an optical sensor configured to measure the patient fluid through the vessel and generate a signal corresponding to one or more characteristics of a patient fluid flowing through the vessel. For example, the measured characteristic may be used to predict an infection state of the patient (e.g., probability of infection), estimate particle concentrations of the patient fluid, determine an operation state of a cycler (e.g., flow ON, flow OFF), fluid flow through the fluid conduit, and/or detect noise components (e.g., bubbles) of the patient fluid.

These systems and devices may be used in an ambulatory or home-based setting for continuous monitoring of complications, including but not limited to infections, catheter leakages, and catheter blockages. Patient compliance with the prescribed treatment may be monitored and communicated to the patient and/or health care providers. Treatment efficacy may also be remotely monitored over time to indicate a patient's response to the prescribed treatment. As such, providers may monitor patients more frequently than what may be practical through solely in-person clinic visits. Infections may be predicted and quantified in real-time and allow providers to address complications before problems exacerbate and become more difficult to resolve. For example, when detected and treated early, infections may be treated with an antibiotic regimen that may prevent patient hospitalization. Infection resolution may be monitored upon initiation of the antibiotic treatment and may be updated at predetermined intervals. For example, when treatment efficacy is positive, the prescribed medical therapy (e.g., drug, dosage, frequency) may be updated immediately to limit the antibiotics taken by the patient to the minimum necessary to resolve the infection. In some variations, the systems, devices, and methods disclosed herein may comprise one or more systems, devices, and methods of treatment administration and sample collection described in International Patent Application Serial No. PCT/US2018/065853, filed on Dec. 14, 2018, the contents of which are hereby incorporated by reference in its entirety. For example, the tool may automate antimicrobial administration and/or culture sample collection (e.g., based on algorithmic determination of infection score as described below), which may reduce response periods from patient and/or medical care provider(s), thereby improving patient outcomes.

In some variations, a patient monitoring system may comprise a sensor configured to monitor fluid flowing from a peritoneal dialysis machine ("cycler") to a drainage vessel. FIG. 1 depicts a block diagram of a patient monitoring system (100) comprising a cycler, drain line (120), sensor (130), fluid conduit (140), and drainage vessel (150). In some variations, the cycler (110) may be configured to pump patient fluid (e.g., dialysate) into the drain line (120). The drain line (120) may be fluidly coupled to the fluid conduit (140) and a drainage vessel (150) (e.g., toilet, drain pan, drain basin, waste bucket, waste bag, tub, sink, etc.) may be configured to receive the patient fluid. A portion of the fluid conduit (140) may be received by and aligned to the sensor (130) to measure an optical characteristic of the patient fluid through the fluid conduit (140), as described in more detail herein.

Figure 2:
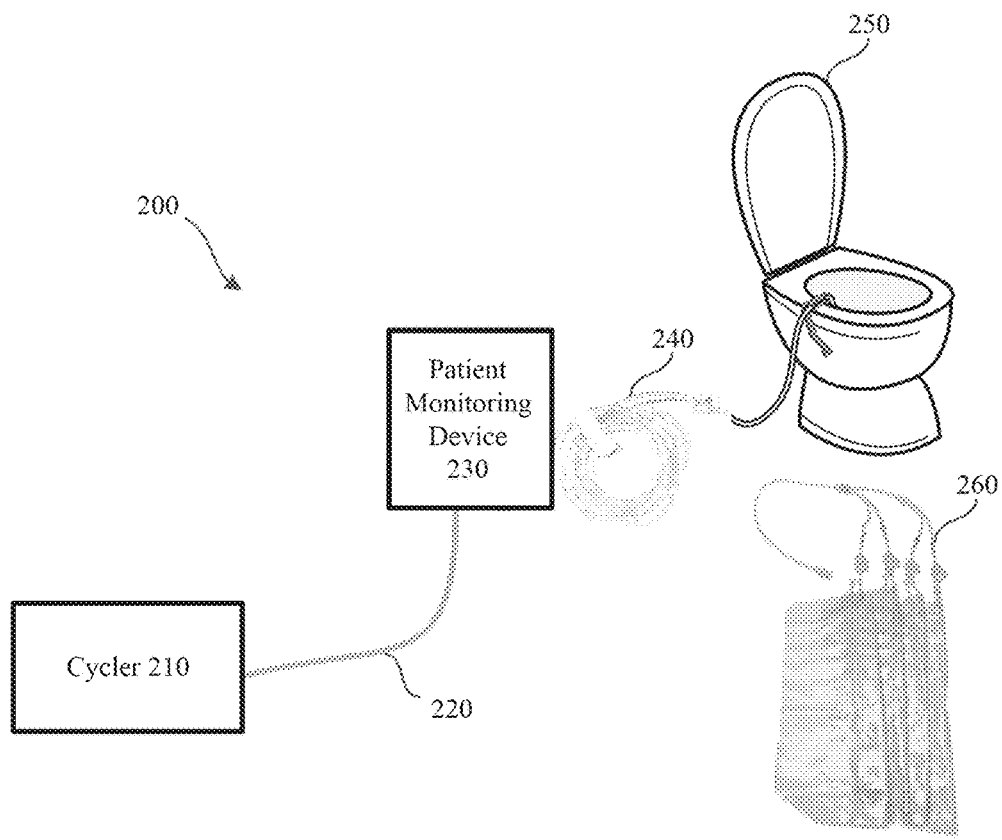
FIG. 2 depicts a schematic diagram of an illustrative variation of a patient monitoring system.

FIG. 2 depicts a schematic diagram of a patient monitoring system (200) that may be used in, for example, a patient's home or in a clinic setting. The patient monitoring system (200) may comprise a cycler (210), drain line (220), patient monitoring device (230), fluid conduit (240), and drainage vessel (250, 260). In some variations, the cycler (210) may be configured to pump patient fluid (e.g., dialysate) into the drain line (220). The drain line (220) may be fluidly coupled to the fluid conduit (240) and a drainage vessel such as toilet (250) or bag (260) may be configured to receive the patient fluid. A portion of the fluid conduit (140) may be received by and aligned to the patient monitoring device (230). For example, the patient monitoring device (230) may comprise an optical sensor configured to measure an optical characteristic of the patient fluid through the fluid conduit (240). In some variations, an optically transparent vessel may be received and aligned to the patient monitoring device (230). The patient monitoring device (230) may be a durable component comprising a sensor configured to measure and analyze the patient fluid in a non-contact manner, and notify one or more of the patient and provider of the analysis. At least in part because the fluid conduit (240) and patient monitoring device (230) retrofit into conventional dialysis setups, the use of the fluid conduit (240) and patient monitoring device (230) with a cycler (210) system may add only a relatively small amount of time and number of steps to a patient's dialysis setup and maintenance routine while providing real-time patient monitoring of patient fluid for infection detection and fluid characteristics.

In some variations, the fluid conduit and/or vessel may be a disposable component that may be replaced at predetermined intervals (e.g., after a dialysis session, daily, weekly, etc.). The fluid conduit and/or vessel may serve as a drain line extension of a predetermined length and may comprise one or more connectors configured to fluidly couple to conventional tubing connectors. For example, the fluid conduit may extend a drain line to a predetermined length so as to provide fluidic connection between a cycler (210) placed in a bedroom and a toilet (250) or other drainage vessel placed in a bathroom. In some variations, the patient monitoring device (230) may be configured to attach to one or more of a patient platform, a medical cart, and medical device (e.g., IV pole). A patient platform may include, for example, a surface for a patient (bed, chair, table, hospital bed, intensive care unit bed, etc.).

Also described are methods that may be performed using the systems and devices described herein. In some variations, methods of predicting infection of a patient may predict an infection state of the patient based on an estimated turbidity of the patient fluid. For example, generally, infection may be correlated with the concentration of one or more particle types, such as leukocytes, in the patient fluid. The concentration of leukocytes and/or other particle types may be estimated based on various optical parameters (e.g., turbidity) of the patient fluid, as estimated using methods and devices such as those described herein. The estimated turbidity may be estimated based on a measured optical characteristic of the patient fluid. For example, the optical characteristic may comprise one or more of optical scatter and obscuration light intensity measurements.

In some variations, the composition of a patient fluid may be estimated based on measured optical characteristics of a patient fluid. In particular, the type and concentration of particles in the patient fluid may be estimated based on optical measurements. The particles may comprise, for example, leukocytes, erythrocytes, protein, and triglycerides. For example, the optical characteristics may be measured at a plurality of wavelengths. In another example, the composition may be estimated based on an optical characteristic of static patient fluid measured over a predetermined time period.

In some variations, an infection score of the patient may be predicted based on a set of measured optical characteristics generated over time. For example, the infection score may be compared to a predetermined threshold or patient baseline to predict the state of infection such as onset and resolution. Analyzing a set of infection scores over time (as a surrogate for the rate of change of measured optical characteristics) may reduce false positives and thereby improve the sensitivity and specificity of patient diagnosis and allow prediction of a patient infection state (e.g., probability of infection).

In some variations, a patient infection state may comprise a first infection state corresponding to an infected patient and a second infection state corresponding to an uninfected patient. In some variations, a patient infection state may correspond to a probability that the patient is infected. In some variations, an infection probability may correspond to an infection score. For example, a patient infection state may correspond to the first infection state when an infection probability is at or above a predetermined threshold (e.g., 60%, 65%, 70%, 75%, 80%, 85%, 90%, 95%, etc.) and may correspond to the second infection state when the infection probability is below the predetermined threshold or other suitable different threshold (e.g., a first threshold for infection probability may be used to determine an infection state, while a second threshold for infection probability may be used to determine an uninfected state).

In some variations, a patient monitoring device may measure optical characteristics of fluid based on an operating state of a cycler. For example, a cycler of a patient monitoring system may perform the steps of pumping patient fluid into a drain line (drain cycle), then stop the pump such that fluid is static within the drain line during the steps when the cycler is pumping fluid into the patient line (infusion cycle) or the cycler is stopped while the fluid is dwelling within the patient (dwell cycle). In some variations, a patient monitoring device may obtain sensor measurements and analyze the measurements according to the operating state of the cycler. For example, the sensor measurements may be performed during a drain cycle of the cycler and OFF during an infusion cycle and/or a dwell cycle. Additionally or alternatively, optical characteristics of fluid flow in a continuous ambulatory peritoneal dialysis (CAPD) system may be measured. Additionally or alternatively, different turbidity algorithms may be applied to one or more of the drain cycle, infusion cycle, and dwell cycle. As described in more detail herein, methods of estimating a fluid flow rate (e.g., pump ON/OFF) of a patient fluid may correspond to an operating state of a cycler. The estimated fluid flow rate may be used to ensure accurate fluid sensing, distinguish fluid properties for each drainage (when the treatment cycle has more than one drainage), reduce energy consumption, and increase the lifespan of the patient monitoring device. In some variations, fluid flow rate may comprise a set of fluid flow states. For example, a first fluid flow state may comprise a continuous fluid flow through a fluid conduit (e.g., continuous fluid pumping through a drain line) and a second fluid flow state may comprise a non-continuous fluid flow through the fluid conduit (e.g., no fluid pumping through a drain line). In some variations, fluid flow rate may comprise a volume of fluid passing through a given cross-sectional area per unit time.

Optical measurements of fluid may suffer from discrete sources of noise such as bubbles or large particulate matter. In some variations, methods of detecting a bubble may be performed and allow such signal data to be excluded so as to increase a signal-to-noise ratio of the optical measurements. Other sources of noise such as fibrin particles, patient bleeding, ascites fluid drainage, and the like may be detected and excluded from the optical measurements used in fluid analysis.

The systems, devices, and methods described here may be used in a variety of different dialysis therapies to treat kidney failure. For example, dialysis therapy may comprise any and all therapies that utilize fluids (e.g., patient's blood, dialysate) to remove waste, toxins, and excess water from the patient. Such therapies may comprise hemodialysis, hemofiltration, hemodiafiltration (HDF) and peritoneal dialysis, including automated peritoneal dialysis, continuous ambulatory peritoneal dialysis, and continuous flow peritoneal dialysis. Such therapies may also comprise, where applicable, both intermittent therapies and continuous therapies used for continuous renal replacement therapy. Patients treated with dialysis therapies may comprise patients with chronic renal failure, as well as those with acute renal failure, whether resulting from renal or non-renal disease.

The terms 'transparent', 'transparency', and variants thereof are used throughout the specification. However, it should be understood that these terms do not require complete or 100% transmission of light.

Patient Monitoring System

The patient monitoring systems described herein may be configured to monitor patient fluid and predict patient infection and/or other patient fluid characteristics. In some variations, the patient monitoring system may be configured to provide additional functionality to current peritoneal dialysis systems. For example, the patient monitoring system may comprise a fluid conduit configured to extend a length of one or more of a drain line, tubing, and catheter. A patient monitoring device may be configured to analyze patient fluid in the fluid conduit to monitor infection, measure turbidity, estimate the composition of the fluid, and/or detect fluid flow, etc. The patient monitoring device may further output the results of the fluid analysis to a patient and/or provider and enable monitoring of the onset and resolution of an infection.

In some variations, the patient monitoring systems described herein may comprise a patient monitoring device (e.g., durable electro-mechanical system) configured to engage with a fluidic component (e.g., vessel, fluid conduit). For example, the fluidic component may comprise a disposable vessel (e.g., fluid conduit, cartridge, drain line, tubing, in-dwelling catheter) and may be configured to removeably engage a patient monitoring device (e.g., housing, holder, optical sensor arrangement, display screen, wireless transmitter, etc.). In some variations, the patient monitoring device may include at least one sensor and a processor to measure patient fluid and predict patient infection. The fluidic component may include fluid contacting components and the patient monitoring device may include a set of non-fluid contacting components. The fluidic component may be disposable. For example, the fluidic component may be replaced at predetermined intervals (e.g., daily, weekly) and/or predetermined criteria (e.g., patient infection event). A disposable fluidic component may, for example, be useful for short-term use since biofouling within the fluid conduit over time may obfuscate (e.g., cloud) an optical measurement region, causing inaccurate measurements, and result in an unacceptable number of false-positive and/or false-negative patient infection outputs. The durable component may provide long-term functionality given proper maintenance (e.g., cleaning). In some variations, fluid characteristics such as optical scatter, optical absorption, attenuation detection angle, and/or fluid flow rate may be measured in a non-fluid contact manner using the durable component without separate sensors in the fluidic component. As a result, manufacture of the fluidic component may be simplified for high-volume manufacturing and provided at reduced cost. The durable component may comprise a set of structure, materials, and techniques configured to provide high optical quality for optical sensor measurement. For example, the durable component may comprise a structure configured to reduce ambient light leakage and refraction while being suitable for the draft angle requirements and higher manufacturing tolerances associated with injection molding. In some variations, the fluidic component may be formed by, for example, one or more of injection molding, machining, solvent bonding, interference/press fit assembly, ultrasonic welding, and 3D printing techniques. For example, separate portions of a fluidic component may be injection molded and attached using a solvent to further reduce manufacturing cost. In some variations, a fluidic component may be integrated into a drain line set through solvent bonding and/or adhesives to further reduce complexity of the system. Furthermore, the fluidic component may be configured to attach to existing drain line sets to provide additional functionality to existing peritoneal dialysis systems. Additionally or alternatively, a disposable vessel such as a cartridge, tubing, catheter, drain line, and the like may comprise an optically transparent measurement portion as described herein.

Figure 3B:
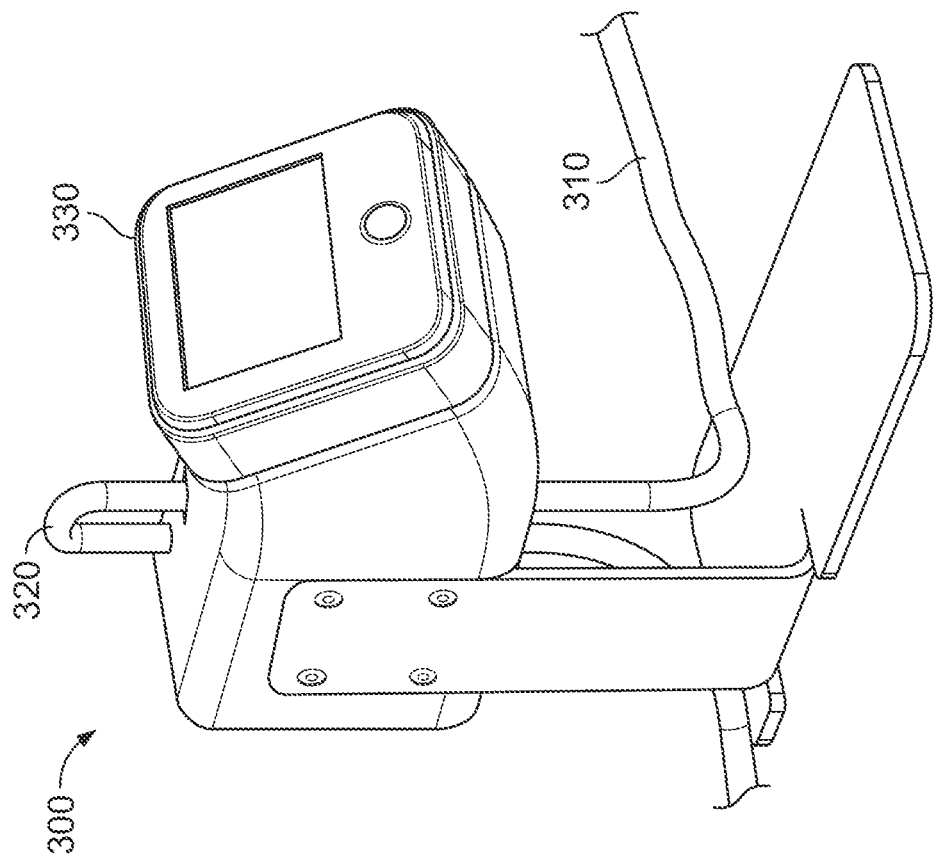
FIGS. 3A and 3B depict right and left perspective views, respectively, of an illustrative variation of a patient monitoring device.
Figure 3A:
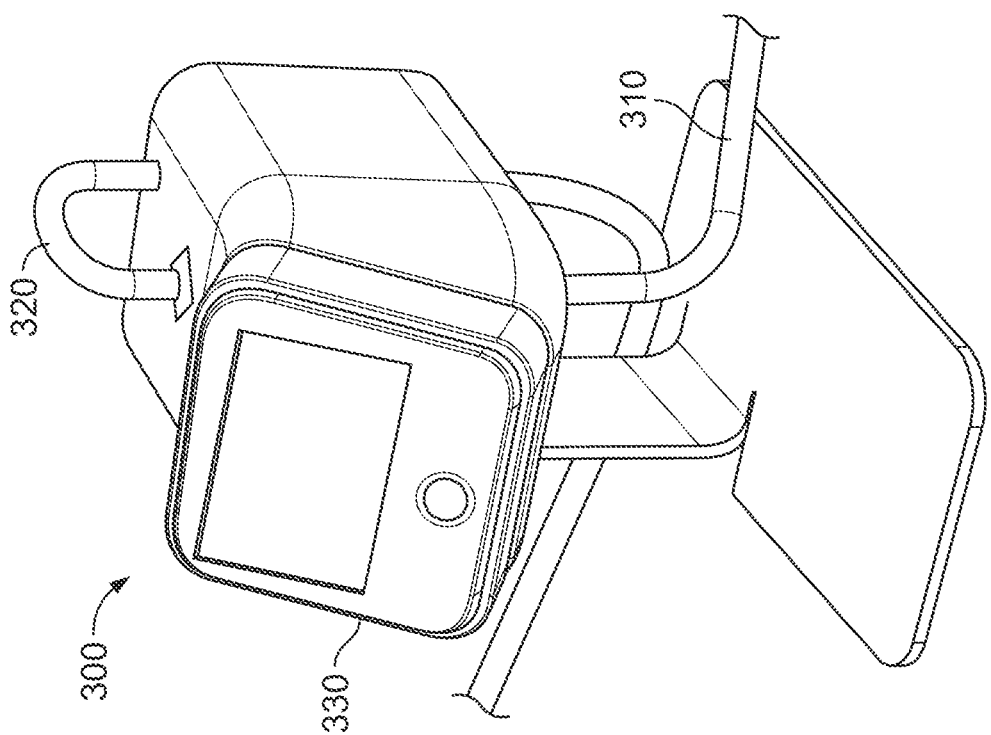

FIGS. 3A and 3B are perspective views of a patient monitoring system (300) comprising a first fluid conduit (310), second fluid conduit (320), and patient monitoring device (330). As described in more detail herein, the fluid conduit may be releasably coupled to the patient monitoring device, and the fluid conduit may be a disposable component that is replaced at predetermined intervals. The use of the patient monitoring device may add only a few simple, additional steps to the setup procedure of a conventional peritoneal dialysis cycler system for administration of continuous cycling peritoneal dialysis (CCPD). For example, the fluid conduit may be coupled to and released from a drain line and drainage vessel (not shown in FIG. 3) in the same manner as a conventional drain line extension, thus adding no additional setup time for the patient. Moreover, one or more engagement features of the patient monitoring device may guide the assembly of the fluid conduit via interaction with one or more alignment features of the fluid conduit (e.g., rotational and/or depth alignment features) to prevent misalignment, thus reducing patient error and compliance issues. Once the fluid conduit is coupled to the patient monitoring device, the measurement and analysis of the patient fluid may be performed and output to the patient's care provider without additional patient action. Removal of the fluid conduit may simply require a reversal of the assembly steps. Accordingly, the patient monitoring device adds numerous quantitative patient monitoring capabilities while being simple and efficient to set up, operate, and maintain.

In some variations, the patient monitoring system (300) may comprise an input device (e.g., switch, push button, voice command) configured to activate an optical sensor and/or predict an infection state of the patient. The patient may initiate optical sensor measurement in conjunction with fluid drainage (e.g., drainage of effluent). The patient monitoring device (300) may, for example, be attached to or incorporated with one or more of an IV pole or medical cart. For example, the patient monitoring system (300) may be used for the administration of continuous ambulatory peritoneal dialysis (CAPD).

Figure 4A:
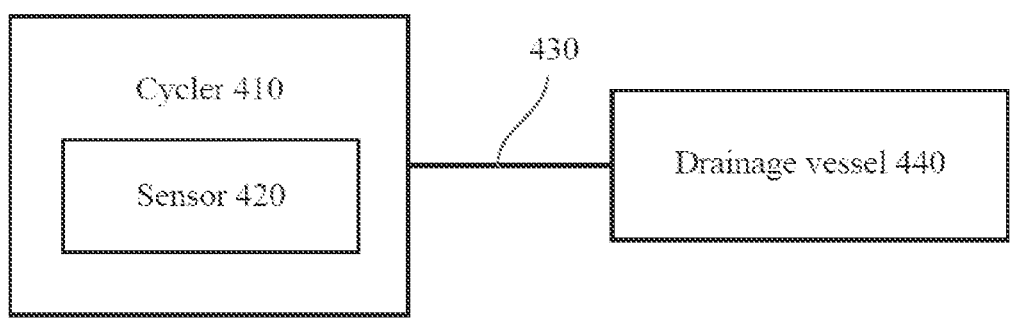
FIGS. 4A, 4B, and 4C depict block diagrams of other illustrative variations of a patient monitoring system.

Additionally or alternatively, one or more components of the patient monitoring devices described herein may be integrated into other devices. FIG. 4A depicts a block diagram of a patient monitoring system (400) comprising a cycler (410), a cycler tubing set drain line (430), and drainage vessel (440). The cycler (410) may comprise a sensor (420) as described herein. In some variations, the cycler (410) may be configured to pump patient fluid (e.g., dialysate effluent) into the drain line (430). The drain line (420) may be fluidly coupled to the drainage vessel (440). An optical characteristic of the patient fluid flowing through the cycler (410) may be measured by the sensor (420). For example, the sensor (420) may be configured to measure an optical characteristic of an optically transparent measurement portion of a disposable cycler cassette.

Figure 25A:
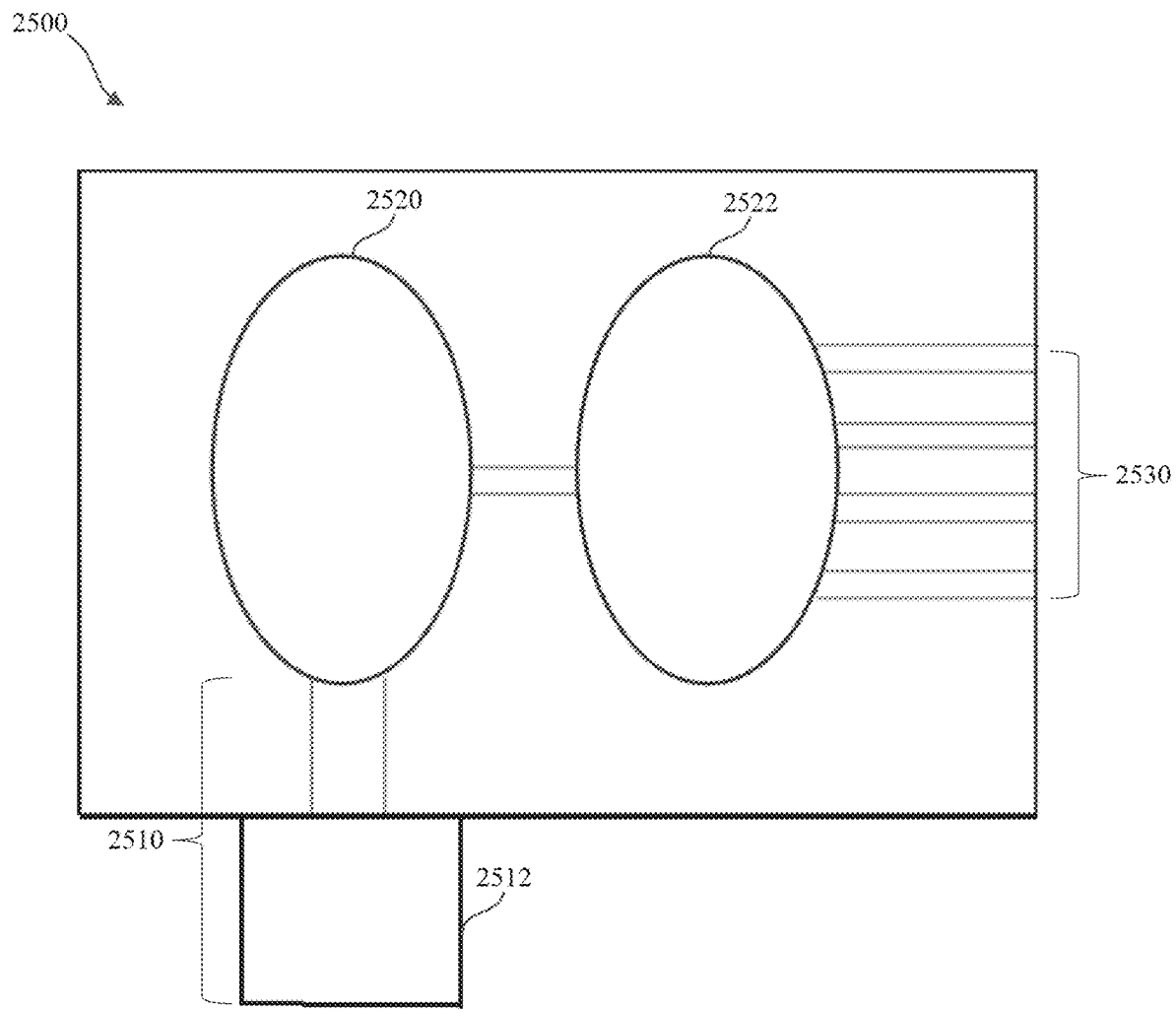
FIG. 25A is a schematic side view diagram of an illustrative variation of a cassette for use with a peritoneal dialysis cycler with an optical measurement region.

In some variations, a cassette for a peritoneal dialysis cycler may be configured to allow measurement of an optical characteristic of patient fluid (e.g., dialysate effluent) flowing therethrough. FIG. 25A is a schematic diagram of a tubing set cassette (2500) for use with a peritoneal dialysis cycler. While additional fluid channels are typically required for infusion and drainage of fluid into the patient from multiple fluid sources, for clarity, only a subset of fluid channels are depicted. The cassette (2500) may comprise an inlet (2510), optical measurement region (2512), first reservoir (2520), second reservoir (2522), and outlet (2530). The inlet (2510) may be configured to connect directly to a patient in-dwelling catheter and both receive patient fluid (e.g., dialysate effluent) and infuse fluid (e.g. fresh dialysate) to the in-dwelling catheter and may fluidly couple to the first reservoir (2520). The inlet (2510) may comprise a generally optically transparent measurement portion (2512) having one more optical properties and/or structural characteristics similar to an optical measurement portion of the vessels described herein. In addition to the patient effluent fluid measurement, the optical measurement region (2512) may be configured to measure the properties of infused fluid (e.g. fresh dialysate) as a method of verifying the quality of the fluid (e.g. cleanliness). In another variation, measurement of the infused fluid may be used to calibrate the optical measurements using a baseline measurement. Thus, a measure optical characteristic of the patient fluid may include subtraction of the baseline measurement from the measured optical signal. This calculation may reduce one or more sources of measurement variability including optical variance of the infused fluid, optical variance of the optical measurement portion (including fouling over time), and variance in the illumination source (e.g., light intensity) and/or optical sensor (e.g., electrical noise).

Figure 25B:
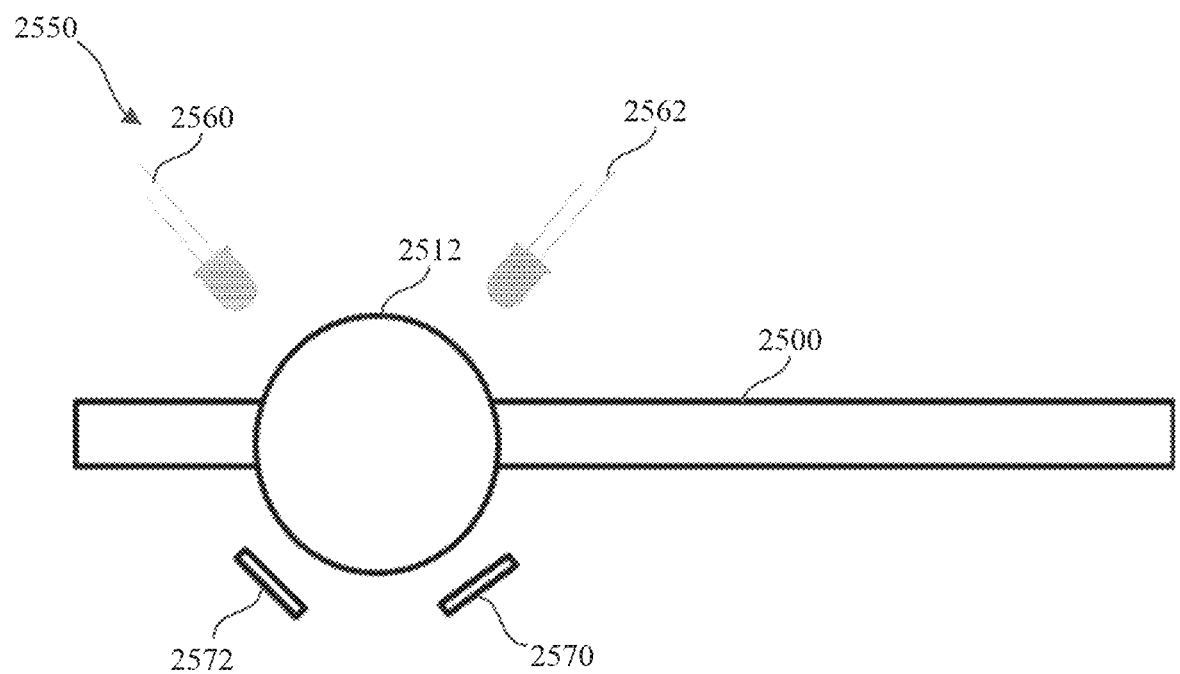
FIG. 25B is a schematic top view diagram of an illustrative variation of a cassette with an optical measurement region interface for an optical sensor(s) of a peritoneal dialysis cycler.

FIG. 25B is a schematic cross-section top view diagram of the cassette (2500) depicted in FIG. 25A comprising an optical measurement portion (2512) interface to an optical sensor arrangement (2550) of a peritoneal dialysis cycler. The optical sensor arrangement (2550) may comprise a set of illumination sources (2560, 2562) and optical sensors (2570, 2572). The optical sensor arrangement (2550) may be configured to measure one or more optical characteristics of a patient fluid and provide for illumination from a plurality of illumination directions. A first illumination source (2560) may illuminate an optical measurement portion (2512) in a first illumination direction and a second illumination source (2562) may illuminate the optical measurement portion (2512) in a second illumination direction orthogonal to the first illumination direction. Alternatively, the first illumination source may have a first illumination direction that is 180 degree offset from the second illumination direction such that the illumination sources may direct light in opposite directions. In some variations, the patient fluid may be illuminated from a plurality of non-parallel illumination directions. For example, the first illumination direction may have an offset from the second illumination direction of between more than about 0 degrees and about 180 degrees. In some variations, the first illumination source (2560) and the second illumination source (2562) may be configured to provide illumination at the same wavelength.

In FIG. 25B, a first optical sensor (2570) and a second optical sensor (2572) may be configured to generate a signal corresponding to measurement of an optical characteristic of the illuminated patient fluid. The first and second optical sensors may, for example, be photodiodes. An optical sensor may be configured to measure one or more of optical scatter and attenuation detection angle (e.g., absorption, obscuration). For example, the optical sensors may be configured to measure a property of illuminated patient fluid at an attenuation/absorption/obscuration angle (about 180 degrees), forward scattering angles (about >90 degrees about <180 degrees), side scattering angle (about 90 degrees), and back-scattering angles (about <90 degrees, about ≥0 degrees). In FIG. 25B, the first optical sensor (2570) faces the first illumination source (2560) (the first optical sensor and the first illumination source are on opposite sides of the optical measurement portion (2512)), and the second optical sensor (2572) faces the second illumination source (2562) (the second optical sensor and the second illumination source are on opposite sides of the optical measurement portion (2512)). Alternatively, the first optical sensor (2570) may be generally orthogonal to the first illumination source (2560), and the second optical sensor (2572) may be generally orthogonal to the second illumination source (2562). Turbidity of the patient fluid may be estimated based on measured optical characteristics and the turbidity equations described in more detail herein.

Figure 5A:
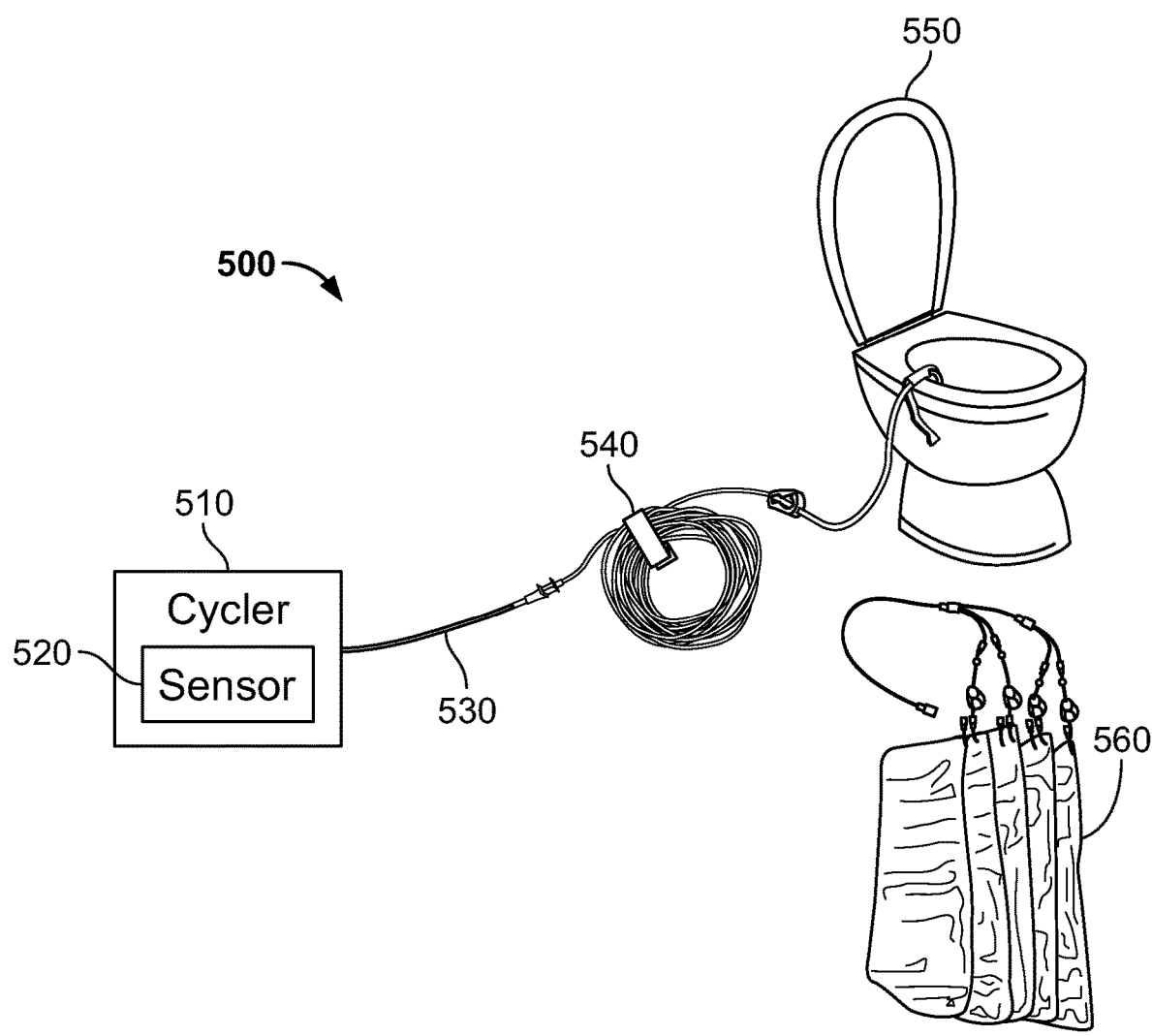
FIGS. 5A, 5B, 5C, and 5D depict schematic diagrams of other illustrative variations of a patient monitoring system.

The cassette may comprise one or more ambient light shielding features configured to enhance the optical measurement of patient fluid. FIG. 5A depicts a schematic diagram of a patient monitoring system (500) that may be used in, for example, a patient's home. The patient monitoring system (500) may comprise a cycler (510), drain line (530), drain line extension (540), and drainage vessel (550, 560). The cycler (510) may comprise a sensor (520). In some variations, the cycler (510) may be configured to pump patient fluid into the drain line (530). The drain line (530) may be fluidically coupled to the drain line extension (540) and a drainage vessel such as toilet (550) or bag (560) configured to receive the patient fluid.

Figure 4B:
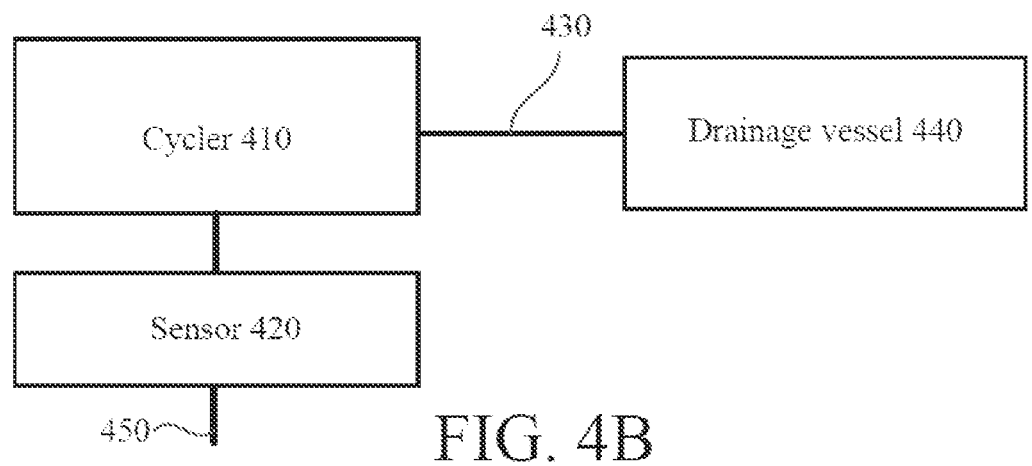

In some variations, a sensor (420) may be coupled to a drain line extending from a cycler (e.g., coupled to a drainage prong of a cassette of a cycler). For example, FIG. 4B illustrates an exemplary configuration of a patient monitoring system (400) comprising an optically transparent measurement portion (450), a sensor (420), a cycler (410), a cycler tubing set drain line (430), and a drainage vessel (440). For example, an in-dwelling catheter or tubing set may comprise the optically transparent measurement portion (450), which may be releasably coupled to one or more of a sensor (420) and a disposable cycler cassette of a cycler (410). For example, the optically transparent measurement portion (450) may be disposed along a proximal end of the in-dwelling catheter. An optical characteristic of the patient fluid flowing through the measurement portion (450) may be measured by the sensor (420). In some variations, patient fluid may flow through the measurement portion (450) and then the cycler (410). The cycler (410) may be configured to receive and pump patient fluid (e.g., dialysate effluent) into the drain line (430). The drain line (420) may be fluidly coupled to the drainage vessel (440).

Figure 4C:
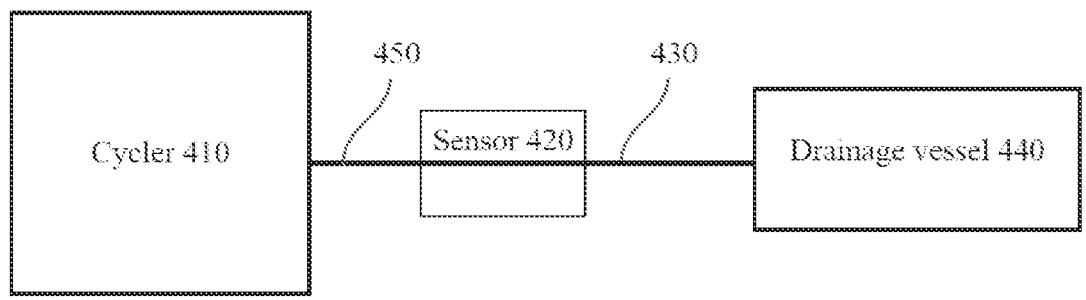

FIG. 4C illustrates an exemplary configuration of a patient monitoring system (400) comprising an optically transparent measurement portion (450), a sensor (420), a cycler (410), a cycler tubing set drain line (430), and a drainage vessel (440). For example, a tubing set may comprise the optically transparent measurement portion (450), which may be releasably coupled to one or more of a sensor (420) and a disposable cycler cassette of a cycler (410). An optical characteristic of the patient fluid flowing through the measurement portion (450) may be measured by the sensor (420). In some variations, patient fluid may flow through the cycler (410) and then through the measurement portion (450) coupled in-line with the drain line (430). The drain line (430) may be fluidly coupled to the drainage vessel (440).

Figure 5B:
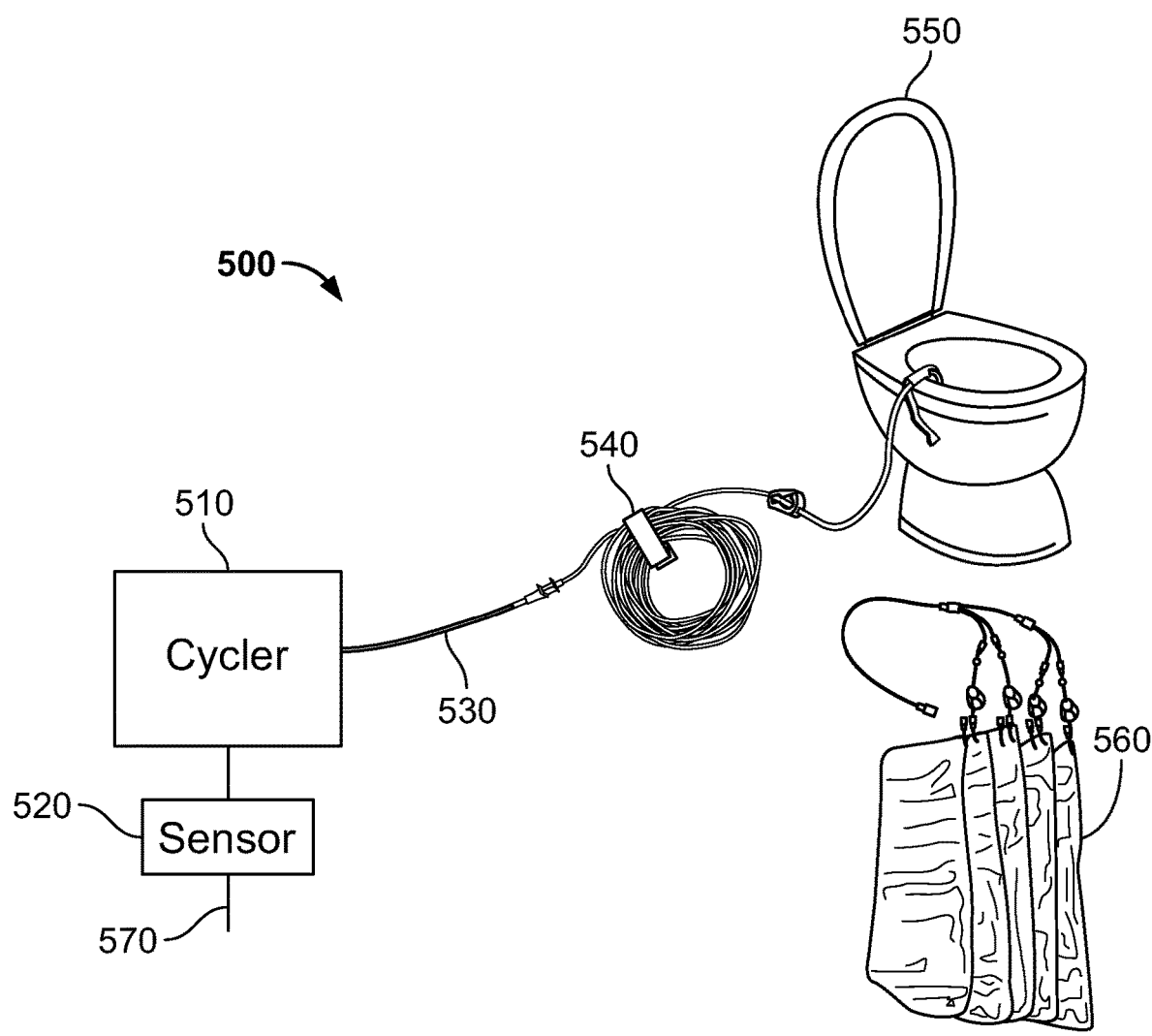

FIG. 5B depicts a schematic diagram of a patient monitoring system (500) that may be used in, for example, a patient's home. The patient monitoring system (500) may comprise a catheter or tubing set (570), a sensor (520), a cycler (510), a drain line (530), a drain line extension (540), and a drainage vessel (550, 560). The sensor (520) may be releasably coupled to the tubing set (570) downstream of the cycler (510). In some variations, the cycler (510) may be configured to pump patient fluid into the drain line (530). The drain line (530) may be fluidically coupled to the drain line extension (540) and a drainage vessel such as toilet (550) or bag (560) configured to receive the patient fluid.

Figure 5C:
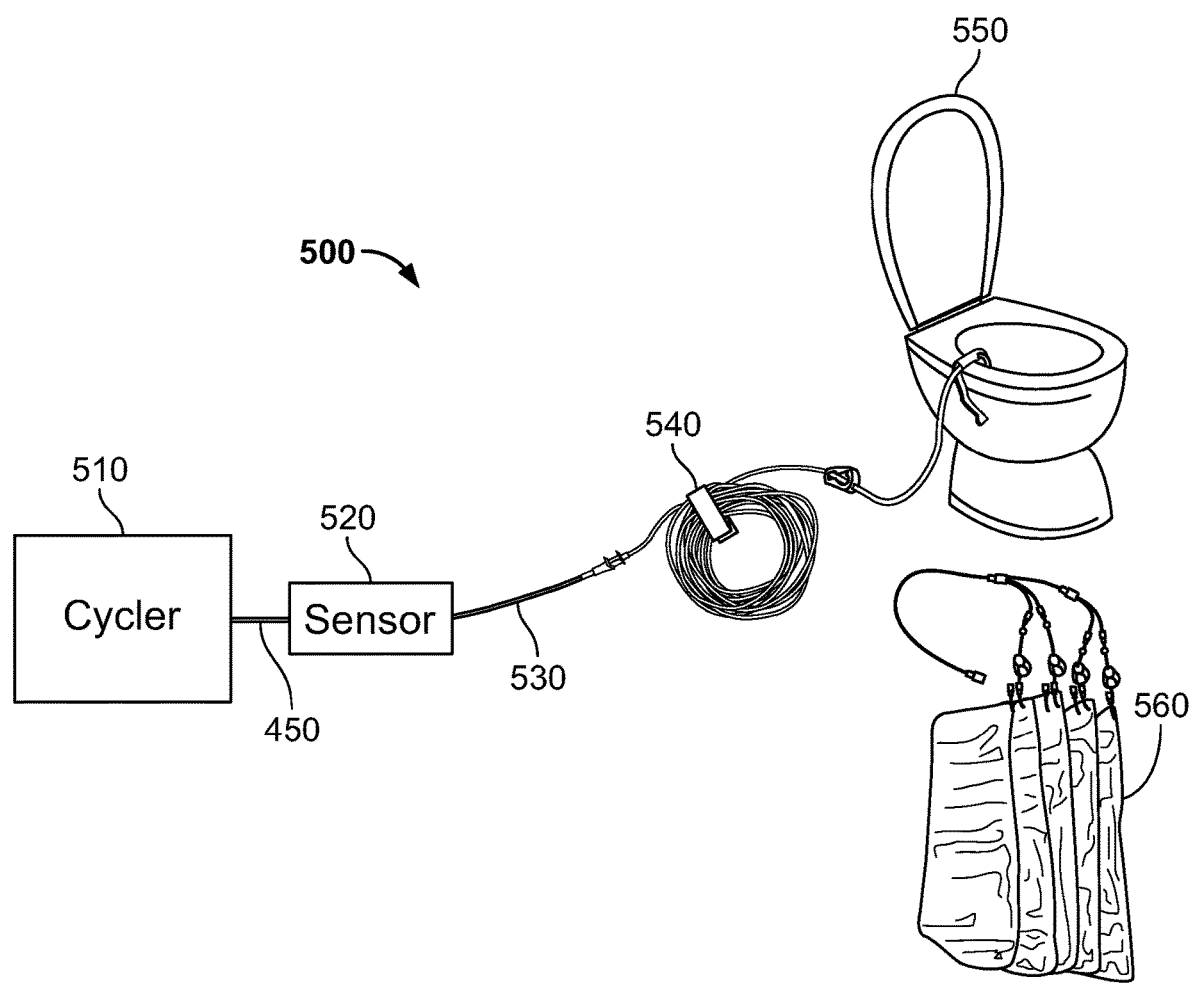
Figure 5D:
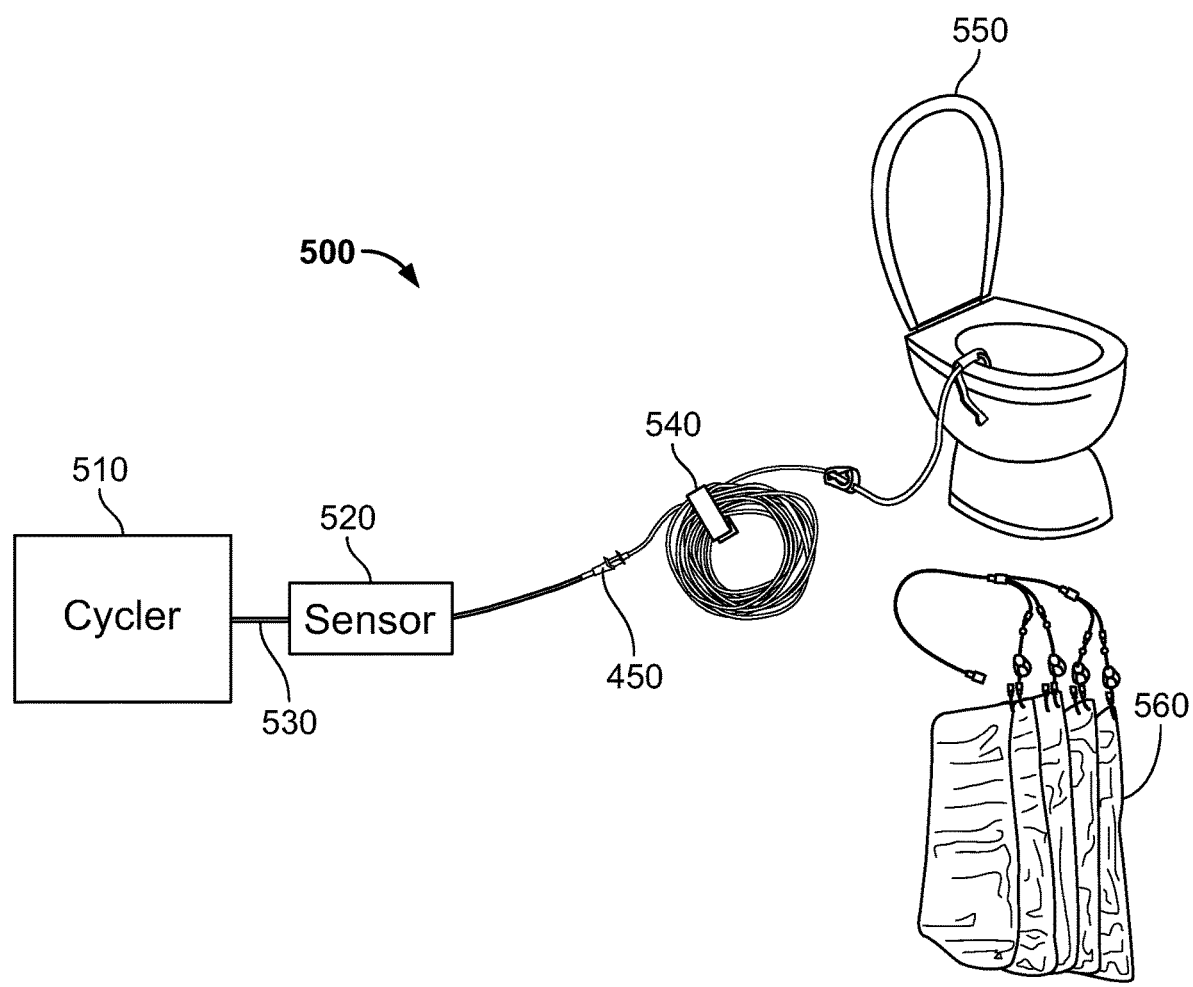

FIG. 5C depicts a schematic diagram of a patient monitoring system (500) that may be used in, for example, a patient's home. The patient monitoring system (500) may comprise a cycler (510), a sensor (520), an optically transparent measurement portion (450), a drain line (530), a drain line extension (540), and a drainage vessel (550, 560). The sensor (520) may be releasably coupled to the optically transparent measurement portion (450), downstream of the cycler (510). In some variations, the optically transparent measurement portion (450) may be coupled with the drain line extension (540) as a continuous fluidic path, as shown in FIG. 5D.

Patient Monitoring Device

The patient monitoring devices described here may be configured to monitor patient fluid and predict patient infection and/or other characteristics of the patient fluid. For example, the patient monitoring device may be configured to optically measure one or more characteristics of patient fluid flowing through a fluid conduit coupled to the patient monitoring device. Furthermore, the patient fluid in the fluid conduit may be analyzed to monitor infection, measure turbidity, estimate the composition of the fluid, and detect fluid flow. The patient monitoring device may further output the results of the fluid analysis to a patient and/or provider and enable monitoring of the onset and resolution of an infection. In some variations, the patient monitoring devices described herein may be configured for use in a dialysate infusion system or may comprise a stand-alone point-of-care fluid sample analysis device. For example, in some variations, a fluid vessel may be configured as a vial to hold a static, predetermined volume of fluid for analysis using the patient monitoring device. Furthermore, in some variations, the patient monitoring device may be configured to compactly fit on a surface (e.g., table, desk) and be used to analyze a patient fluid using any of the methods described herein. For example, the patient monitoring device need not comprise a base (e.g., stand) to reduce a volume of the device.

Figure 6:
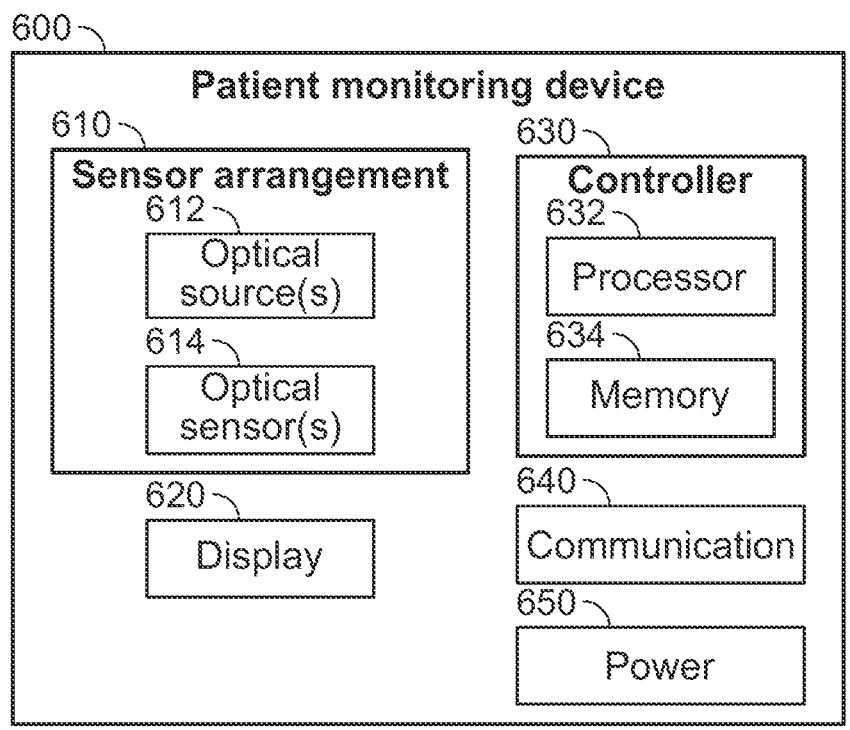
FIG. 6 depicts a block diagram of an illustrative variation of a patient monitoring device.

FIG. 6 depicts a block diagram of a patient monitoring device (600) comprising a sensor arrangement (610), display (620), controller (630), communication device (640), and power source (650). The optical arrangement (610) may comprise an optical source (612) (e.g., illumination source) and an optical sensor (614). The optical source (612) may be configured to illuminate patient fluid within a vessel and/or fluid conduit. The optical sensor (614) may be configured to measure an optical characteristic of the illuminated patient fluid. The controller (630) may comprise a processor (632) and memory (634) configured to process, analyze, and/or store the measured signal data, determine when the flow is indicative of a drainage cycle, and used to further determine when to measure the patient fluid. For example, the controller (630) may be configured to generate patient data based at least in part on a signal measured by the optical sensor (614). The patient data may comprise, for example, an infection state (e.g., probability of infection).

Figure 7A:
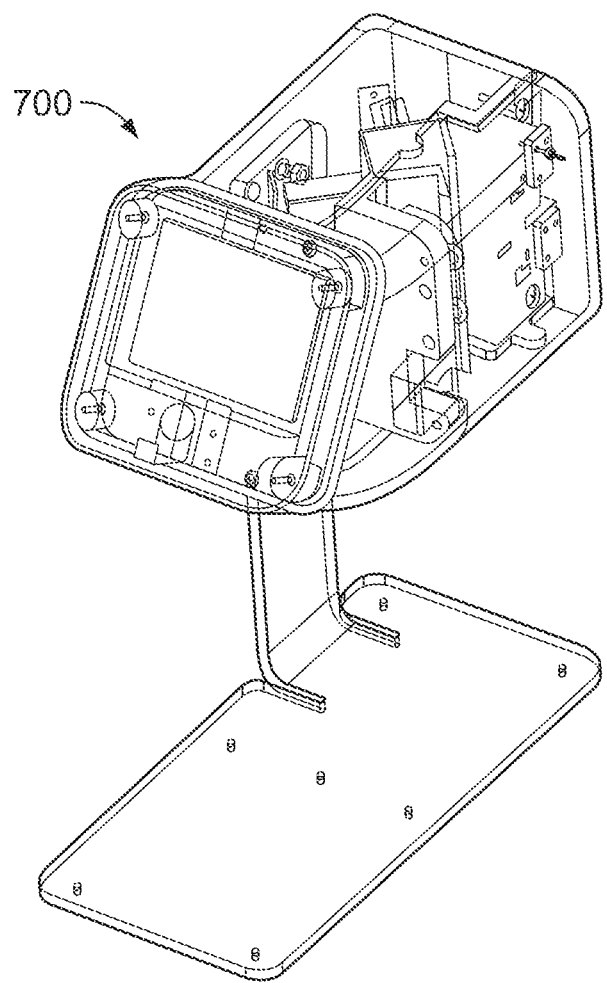
FIG. 7A depicts a perspective view of an illustrative variation of a patient monitoring device.
Figure 7B:
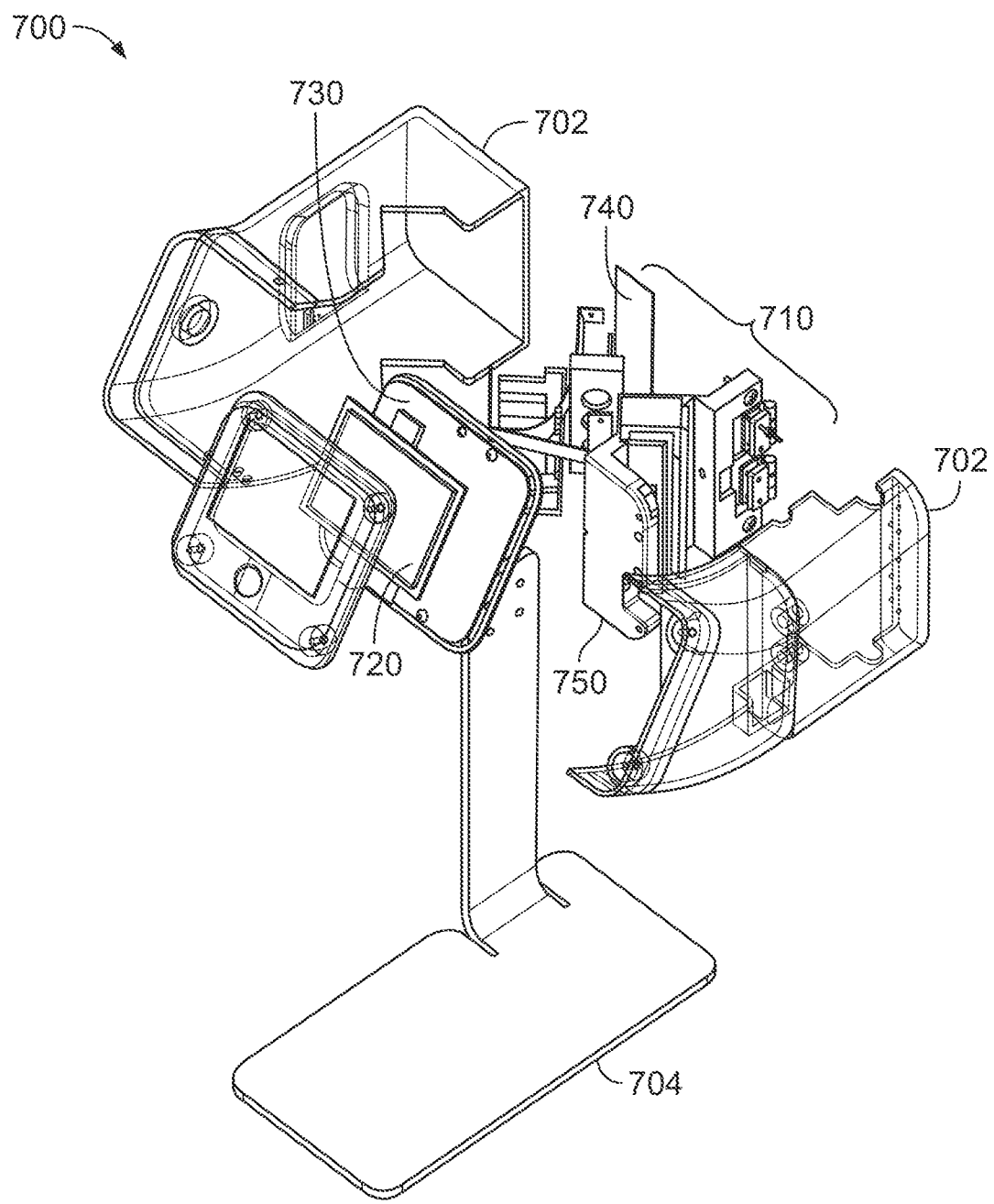
FIG. 7B depicts an exploded schematic diagram of the patient monitoring device shown in FIG. 7A.
Figure 8A:
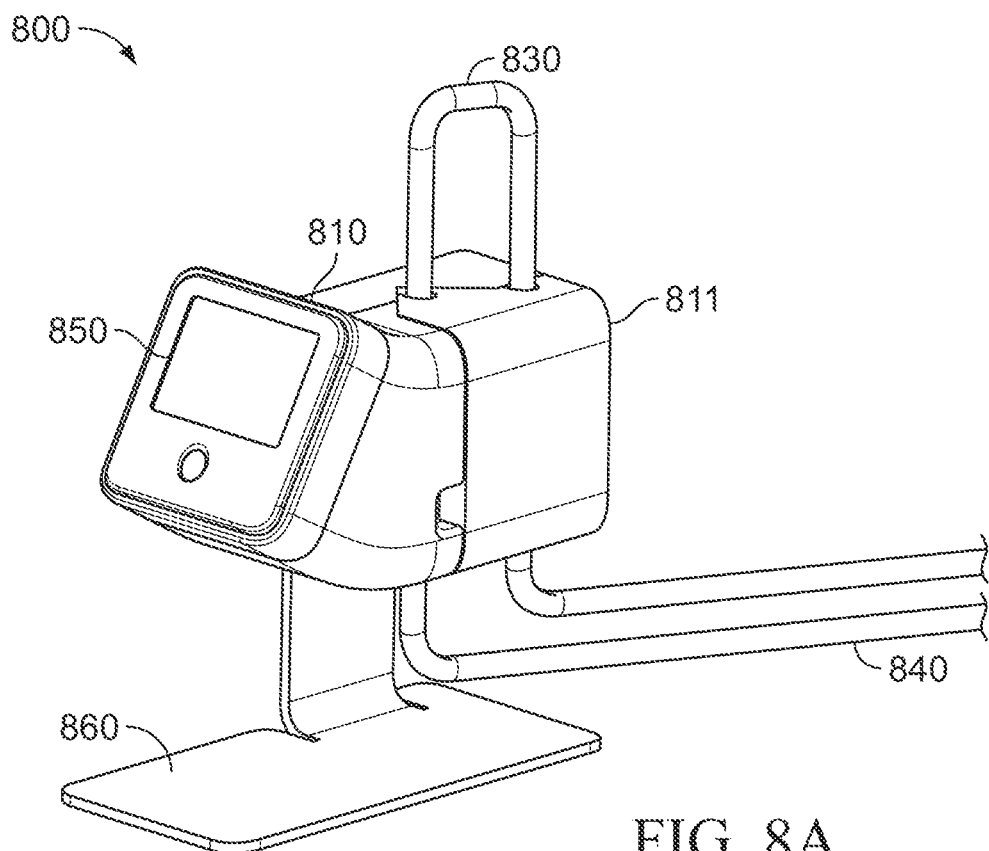
FIGS. 8A and 8D depict perspective views of an illustrative variation of a patient monitoring device in a closed configuration.
Figure 8B:
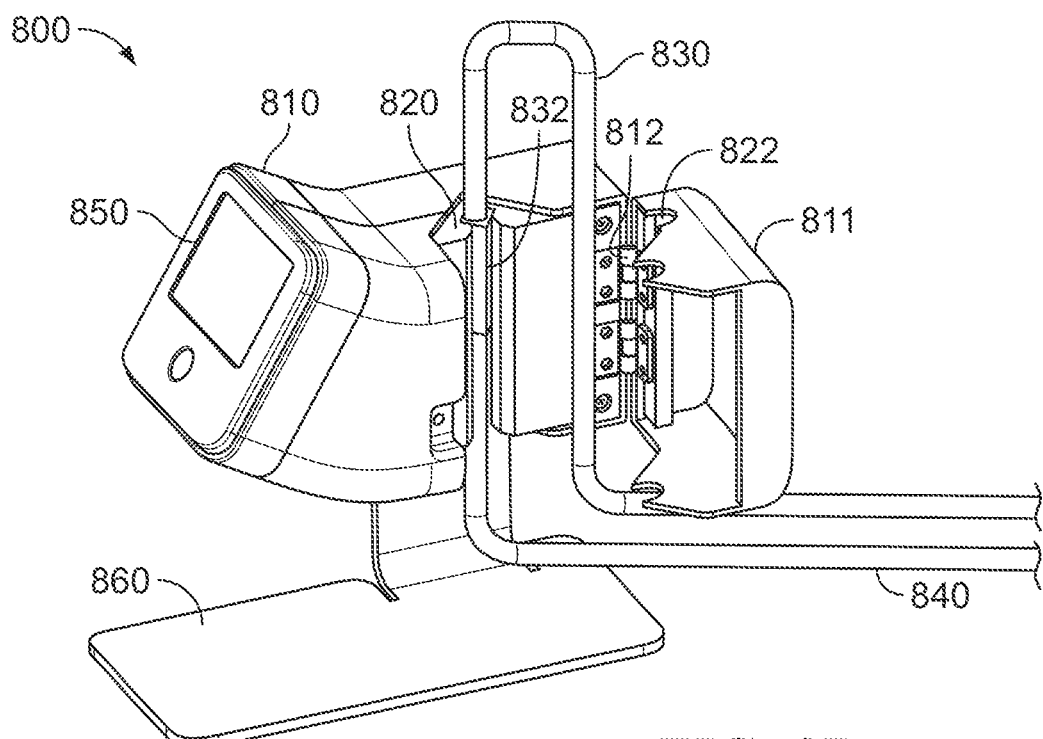
FIG. 8B depicts a perspective view of an illustrative variation of a patient monitoring device in an open configuration.

FIG. 7A depicts a semi-transparent perspective view of a patient monitoring device (700). FIG. 7B depicts an exploded schematic diagram of the patient monitoring device (700) comprising a housing (702) (e.g., enclosure), base (e.g., stand) (704), optical sensor arrangement (710), display (720), controller (730), communication device (740) (e.g., antenna, LTE or other cellular modem), and holder (750) (e.g., fluid conduit interface). The patient monitoring device (700) may be compact enough to fit on a table or nightstand. In some variations, the base (704) may elevate the housing (702) above a resting surface. That is, the housing (702) may be offset and spaced apart from the base (704). The spacing between the housing (702) and base (704) may, for example, allows sufficient room for one or more of a fluid conduit (e.g., drain line) and a disposable vessel (e.g., drainage bag) to be positioned underneath the housing (702) as shown in FIGS. 8A, 8B, and 9B. The offset may be, for example, between about 5 cm and about 30 cm.

Figure 7C:
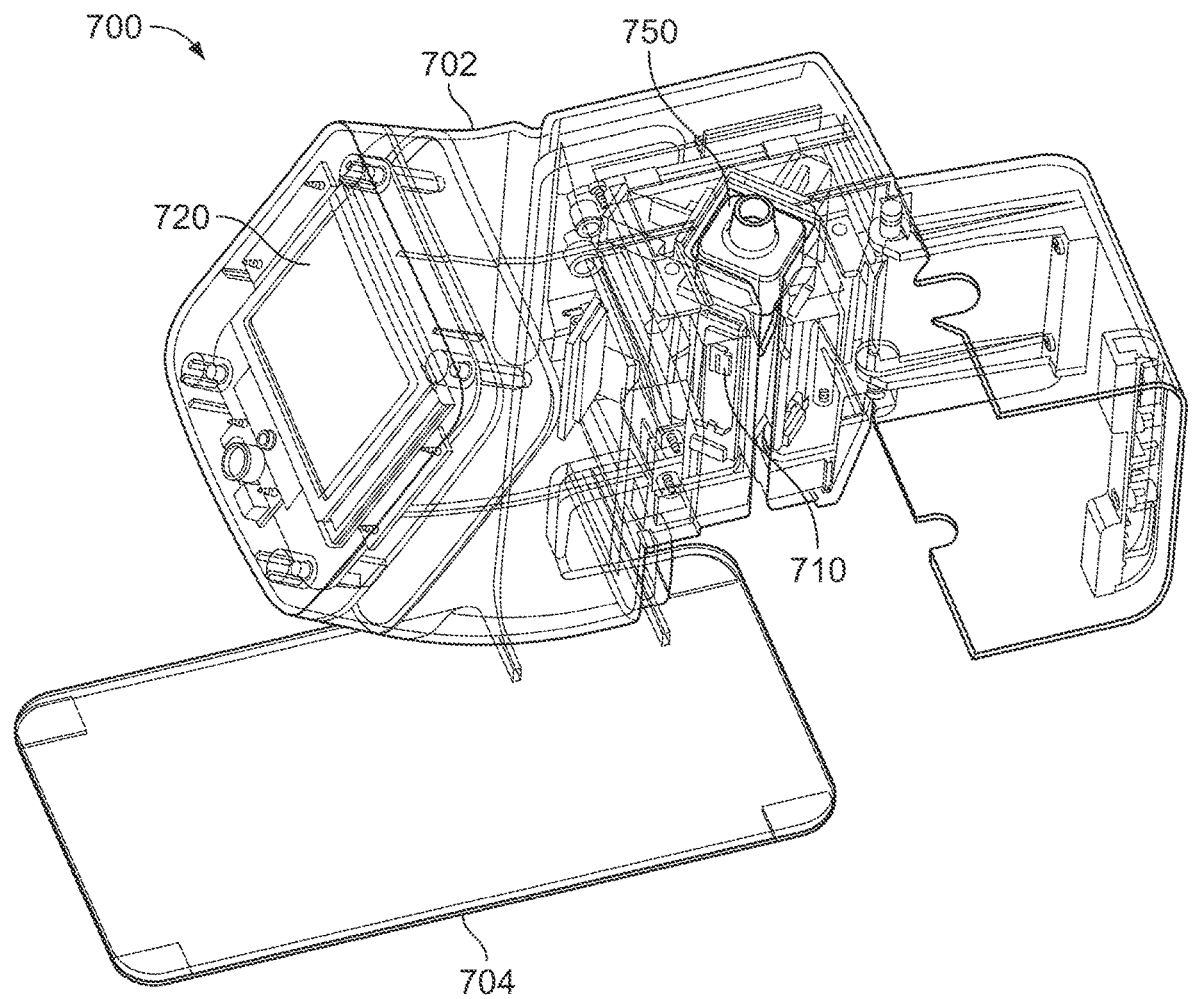
FIG. 7C depicts a perspective view of an illustrative variation of a patient monitoring device coupled to a vessel and in an open configuration.
Figure 7D:
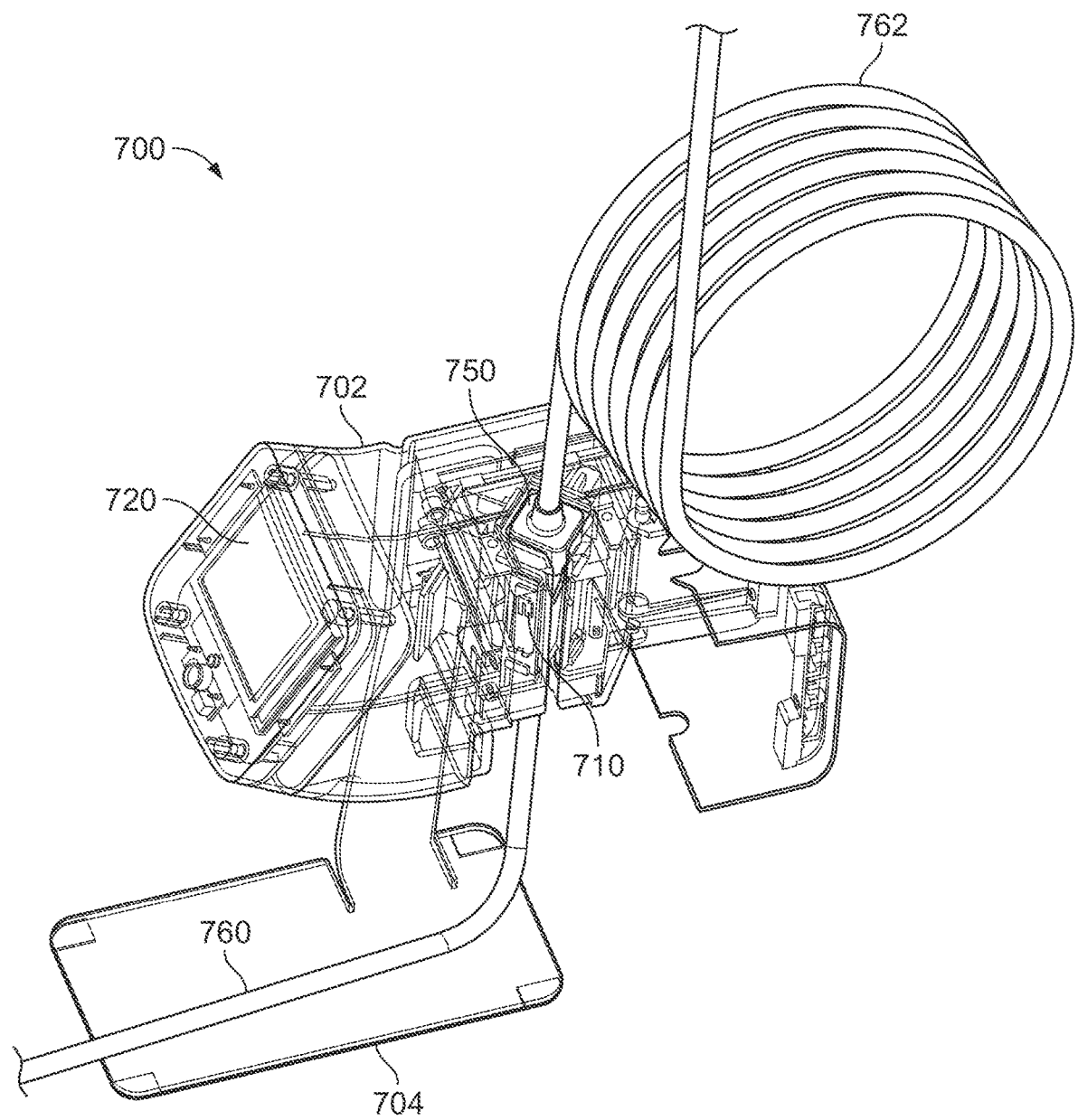
FIG. 7D depicts a perspective view of an illustrative variation of a patient monitoring device also in the open configuration. The patient monitoring device is coupled to a vessel attached to a fluid conduit.

FIGS. 7C and 7D depict a perspective view of the patient monitoring device (700) with the housing (702) in an open configuration. A vessel (750) is removeably held within the housing (702) and aligned to the optical sensor arrangement (710). FIG. 7D illustrates the vessel (750) coupled to a first fluid conduit (760) and a second fluid conduit (762) and FIG. 7C depicts the vessel (750) without the fluid conduit (760) for the sake of clarity. As described in more detail herein, the vessel (750) and housing (702) may comprise a set of mating features configured to orient relative rotation and/or depth of the vessel (750) and housing (702) to each other such that the vessel (750) may be inserted into the housing (702) in a single direction, depth, and orientation.

FIGS. 8A-8D depict various views of a variation of the patient monitoring device (800). The patient monitoring device (800) may comprise a housing (810), holder (820), display (850), and stand (860). A fluid conduit (830) may be fluidly coupled to an outlet of a cycler tubing set drain line (840). The fluid conduit (830) may be engaged to the holder (820), as described in more detail herein. As shown in FIG. 8B, the base (860) may be offset and spaced apart from the housing (810) to allow the fluid conduit (830) to be elevated relative to the drain line (840). For example, the fluid conduit (830) may be held substantially vertically to promote de-airing of the fluid conduit (830) during one or more of priming and fluid flow, thus reducing the presence of bubbles in an optical measurement portion of the fluid conduit (830) during measurement. In particular, the fluid conduit may be routed such that fluid is configured to flow in a low-to-high direction (i.e., generally upwards) that follows a direction of air buoyancy that promotes de-airing of the fluid conduit (830).

Figure 8D:
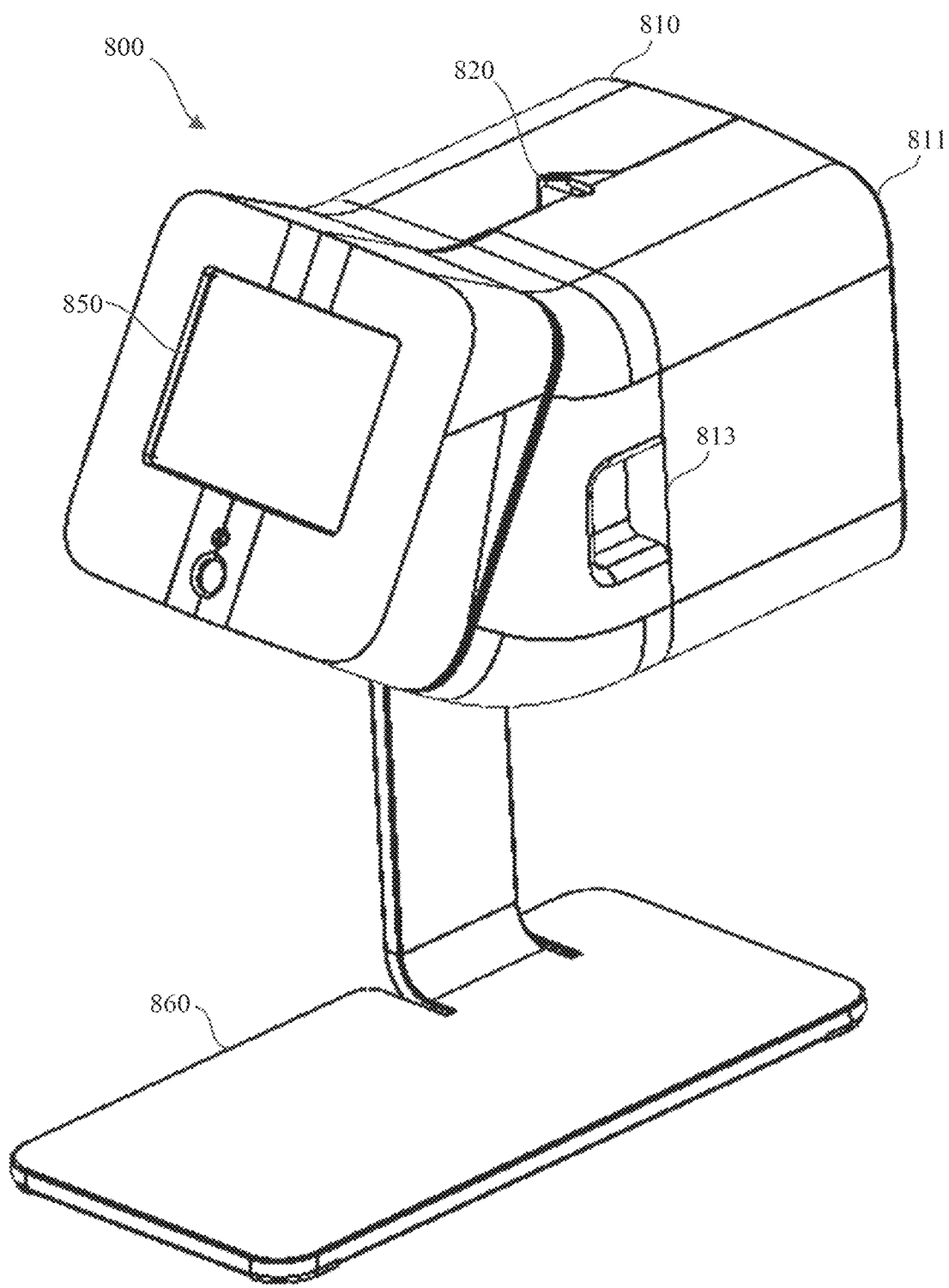

FIGS. 8A and 8D depict the patient monitoring device (800) in a light-shielding door closed configuration, and FIGS. 8B and 8C depict the patient monitoring device (800) in a light-shielding door open configuration. The housing (810) may be configured to transition between a door closed configuration (FIGS. 8A, 8D) and a door open configuration (FIGS. 8B, 8C). In the door closed configuration, the housing (810) and door (811) may form an ambient light seal configured to reduce ambient light penetration into an optical measurement region of the fluid conduit (830). In some variations, the housing (810) may further comprise a door (811) and a hinge (812) configured to open and close the housing (810). The door (811) in the closed configuration may form a top, bottom, and sidewall portion of the light seal. For example, the door (811) may enclose the outlet of a drain line (840) to form a bottom portion of the light seal that reduces ambient light penetration through the drain line (840). FIG. 8C is a side view of the patient monitoring device (800) in the door open configuration. The door (811) may be configured to enclose a portion of a cap (834) to form a top portion of the light seal. The door (811) may comprise an alignment feature where the door (811) may be configured to fully close only when the cap (834) is fully inserted and engaged in the holder (820). For example, in some variations, one or more alignment features in the door (811) and/or the vessel (832) or cap (834) may be arranged such that the door may fully close only if the vessel (832) and cap (834) are correctly oriented in a single predetermined orientation, thereby providing confirmation that the vessel and cap are in the correct orientation. Once the vessel (832) is engaged with the holder (820) in a predetermined orientation relative to the holder (820), the closed door (811) may prevent the cap (834) and vessel (832) from moving vertically (or being lifted out of the housing (810)), and the alignment features of the holder (820) will prevent the vessel (832) from being rotated, tilted, repositioned laterally, or pushed downward.

As shown in FIG. 8D, the door (811) may comprise a switch (e.g., latch, handle) (813) configured to allow a patient to open and securely close the door (811). For example, the switch (813) may comprise a spring-loaded mechanism and/or magnets. In some variations, the door (811) and/or other portion of the housing may comprise a sensor (e.g., Hall effect sensor, switch, contact sensor, optical-based sensor, etc.) configured to generate a door signal indicating an open/close state of the housing (810).

Figure 9A:
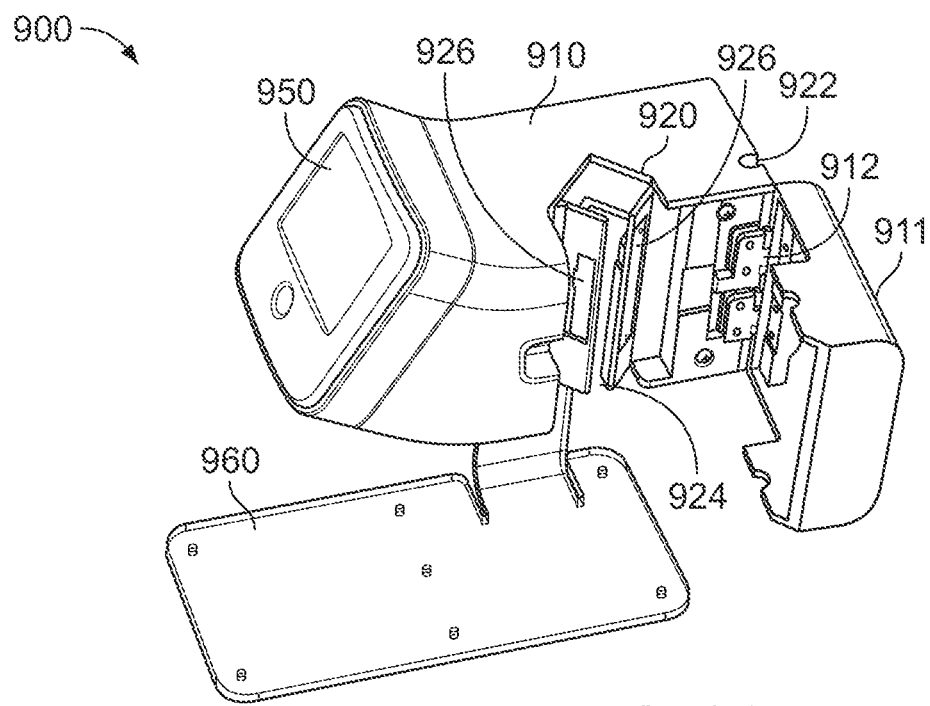
FIG. 9A depicts a perspective view of an illustrative variation of a patient monitoring device in an open configuration.
Figure 9B:
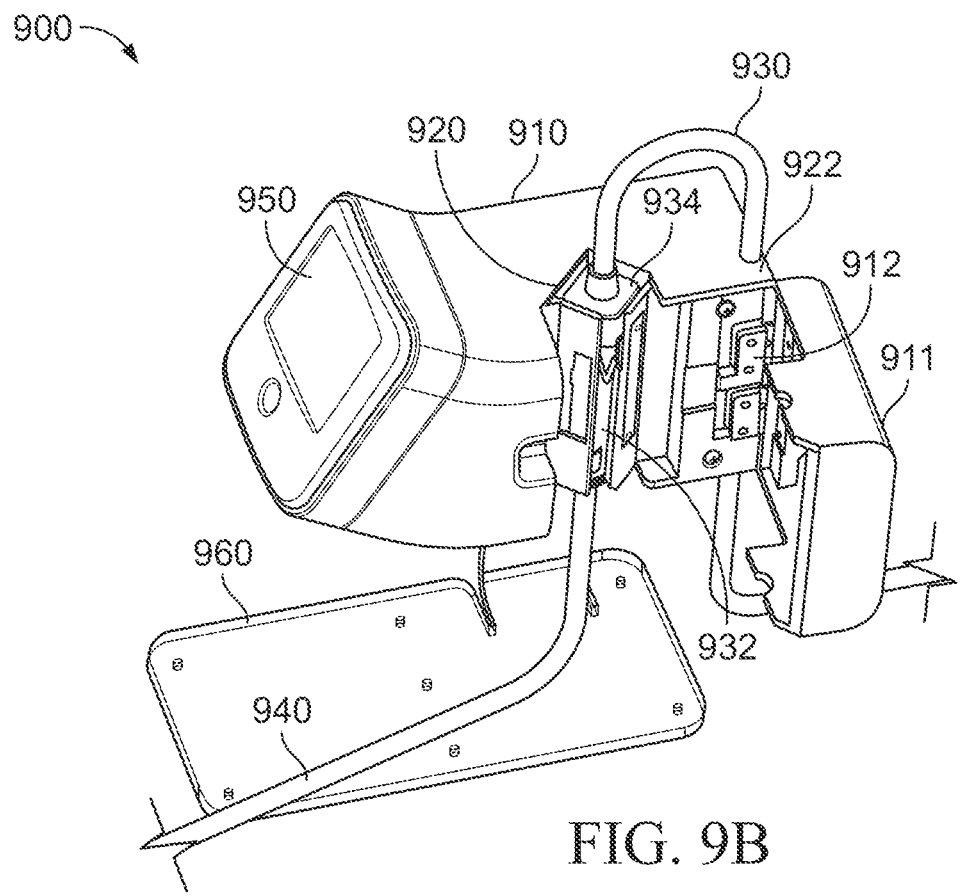
FIG. 9B depicts a perspective view of an illustrative variation of a fluid conduit and a patient monitoring device in an open configuration.
Figure 9C:
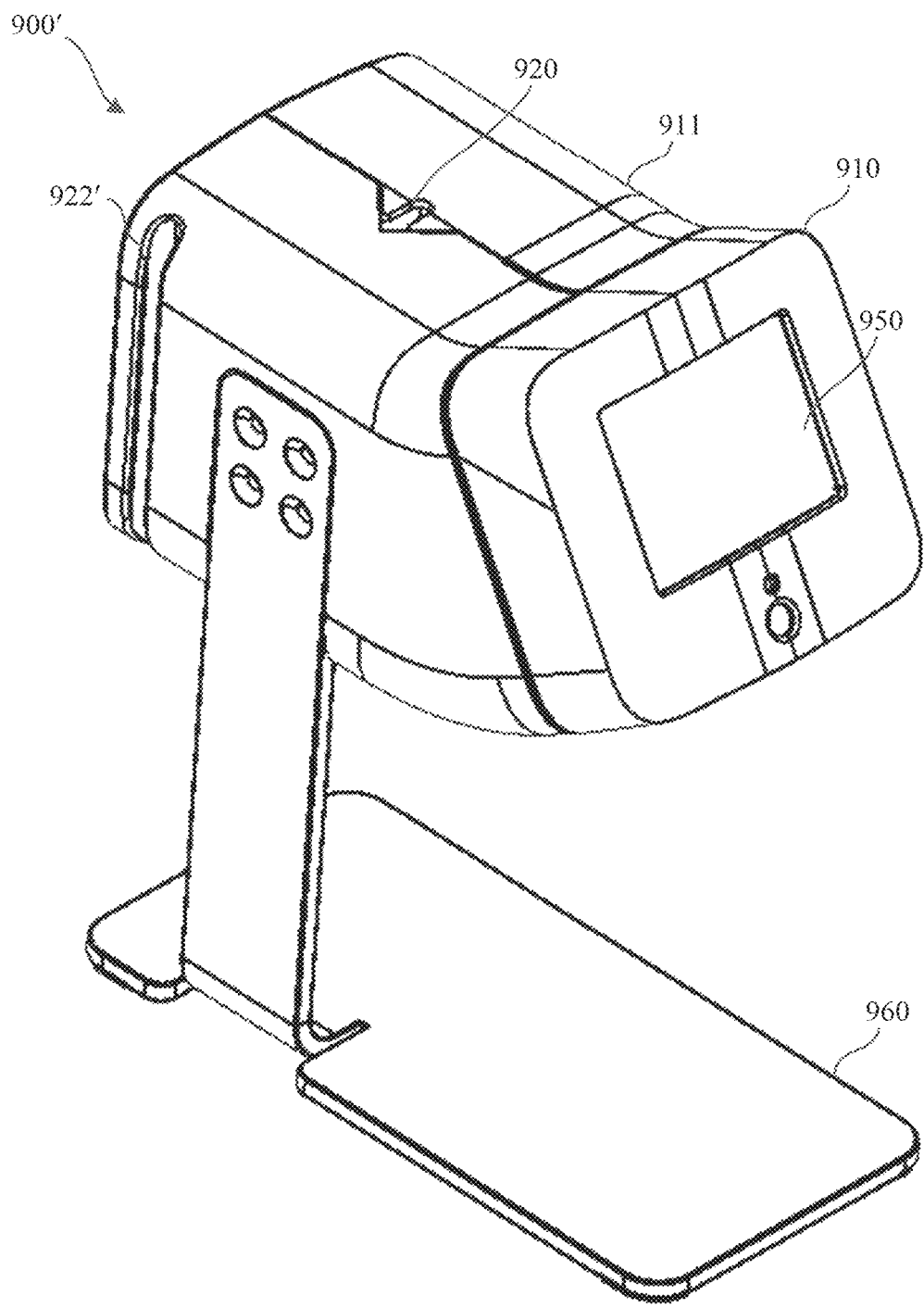
FIG. 9C depicts a perspective view

FIGS. 9A-9C depict various views of a patient monitoring device (900). The patient monitoring device (900) may comprise a housing (910), door (911), hinge (912), holder (920), slot (924), optical sensor (926), display (950), and stand (960). A fluid conduit (930) may be fluidly coupled to the outlet of a drain line (940), as shown in FIG. 9B. The fluid conduit (930) may comprise a vessel (932) and a cap (934). FIGS. 9A and 9B depict the patient monitoring device (900) in an open configuration. FIG. 9C depicts a patient monitoring device (900') similar to the device (900) shown in FIGS. 9A and 9B except for the location of tubing routing portion (922'). Patient monitoring device (900') is shown in a closed configuration.

Figure 10A:
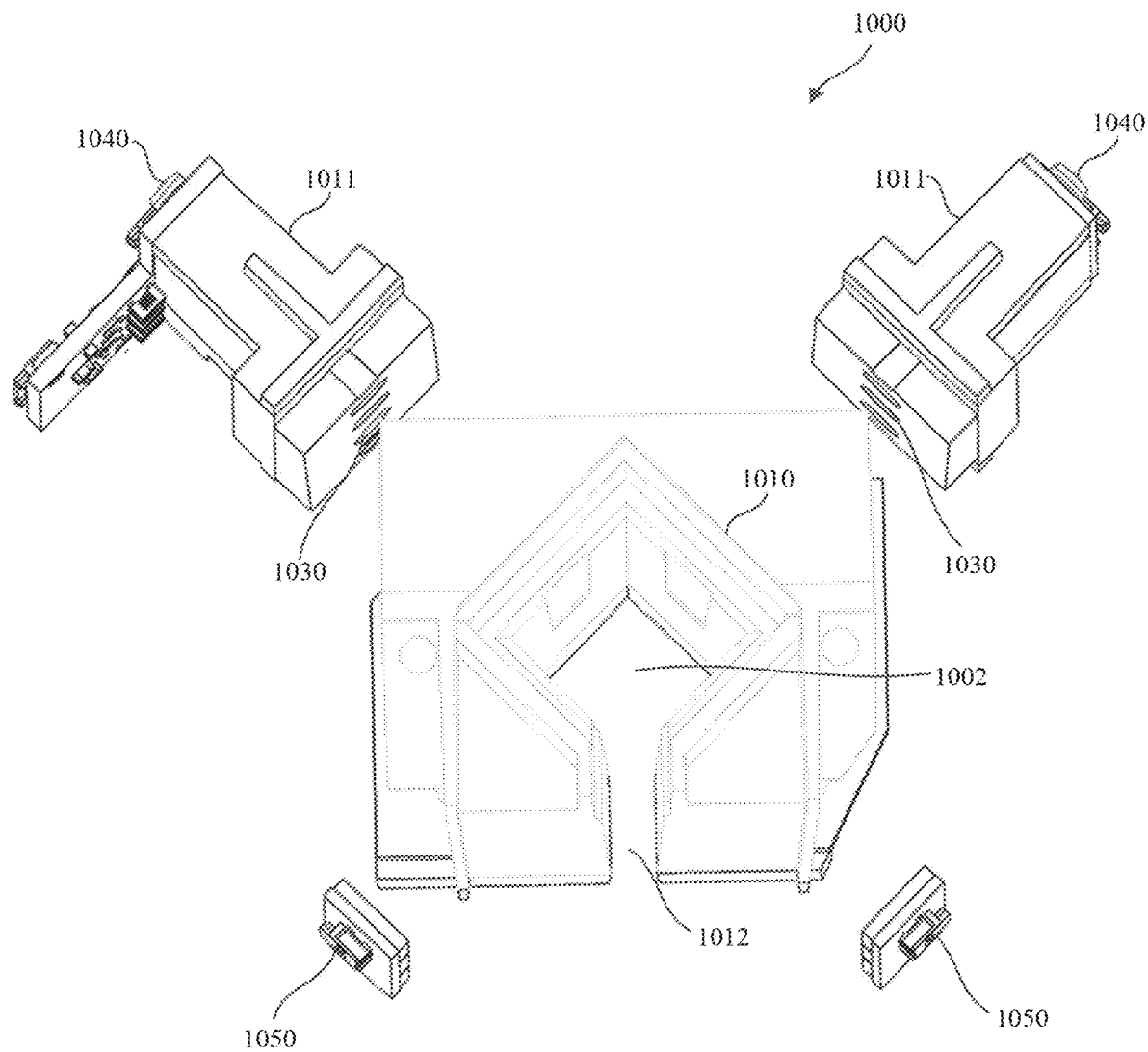
FIG. 10A is an exploded perspective view of an illustrative variation of a holder of a patient monitoring device.
Figure 10B:
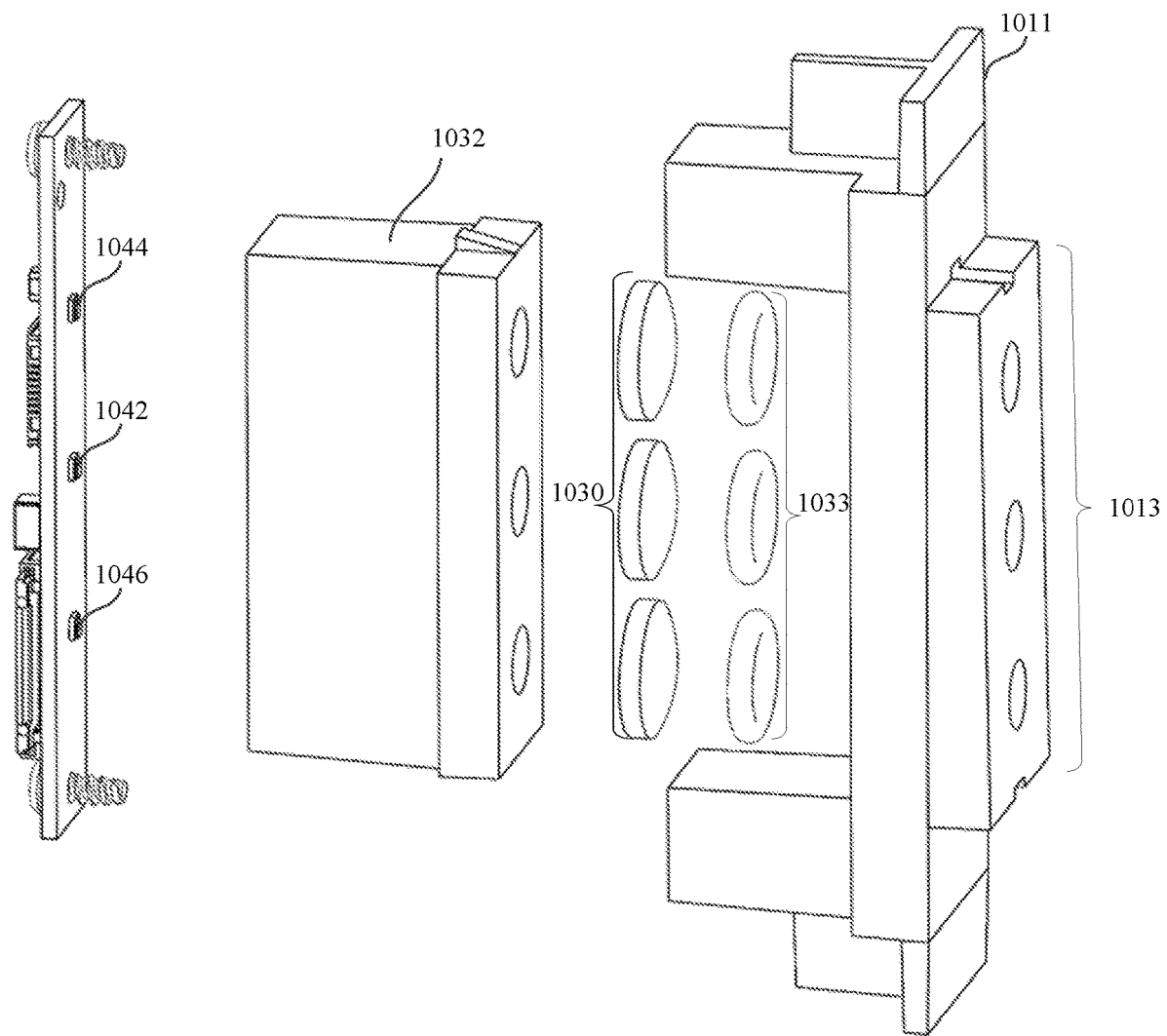
FIG. 10B is an exploded perspective view of an illustrative variation of an optical sensor arrangement of a patient monitoring device.
Figure 10C:
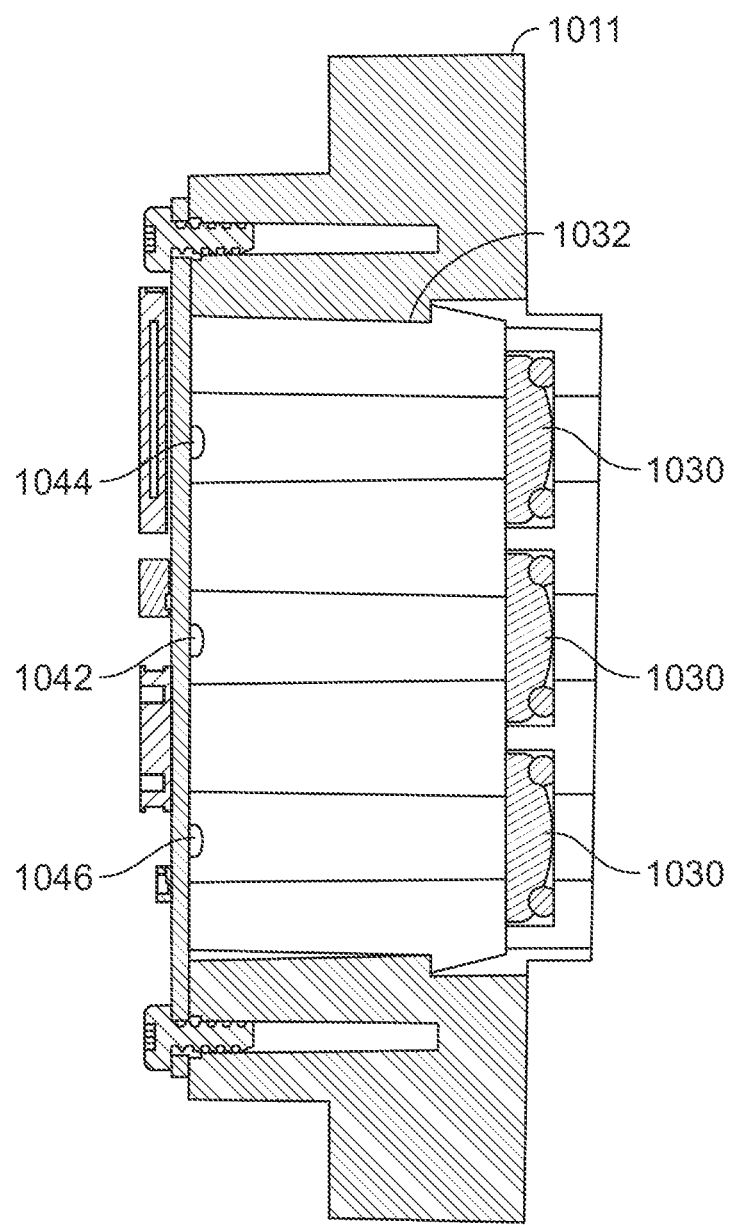
FIG. 10C is a cross-sectional schematic view of an illustrative variation of an optical sensor arrangement of a patient monitoring device.
Figure 10D:
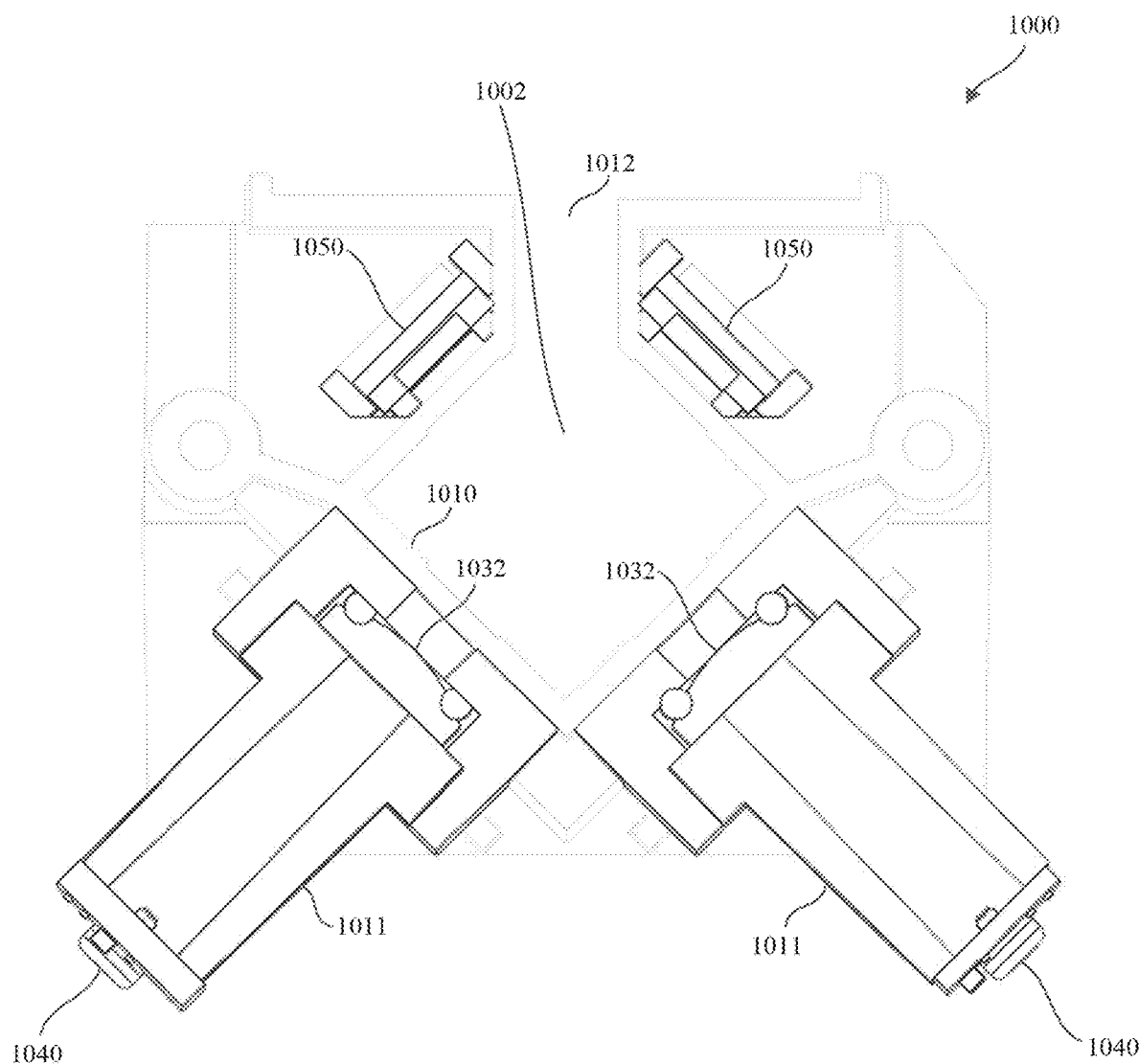
FIG. 10D is a plan view of an illustrative variation of a holder of a patient monitoring device.
Figure 10E:
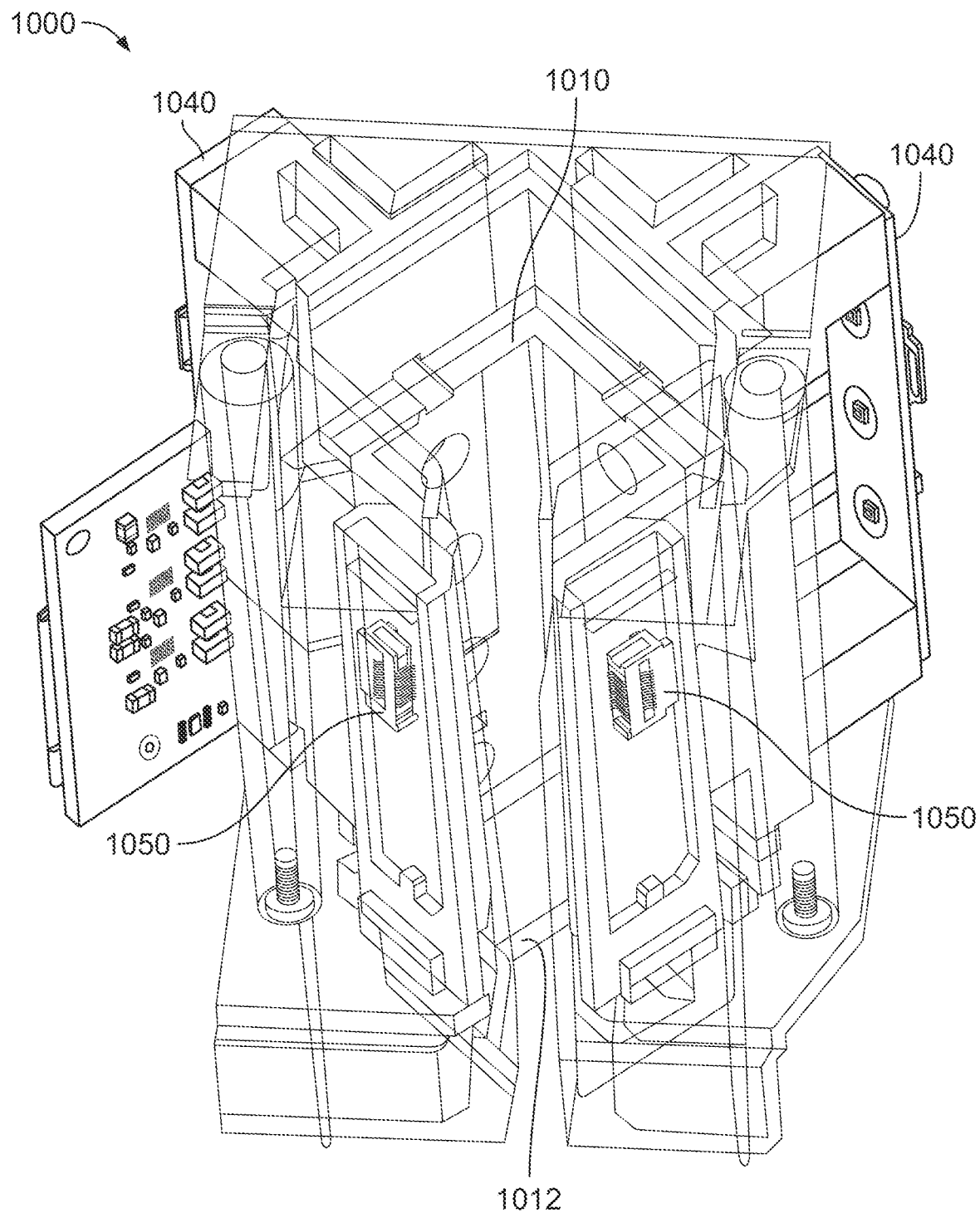
FIG. 10E is a perspective view of an illustrative variation of a holder of a patient monitoring device.

FIGS. 10A and 10E are perspective views of a holder (1010) of a patient monitoring device (1000) configured to receive and engage a portion of a fluid conduit (e.g., vessel) (not shown for the sake of clarity) in a predetermined orientation relative to at least one set of illumination sources (1040) and at least one set of optical sensors (1050). The illumination sources (1040) may be configured to illuminate the received portion of the fluid conduit and the optical sensors (1050) may be configured to generate a signal such as an optical characteristic measurement based on illuminated patient fluid. FIGS. 10B and 10C illustrate an optical sensor arrangement comprising an illumination housing (1011), collimator (1032), lens (1030) (e.g., aspherical lens), lens-locating O-rings (1033), and illumination sources (1042, 1044, 1046). The illumination housing (1011) may define a set of apertures (1013).

The holder (1010) may define a cavity (1002) having a generally rectangular (e.g., square) cross-sectional shape configured to receive a portion of the fluid conduit having a generally rectangular (e.g., square) cross-sectional shape. The holder (1010) may further define an engagement feature (1012) (e.g., slot, slit) configured to orient the received portion of the fluid conduit in a predetermined rotational orientation relative to the illumination source (1040) and optical sensor (1050). For example, the engagement feature (1012) may define an open slot that may extend along a longitudinal axis of the holder (1010) (see FIG. 10E) and located at an edge of the generally rectangular cross-sectional shape. The slot may allow one or more of the vessel, fluid conduit, and drain line to be assembled and removed from the holder (1010) without disconnecting any of the drain line components. The engagement feature (1012) may encourage or ensure one-way insertion of the fluid conduit into the holder (1010). In some variations, as further described herein, the holder (1010) may additionally or alternatively comprise a second engagement feature (e.g., shoulder, lip, protrusion, etc.) configured to orient the received portion of the fluid conduit at a predetermined at a depth position relative to the illumination source (1040) and optical sensor (1050).

Figure 26:
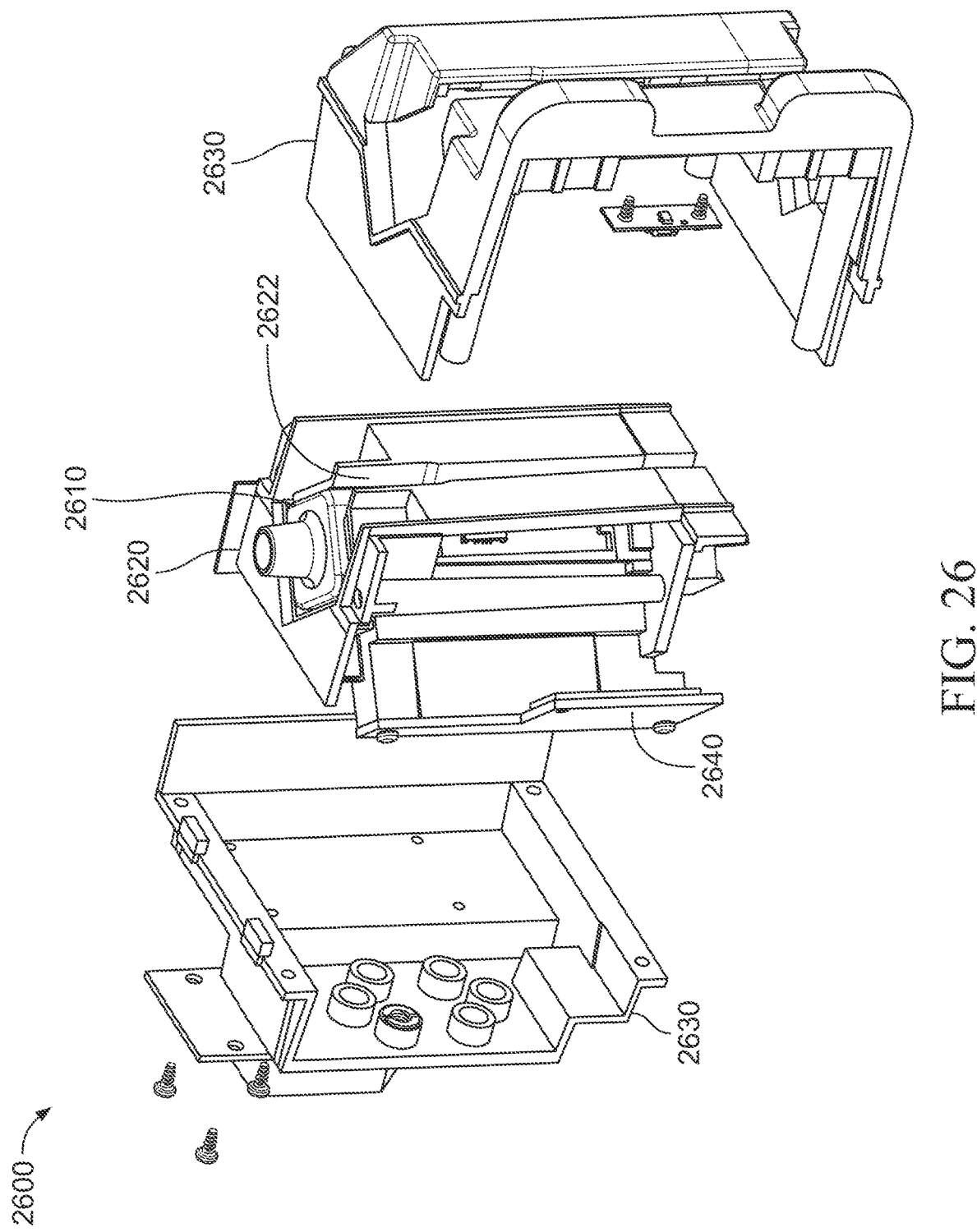
FIG. 26 is an exploded perspective view of an illustrative variation of a vessel disposed in a holder of a patient monitoring device.

FIG. 26 is an exploded perspective view of a vessel (2610) disposed in a holder (2620) of a patient monitoring device (2600). The holder (2620) may comprise an engagement portion (2622) such as a slot that extends along a longitudinal axis of the holder (2620). The holder (2620) may be configured to couple to one or more portions of a housing (2630) of the patient monitoring device (2600). An optical sensor arrangement (2640) may be coupled to the holder (2620). To remove the vessel (2610) from the holder (2620), a CCPD tubing set including a drain line and/or fluid conduit (not shown) coupled to the vessel (2610) may be lifted up from the holder (2620) and moved laterally through the slot (2622) without disconnecting any component of the tubing set.

Figures 12A, 12B:
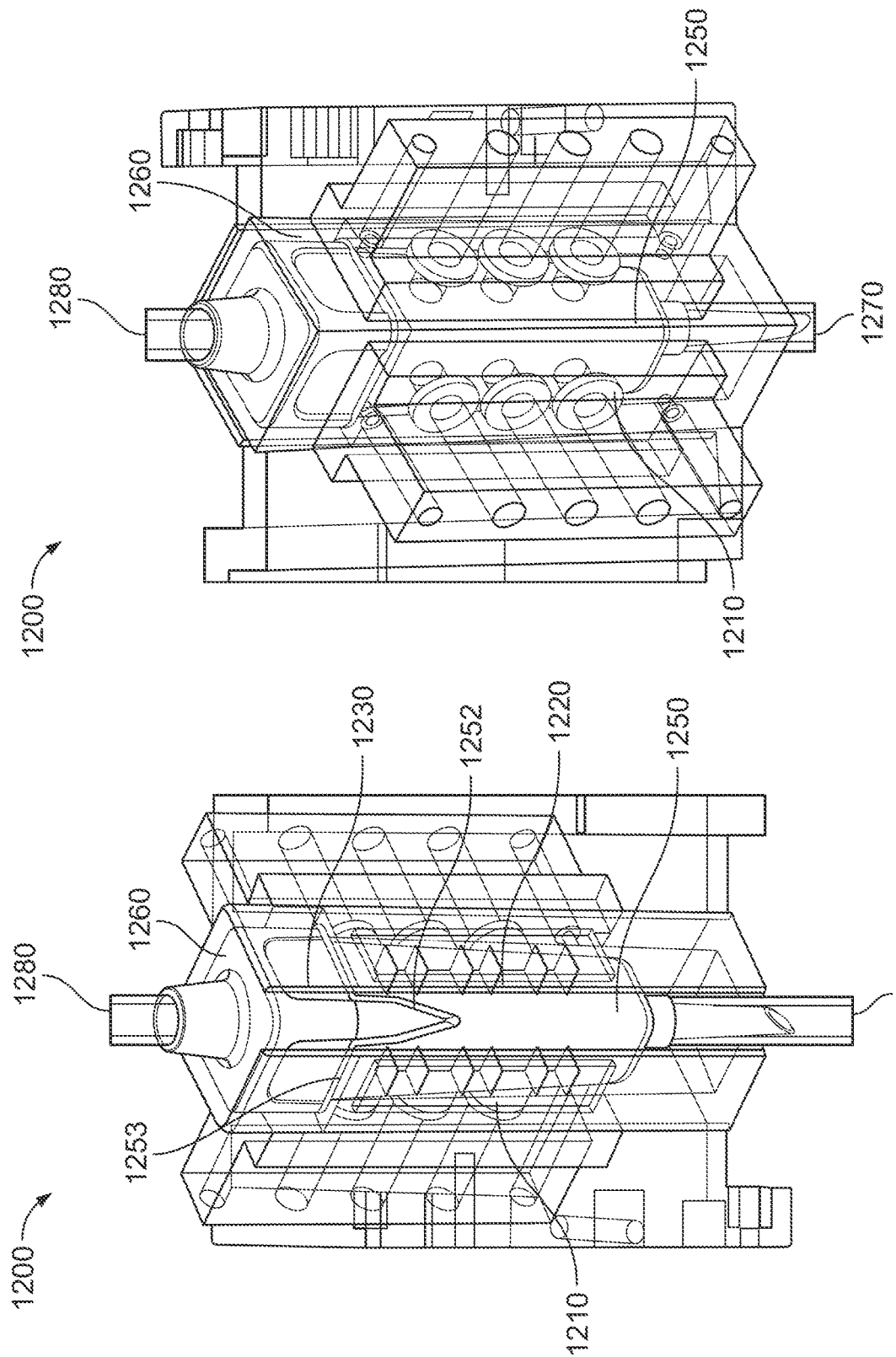
FIGS. 12A and 12B are schematic perspective views of an illustrative variation of a vessel and an optical sensor arrangement of a patient monitoring device.

As shown in the perspective views of FIGS. 12A and 12B, a holder (1200) may be configured to releasably receive a portion of a vessel (1250). The vessel (1250) may comprise a rotational alignment feature (1252) configured to engage an engagement feature (1230) (e.g., slot, slit) of the holder (1200) such that the vessel (1250) is secured and rotationally aligned to the holder (1200) in a single position. For example, the engagement feature (1230) may be configured to orient the received portion of the fluid conduit (1250) by mating with the alignment feature (1252) of the received portion of the fluid conduit (1250). Additionally or alternatively, the vessel (1250) may comprise a depth alignment feature configured to engage a second engagement feature such that the vessel (1250) is positioned a predetermined depth, as described in further detail below.

For example, in some variations, the alignment feature (1252) may comprise a protrusion having a shape configured to form an interference fit with the engagement feature (1230) of the holder (1200). The alignment feature (1252) may comprise a taper that allows the vessel (1250) to slide and/or self-align into the engagement feature (1230). FIG. 12B is a perspective view of the holder (1200) and vessel (1250) from a vantage point opposite that of FIG. 12A. The sidewalls of the holder (1200) shown in the foreground of FIG. 12B do not comprise a corresponding engagement feature (1230). Therefore, the shape of the vessel (1250), alignment feature (1252), holder (1200), and engagement feature (1230) encourages the patient to insert and rotationally align the vessel (1250) in a single orientation such that the vessel (1250) may be aligned to the illumination sources (1210) and optical sensors (1220).

In some variations, the alignment feature (1252) may further comprise a depth alignment feature such as a set of one or more shoulders (1253) (e.g., lip, protrusions) configured to contact the sidewalls of the holder (1200) and aid depth alignment of the vessel (1250) to the holder (1200). The shoulders (1253) may be disposed at least widthwise along one or more sidewalls of the vessel (1250). The holder (1200) may be configured to provide a light seal around the vessel (1250) except for the open top portion, open bottom portion, and open portion of the engagement feature (1230). For example, the holder (1200) may comprise an opaque gasket or other seal that substantially blocks ambient light. A door of the patient monitoring device and light seal features of the vessel (1253) may further contribute to sealing the vessel (1250) from ambient light.

In some variations, the patient monitoring device may comprise a set of one or more fluid conduit routing features configured to aid optical measurement of the fluid conduits. As shown in FIG. 8A, the outlet of a drain line (840) may be routed beneath the housing (810) such that a portion of the fluid conduit (830) is held substantially orthogonal to the base (860). In some variations, a portion of the fluid conduit (830) distal to the vessel (832) may form a loop above or around the housing (810) and be releasably coupled to a routing portion (822) configured to provide strain relief, reduce downstream kinking of the fluid conduit (830), and/or reduce blockages in the fluid conduit (830).

In FIGS. 8B and 8C, the routing portion (822) may comprise a channel of the housing (810) through which the fluid conduit (830) may be held. In FIGS. 9B and 9C, the routing portion (922) may define an external slot configured to releasably couple to the fluid conduit (930). For example, a portion of the fluid conduit (930) may be slid or clipped into the routing portion (922). The routing portion (922) may be provided on any suitable side of the housing (910). For example, as shown in FIG. 9B, the routing portion (922) may be along a rear side of the housing, while as shown in FIG. 9C, the routing portion (922') may be along a lateral side of the housing.

In some variations, the routing portion may further comprise one or more fastening features to laterally, axially, and/or rotationally fix (or otherwise secure) the fluid conduit into the routing portion. For example, a routing portion may comprise a channel that is sized to receive the fluid conduit with an interference fit (e.g., snap fit). As another example, a routing portion may include one or more fastening devices (e.g., clip, snap, band, etc.) to secure the fluid conduit in the channel. Similarly, a routing portion may include a channel having one or more loops or other structure spanning the slot (or other lattice) through which the fluid conduit may be fed into the channel. As another example, a routing portion may include a channel having texturing (e.g., bumps, rings) along its surface to increase friction between the channel and the fluid conduit. As another example, adhesive on the channel and/or fluid conduit may be used to mount the fluid conduit within the channel. Any of the above-described examples of fastening features may be combined in any suitable manner.

In some variations, the patient monitoring device may comprise an optical sensor arrangement configured to illuminate patient fluid and measure optical characteristics of the patient fluid. For example, the optical sensor arrangement may comprise an illumination source and an optical sensor. In some variations, sets of illumination sources and optical sensors may be arranged in parallel and configured to measure optical characteristics of different regions of a vessel. Non-limiting examples of an illumination source (e.g., light source) include incandescent, electric discharge (e.g., excimer lamp, fluorescent lamp, electrical gas-discharge lamp, plasma lamp, etc.), electroluminescence (e.g., light-emitting diodes, organic light-emitting diodes, laser, etc.), induction lighting, and fiber optics. In some variations, the optical sensor may comprise a photodiode, charged coupled device (CCD) or complementary metal-oxide semiconductor (CMOS) optical sensor.

Figure 14A:
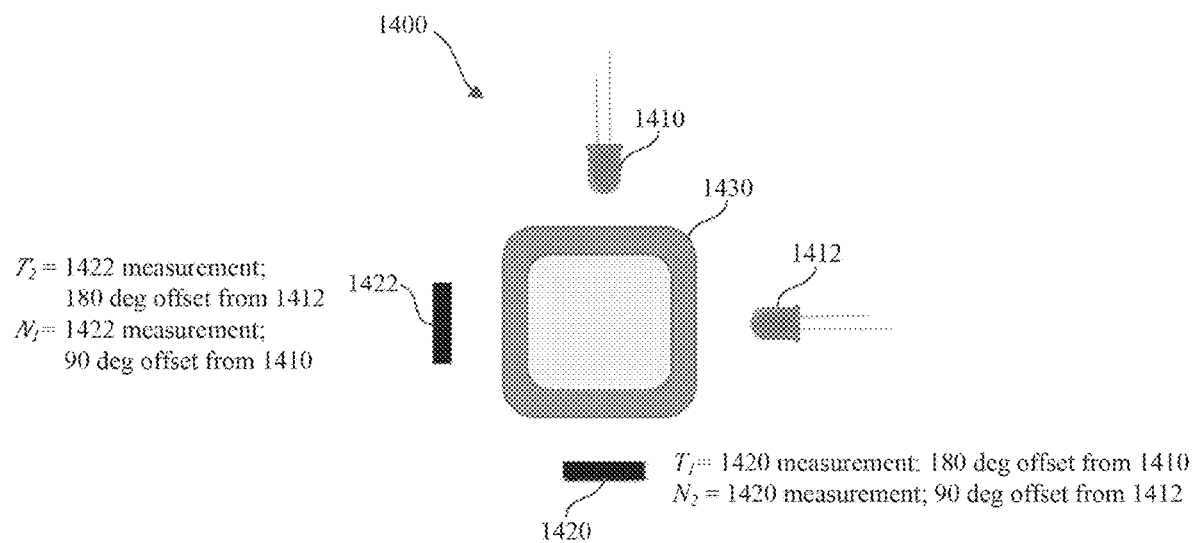
FIGS. 14A and 14B are schematic diagrams of illustrative variations of an optical sensor arrangement.
Figure 14B:
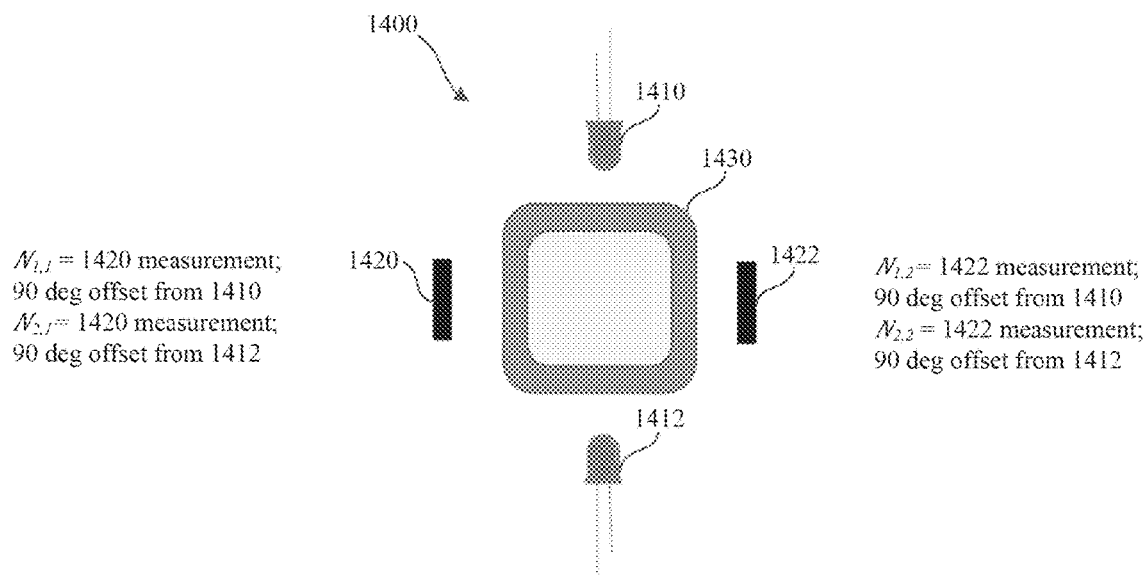

FIGS. 14A and 14B are schematic diagrams of a cross-section (e.g., single planar arrangement) of an optical sensor arrangement. The optical sensor arrangement may provide for illumination from a plurality of illumination directions. As shown in FIG. 14A, a first illumination source (1410) may illuminate a vessel (1430) in a first illumination direction and a second illumination source (1412) may illuminate the vessel (1430) in a second illumination direction orthogonal to the first illumination direction. In another example shown in FIG. 14B, the first illumination source (1410) may have a first illumination direction that is 180 degree offset from the second illumination direction such that the illumination sources may direct light in opposite directions. In some variations, the patient fluid may be illuminated from a plurality of non-parallel illumination directions. For example, the first illumination direction may have an offset from the second illumination direction of between more than about 0 degrees and about 180 degrees. In some variations, the first illumination source (1410) and the second illumination source (1412) may be configured to provide illumination at the same wavelength.

In FIGS. 14A and 14B, a first optical sensor (1420) and a second optical sensor (1422) may be configured to generate a signal corresponding to measurement of an optical characteristic of the illuminated patient fluid. The first and second optical sensors may, for example, be photodiodes. An optical sensor may be configured to measure one or more of optical scatter and attenuation detection angle (e.g., absorption, obscuration). For example, the optical sensors may be configured to measure a property of illuminated patient fluid at an attenuation/obscuration angle (about 180 degrees), forward scattering angles (about >90 degrees about <180 degrees), side scattering angle (about 90 degrees), and back-scattering angles (about <90 degrees, about ≥0 degrees). In FIG. 14A, the first optical sensor (1420) faces the first illumination source (1410) (the first optical sensor and the first illumination source are on opposite sides of the vessel (1430)), and the second optical sensor (1422) faces the second illumination source (1412) (the second optical sensor and the second illumination source are on opposite sides of the vessel (1430)). In FIG. 14B, the first optical sensor (1420) is generally orthogonal to the first illumination source (1410), and the second optical sensor (1422) is generally orthogonal to the second illumination source (1412).

In some variations, an optical sensor arrangement may comprise a plurality of planar arrangements such as that shown in FIGS. 14A and 14B. For example, as shown in FIGS. 10D and 10E, a plurality of illumination sources (1040) and optical sensors (1050) may be coupled to the holder (1010). The holder (1010) may be coupled to three planar arrangements of illumination sources and optical sensors. In some variations, the planar sets may be spaced apart and parallel to a longitudinal axis of the holder (1010). In some variations, the illumination sources (1040) may be configured to output the same or different wavelengths. For example, two or more illumination sources (1040) may be configured to output the same wavelengths to provide redundancy and improve the accuracy of the optical measurements. As another example, two or more illumination sources (1040) may be configured to output different wavelengths, where measurements associated with different wavelengths may provide different information (e.g., may allow identification of different particle types associated with each respective wavelength).

Figure 10F:
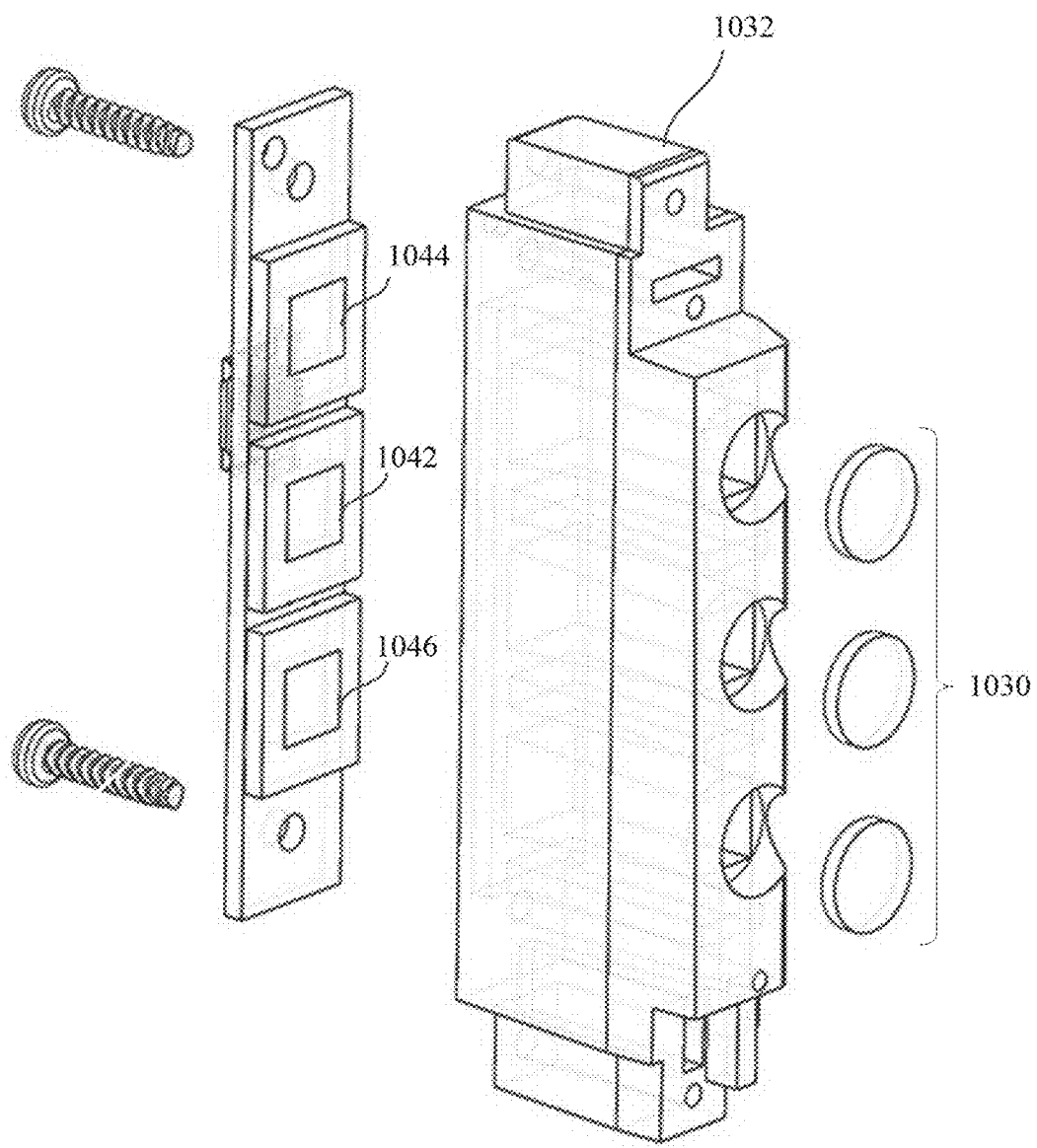
FIG. 10F is an exploded perspective view of an illustrative variation of an optical sensor arrangement of a patient monitoring device.

FIG. 10F illustrates an optical sensor arrangement comprising a collimator (1032), at least one lens (1030) (e.g., aspherical lens), and illumination sources (1042, 1044, 1046). In some variations, an illumination source (1042, 1044, 1046) and/or collimator (1032) may be configured to minimize stray light received by the optical sensor arrangement. For example, one or more of an illumination source and the optical sensor arrangement (e.g., collimator) may comprise one or more of an anti-reflective coating and light trap. For any of the optical sensor arrangements described herein, the aperture may additionally or alternatively be configured to allow a predetermined range of viewing angles of the optical sensor arrangement.

As shown in FIG. 10C, a first illumination source (1042) may be configured to emit light at a first wavelength between about 800 nm and about 900 nm (e.g., about 860 nm). A second illumination source (1044) may be configured to emit light at a second wavelength between about 400 nm and about 450 nm (e.g., about 405 nm). A third illumination source (1046) may be configured to emit light at a third wavelength between about 500 nm and about 550 nm (e.g., about 525 nm). The first illumination source (1042) may be placed in a generally central location, furthest away from any potential sources of ambient light leakage (e.g., from the inlet and outlet of the vessel). The second illumination source (1044) may be placed nearest to an outlet of the vessel to minimize alterations to the patient fluid due to the illumination at the second wavelength (e.g., UV light). Additionally or alternatively, two of the illumination sources may be configured to output illumination at the same wavelength. In some variations, a fourth illumination source (not shown) may be configured to emit light at a fourth wavelength between about 230 nm and about 290 nm.

In some variations, the illumination source may comprise one or more of a light emitting diode (and/or laser, scintillator or other light source), collimator, and lens. The illumination source may, in some variations, further include one or more filters. In some variations, one or more components, such as the collimator, may include an anti-reflective coating and/or other suitable feature to minimize stray light output from the illumination source. At least some of these components may be arranged relative to each other via a mounting block or other fixture. For example, the illumination source may comprise a convex-plano lens configured to collimate the illumination and a set of filters configured to narrow a wavelength range. FIGS. 10B and 10C illustrate an illumination housing (1011) comprising a lens (1030) and collimator (1032).

In some variations, the lens (1030) may comprise a convex-plano or aspherical lens. In some variations, each illumination source of each planar arrangement may have a respective set of at least a collimator and a lens.

Figure 11A:
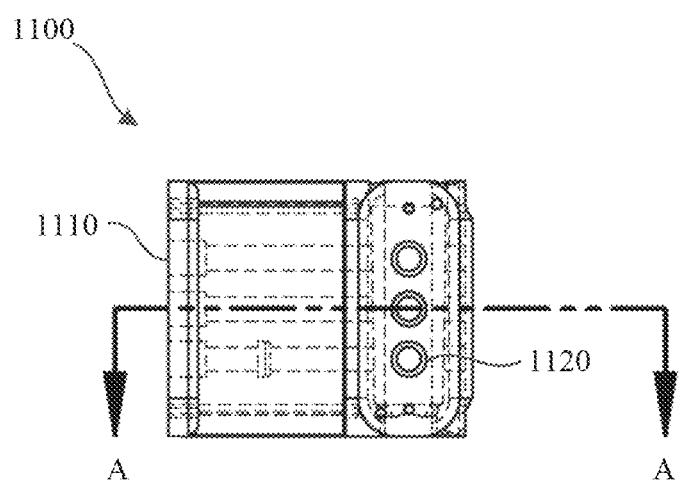
FIG. 11A is a side view of an illustrative variation of an optical sensor arrangement of a patient monitoring device.
Figure 11B:
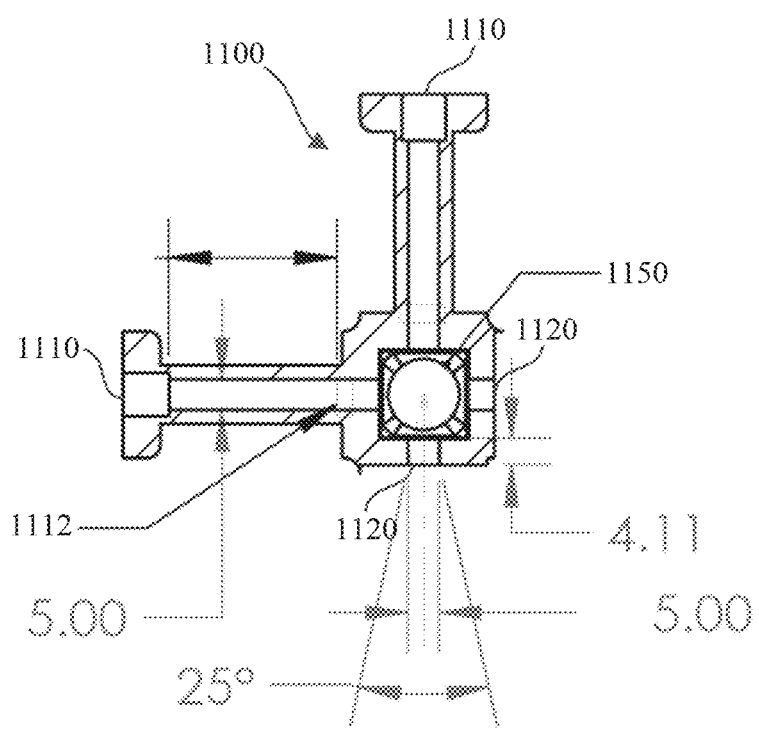
FIG. 11B is a cross-sectional view of the optical sensor arrangement depicted in FIG. 11A, taken along line A:A.

FIG. 11A is a side view of an optical sensor arrangement (1100) of a patient monitoring device comprising a set of substantially orthogonal illumination sources (1110) and corresponding optical sensors (1120). The illumination sources (1110) are orthogonal to the optical sensors (1120). FIG. 11A depicts a pair of orthogonal illumination sources (1110) and a pair of orthogonal optical sensors (1120) on each of three substantially parallel cross-sectional planes. The optical sensor arrangement (1100) may comprise a lens (1112). A vessel (1150) may be aligned to the optical sensor arrangement (1100) so as to receive illumination from the illumination source (1110). FIG. 11B is a cross-sectional view one plane of the optical sensor arrangement (1100) depicted in FIG. 11A along the A-A line having exemplary dimensions. For example, the illumination source (1110) may have width of about 5 mm. A lens (1112) may have a thickness of about 10 mm. The optical sensor (1120) may have an aperture of about 5 mm with an aperture distance of about 4 mm (e.g., 4.11 mm). However, the optical sensor arrangement may include other suitable dimensions.

In some variations, an optical sensor arrangement may comprise at least one illumination source configured to emit white light at a wide spectrum (e.g., between about 200 nm and about 1400 nm) and/or emit light in different wavelength ranges. For example, the illumination source may comprise an RGB light emitting diode. The optical sensor arrangement may further comprise at least one optical sensor configured to measure optical characteristics of illuminated patient fluid. For example, the optical sensor may comprise a spectrophotometer to measure absorbance or scatter across a wide range of wavelengths.

Figure 13:
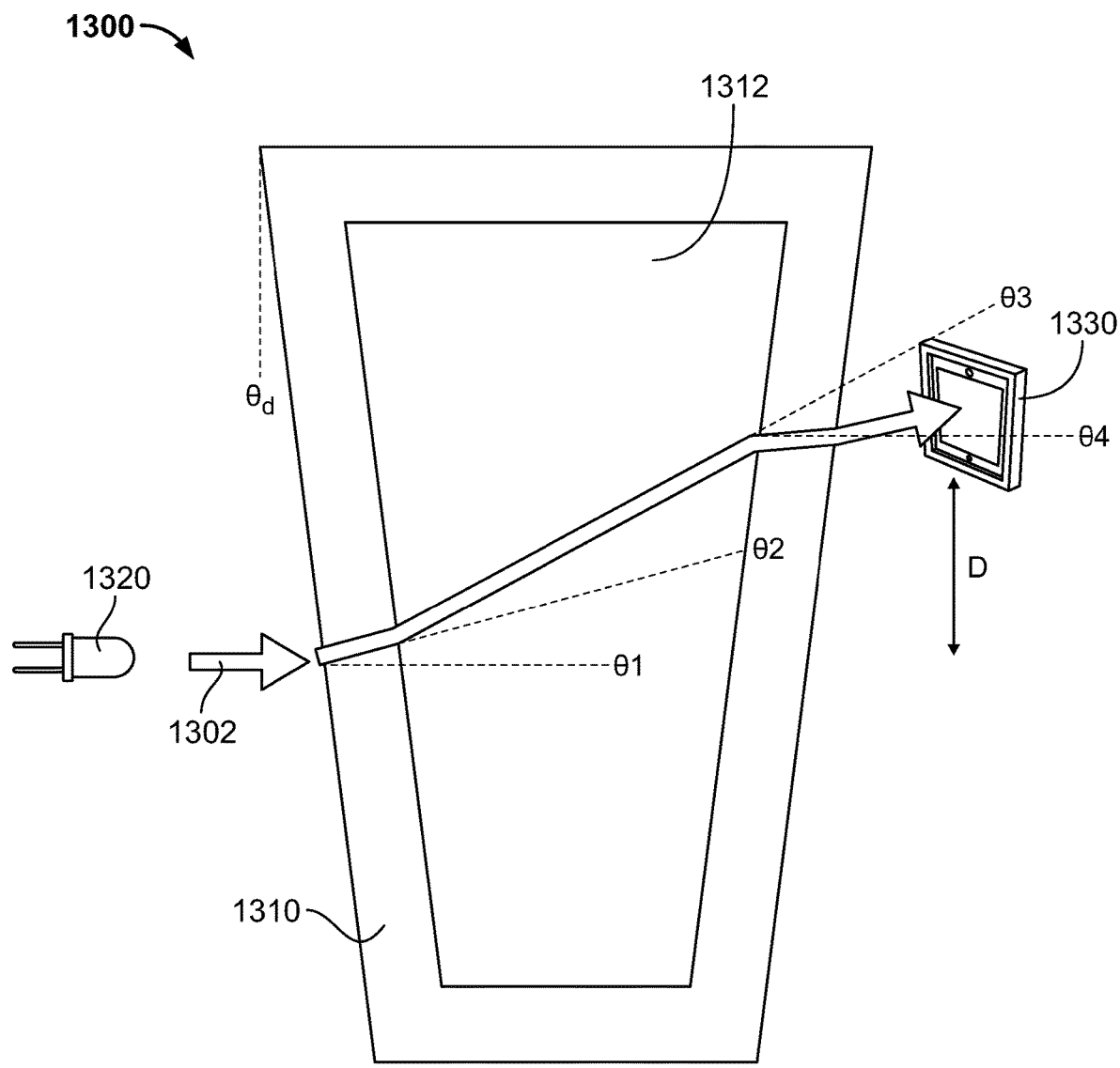
FIG. 13 is a schematic diagram of an illustrative variation of an optical sensor arrangement of a patient monitoring device.

In some variations, an optical sensor arrangement may be configured to at least partially compensate for refraction of an optical measurement region such as a vessel. FIG. 13 is a schematic diagram of optical refraction of illumination (1302) through a vessel (1310). As described in more detail herein, the vessel (1310) may comprise an optically transparent measurement portion and a set of substantially planar surfaces (e.g., sidewalls). The vessel (1310) may comprise a taper $\theta_d$ (e.g., draft angle), such as to help facilitate injection molding or similar manufacturing processes, or to help self-align the vessel (1310) in the mating taper geometry of a holder. In FIG. 13, illumination (1302) generated by illumination source (1320) undergoes refraction at angles $\theta_1$, $\theta_2$, $\theta_3$, and $\theta_4$, as the illumination (1302) travels through the vessel (1310) and patient fluid (1312). As such, the illumination (1302) does not propagate through the vessel (1310) in a straight line out of the illumination source (1320). As shown in FIG. 13, an optical sensor (1330) may be positioned to compensate for this refraction to maximize the received illumination (1302) and thus improve a signal-to-noise ratio. For example, an axial position of an optical sensor (1330) substantially opposite the illumination source (1320) across the vessel (1310) may be slightly offset from the axial position of the illumination source (1320) by a distance (D) in the direction of the refraction. In some variations, the offset distance (D) may, for example, be between about 0.1 mm and about 1 cm. In addition, the optical sensor (1330) may be slightly tilted from to plane of the illumination source (1320) by a predetermined tilt angle. In some variations, the tilt angle may, for example, be between about 0.1 degrees and about 5 degrees.

In some variations, the thickness of an optical measurement region of the vessel may vary in order to reduce refraction and/or the effects thereof. For example, a thickness of at least a portion of the optical measurement region may be thinner than an inlet and outlet of the vessel. As another example, the thickness of at least a portion of the optical measurement gradually decrease in the direction of the expected refraction, to counter or compensate for the expected refraction.

In some variations, a reduction in measured light intensity due to refraction may be determined (e.g., empirically) for each optical sensor and expressed as a refraction constant and/or coefficient. For example, an estimated turbidity based on the measured optical characteristics may be calibrated by a known refraction factor.

In some variations, the patient monitoring device may comprise an ambient light sensor configured to measure ambient light of the environment external to the housing. For example, an ambient light sensor may be disposed on an outer surface of the housing (e.g., adjacent to a display or on a top portion of the housing).

In some variations, the patient monitoring device may comprise a tilt sensor configured to measure an angle of the patient monitoring device relative to ground. An operation of the patient monitoring device may be interrupted in response to detection of tilt, due to the potential trapping of air bubbles when tilted excessively, resulting in inaccurate sensor measurements. Furthermore, a patient may be instructed to orient the patient monitoring device in an upright position. The tilt sensor may comprise an accelerometer, gyroscope, IMU, etc.

In some variations, the patient monitoring device may comprise a fluid conduit sensor configured to detect the presence of a fluid conduit and/or vessel in the holder of the patient monitoring device. The fluid conduit sensor may comprise an optical sensor.

In some variations, the patient monitoring device may comprise one or more optical sensors used to determine if the optical sensor arrangement should be cleaned, serviced, and/or replaced. For example, an optical sensor may be configured to measure light intensity of the illumination source when the holder is empty (e.g., no vessel or fluid conduit is between the optical sensor and illumination source) as a baseline optical measurement. The patient may be notified to clean the optical sensor arrangement if the measured light intensity is below a predetermined threshold. If after cleaning (e.g., wiping down) the illumination source and optical sensor, the measured light intensity is still below the predetermined threshold, then the patient may be notified (e.g., on the display) that the patient monitoring device should be serviced and/or replaced. In some variations, the one or more optical sensors may be the same or different from the optical sensors used to measure optical characteristics of patient fluid.

Output Device

As described above, the patient monitoring device may comprise one or more output devices, such as a display. In some variations, a display may comprise a graphical user interface configured to permit a patient to view information and/or control a patient monitoring device. In some variations, the display may be angled upward towards the patient to aid usability and visualization. In some variations, a display may comprise at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

Figure 15:
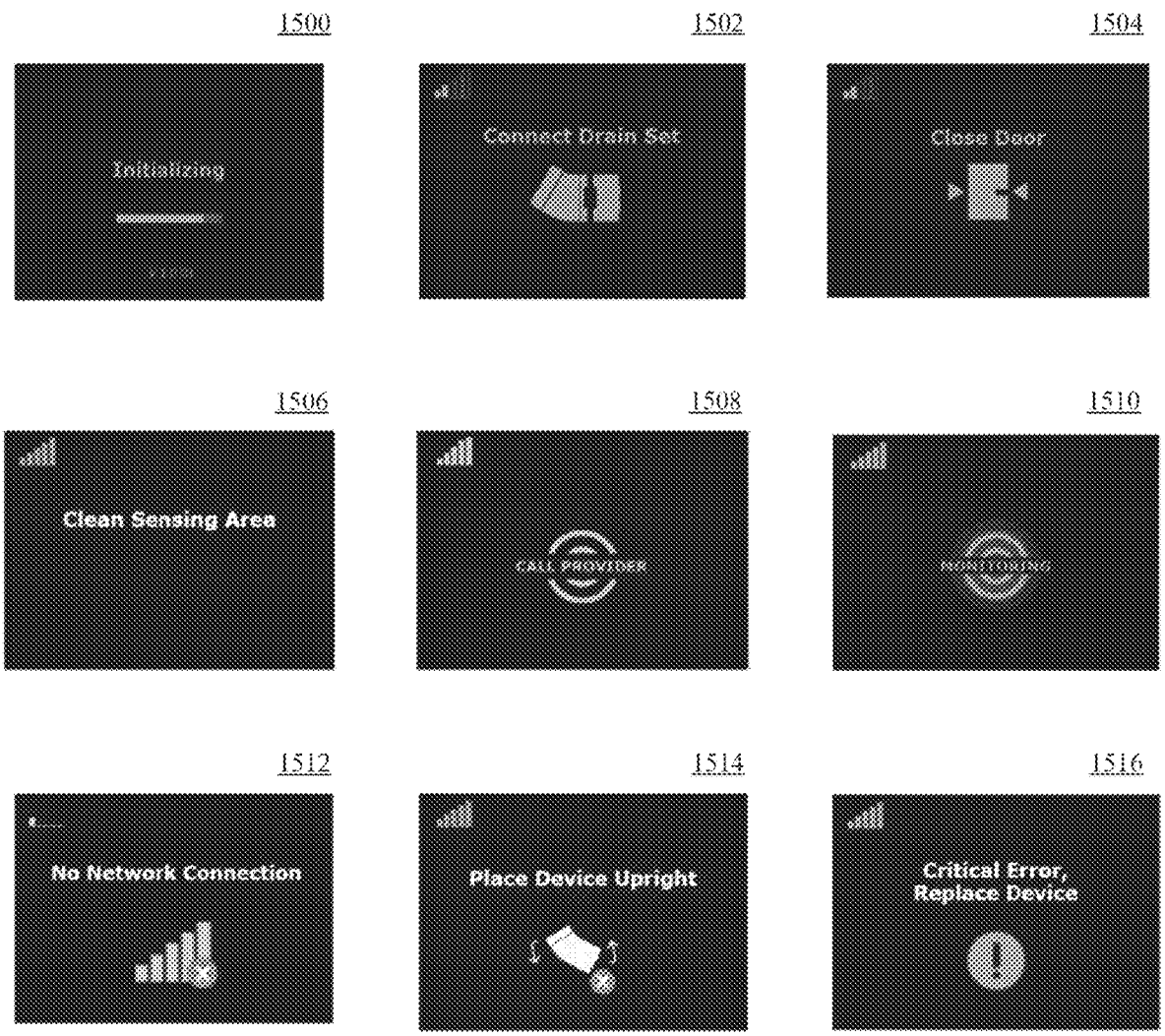
FIG. 15 depicts illustrative variations of a graphical user interface of a patient monitoring device.

FIG. 15 is a set of illustrative variations of a graphical user interface (GUI) that may be displayed on a patient monitoring device. The GUIs permit a patient to view one or more of setup messages, device status, patient status, patient instructions, error messages, and the like. A set of one or more setup GUIs may instruct a patient how to operate the patient monitoring device. A first GUI (1500) may comprise an initialization message such as a startup message. A second GUI (1502) may comprise a connection message. For example, a patient may be instructed to engage a vessel to the patient monitoring device. A third GUI (1504) may comprise a seal message. For example, a patient may be instructed to close a door to form a light seal around a vessel. A fourth GUI (1506) may comprise a cleaning message. For example, a patient may be instructed to clean the patient monitoring device at periodical intervals.

A set of one or more patient status GUIs may inform the patient of an infection state. A fifth GUI (1508) may comprise a positive infection message. For example, a patient may be notified of an infection and instructed to call their provider. In some variations, a positive infection message may be displayed in a different color (e.g., orange, red, yellow). For example, a positive infection message may be color-coded based on severity of infection score (as described in further detail below). In some variations, the patient monitoring device may transmit a positive infection message to a provider. The positive infection message may, for example, include an infection score determined by the system (as described in further detail below). A sixth GUI (1510) may comprise negative infection message. For example, the patient may be notified that the patient monitoring device is monitoring the patient fluid and otherwise operating normally.

A set of one or more device status GUIs may inform the patient of the status of the patient monitoring device. A seventh GUI (1512) may comprise a communication message. For example, a patient may be notified that the patient monitoring device does not form a network connection (e.g., for transmitting patient data). An eighth GUI (1514) may comprise a tilt message. For example, a patient may be instructed to orient the patient monitoring device in an upright position. A ninth GUI (1516) may comprise an error message. For example, a patient may be notified of a failure of at least one component of the patient monitoring device such that the device should be replaced. A failure may, for example, include reduced performance of an illumination source and/or optical sensor below a predetermined threshold.

In some variations, the data may be processed and analyzed on a remote computing device (e.g., remote server) and the results output to a patient's smartphone through a set of GUIs. Additionally or alternatively, the patient monitoring device may comprise an optical waveguide (e.g., light pipe, light distribution guide, etc.) to allow a patient to visualize an infection state. One or more optical waveguides may receive light from a light source (e.g., illumination source) using a predetermined combination of light output parameters (e.g., wavelength, frequency, intensity, pattern, duration) to output an infection state. In some variations, the optical waveguide may be formed integral with the housing of the patient monitoring device to simplify manufacturing and allowing for a compact design and minimal power usage.

An optical waveguide may refer to a physical structure that guides electromagnetic waves such as visible light spectrum waves to passively propagate and distribute received electromagnetic waves. Non-limiting examples of optical waveguides include optical fiber, rectangular waveguides, light tubes, light pipes, combinations thereof, or the like. For example, light pipes may comprise hollow structures with a reflective lining or transparent solids configured to propagate light through total internal reflection. The optical waveguides described herein may be made of any suitable material or combination of materials. For example, in some variations, the optical waveguide may be made from optical-grade polycarbonate. In some variations, the housings as described herein may be co-injected molded to form the optical waveguides. In other variations, the optical waveguides may be formed separately and coupled to the housing. In some variations, the optical waveguides described herein may comprise one or more portions configured to emit light. For example, at least one of the portions may comprise one or more shapes. For example, the optical waveguide may follow the edges of the housing and/or form a shape of a logo. In some variations, the optical waveguides described herein may comprise a surface contour including, for example, a multi-faceted surface configured to increase visibility from predetermined vantage points.

The light patterns described herein may, for example, comprise one or more of flashing light, occulting light, isophase light, etc., and/or light of any suitable light/dark pattern. For example, flashing light may correspond to rhythmic light in which a total duration of the light in each period is shorter than the total duration of darkness and in which the flashes of light are of equal duration. Occulting light may correspond to rhythmic light in which the duration of light in each period is longer than the total duration of darkness. Isophase light may correspond to light which has dark and light periods of equal length. Light pulse patterns may include one or more colors (e.g., different color output per pulse), light intensities, and frequencies.

In some variations, the patient monitoring device may comprise an input device (e.g., touch screen). Some variations of an input device may comprise at least one switch configured to generate a control signal. For example, an input device may comprise a touch surface for a user to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive user movement data from an optical sensor and classify a user gesture as a control signal. A microphone may receive audio data and recognize a user voice as a control signal.

In some variations, the patient monitoring device may comprise an output device such as an audio device and/or haptic device. For example, an audio device may audibly output patient data, fluid data, infection data, system data, alarms and/or notifications. For example, the audio device may output an audible alarm when an infection is predicted and/or when a drain line blockage is detected. In some variations, an audio device may comprise at least one of a speaker, piezoelectric audio device, magnetostrictive speaker, and/or digital speaker. In some variations, a patient may communicate with other users using the audio device and a communication channel. For example, a user may form an audio communication channel (e.g., cellular call, VoIP call) with a remote provider.

In some variations, a haptic device may be incorporated into the patient monitoring device to provide additional sensory output (e.g., force feedback) to the patient. For example, a haptic device may generate a tactile response (e.g., vibration) to confirm user input to an input device (e.g., touch surface).

Network

In some variations, the systems and methods described herein may be in communication with other computing devices via, for example, one or more networks, each of which may be any type of network (e.g., wired network, wireless network). The communication may or may not be encrypted. A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 3G, 4G, and/or 5G networking standards. Some wireless network deployments combine networks from multiple cellular networks or use a mix of cellular, Wi-Fi, and satellite communication.

Controller

Generally, the patient monitoring devices described here may comprise a controller comprising a processor (e.g., CPU) and memory (which can include one or more non-transitory computer-readable storage mediums). The processor may incorporate data received from memory and over a communication channel to control one or more components of the system. The memory may further store instructions to cause the processor to execute modules, processes and/or functions associated with the methods described herein. In some variations, the memory and processor may be implemented on a single chip. In other variations, they can be implemented on separate chips. Additionally or alternatively, one or more controllers (e.g., one or more processors and memory) may be disposed separate from the patient monitoring devices described herein. For example, a patient monitoring device comprising a first controller may be configured to transmit and receive data wirelessly (using a communication device) to a server comprising a second controller. Any of the data processing methods described herein may be performed by one or more of the controllers described herein.

A controller may be configured to receive and process signal data from an optical sensor and other data (e.g., patient data, fluid data) from other sources (e.g., computing device, database, server, provider, user input). The patient monitoring device may be configured to receive, process, compile, store, and access data. In some variations, the patient monitoring device may be configured to access and/or receive data from different sources. The patient monitoring device may be configured to receive data directly input and/or measured from a patient. Additionally or alternatively, patient monitoring device may be configured to receive data from separate devices (e.g., a smartphone, tablet, computer) and/or from a storage medium (e.g., flash drive, memory card). The patient monitoring device may receive the data through a network connection, as discussed in more detail herein, or through a physical connection with the device or storage medium (e.g. through Universal Serial Bus (USB) or any other type of port). The patient monitoring device may be in communication with a computing device that may include any of a variety of devices, such as a cellular telephone (e.g., smartphone), tablet computer, laptop computer, desktop computer, portable media player, wearable digital device (e.g., digital glasses, wristband, wristwatch, brooch, armbands, virtual reality/augmented reality headset), television, set top box (e.g., cable box, video player, video streaming device), gaming system, or the like.

The patient monitoring device may be configured to receive various types of data. For example, the patient monitoring device may be configured to receive a patient's personal data (e.g., gender, weight, birthday, age, height, diagnosis date, anniversary date using the device, etc.), a patient's fluid data, general health information of other similarly situated patients, or any other relevant information. In some variations, the patient monitoring device may be configured to create, receive, and/or store patient profiles (and/or may be in communication with one or more suitable memory devices for creating, receiving and/or storing the same). A patient profile may contain any of the patient specific information previously described. While the above mentioned information may be received by the patient monitoring device, in some variations, the patient monitoring device may be configured to process any data from information it has received using software stored on the device itself, or externally. In another variation, the patient monitoring device may be paired (wired or wirelessly) to other patient monitoring devices (e.g., pulse oximeter, blood pressure monitor) configured to measure one or more patient parameters.

The processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), and/or the like. The processor may be configured to run and/or execute application processes and/or other modules, processes and/or functions associated with the system and/or a network associated therewith. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., siliconconjugated polymer and metal-conjugated polymer-metal structures), mixed analog and digital, and/or the like.

In some variations, the memory may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, and the like. The memory may store instructions to cause the processor to execute modules, processes, and/or functions associated with the communication device, such as signal processing, infection prediction, turbidity estimation, particle estimation, flow detection, bubble detection, patient monitoring device control, and/or communication. Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

In some variations, the patient monitoring device may further comprise a communication device configured to permit a patient and/or to control one or more of the devices of the system. The communication device may comprise a network interface configured to connect the computing device to another system (e.g., Internet, remote server, database) by wired or wireless connection. In some variations, the patient monitoring device may be in communication with other devices via one or more wired and/or wireless networks. In some variations, the network interface may comprise a radiofrequency receiver, transmitter, and/or optical (e.g., infrared) receiver and transmitter configured to communicate with one or more devices and/or networks. The network interface may communicate by wires and/or wirelessly.

The network interface may comprise RF circuitry configured to receive and send RF signals. The RF circuitry may convert electrical signals to/from electromagnetic signals and communicate with communications networks and other communications devices via the electromagnetic signals. The RF circuitry may comprise well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth.

Wireless communication through any of the computing and measurement devices may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some variations, the devices herein may directly communicate with each other without transmitting data through a network (e.g., through NFC, Bluetooth, WiFi, RFID, and the like).

Power Source

In some variations, the patient monitoring device may receive power from an external power source (e.g., wall outlet, generator). The patient monitoring device may receive power via a wired connection, and/or a wireless connection (e.g., induction, RF coupling, etc.). Additionally or alternatively, the patient monitoring device may comprise a portable power source such as a battery. As described in more detail herein, the patient monitoring device may comprise one or more power algorithms configured to conserve energy and increase a lifespan of the patient monitoring device.

Drain Line Extension

The fluid conduits described here may be configured to allow patient fluid to flow through an optical measurement portion for patient infection prediction and/or other characterizations of the patient fluid. In some variations, the fluid conduit may be configured to extend a length of a drain line. Furthermore, the fluid conduit may be a disposable component. In some variations, a fluid conduit may be fluidly coupled to an optically transparent vessel configured for illumination and optical measurement. The vessel may comprise one or more alignment features configured to align the vessel (e.g., in rotation and/or depth) to a patient monitoring device described herein.

Figure 16A:
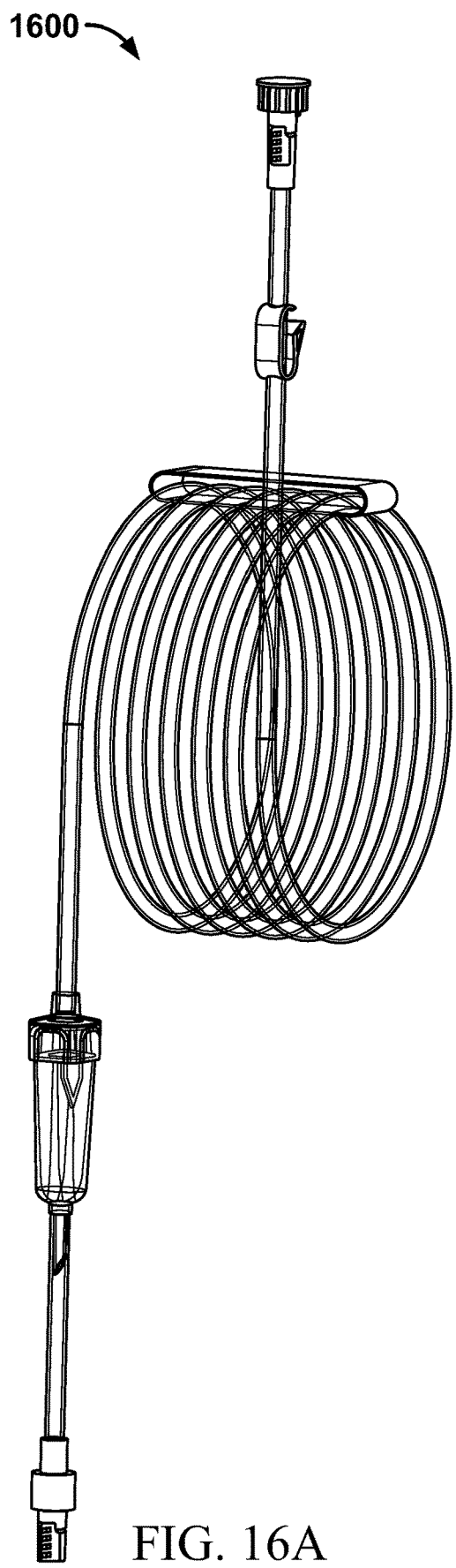
FIG. 16A is a perspective view of an illustrative variation of a drain line extension.
Figure 16B:
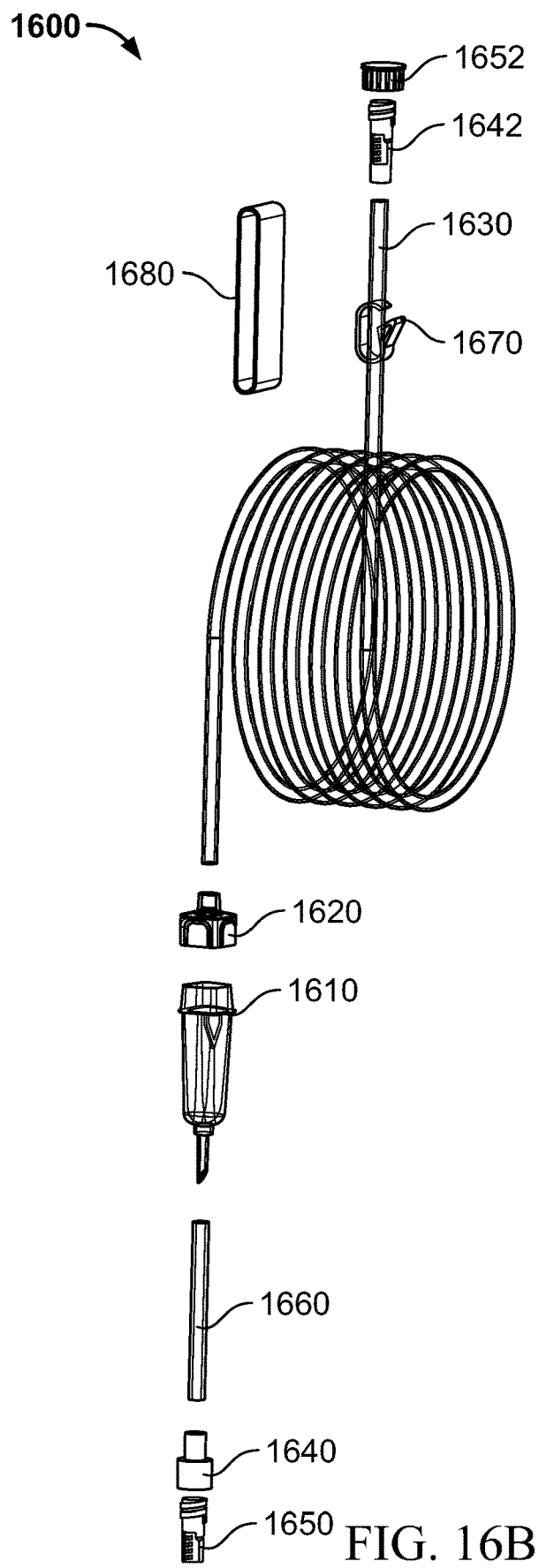
FIG. 16B is an exploded perspective view of the drain line extension depicted in FIG. 16A.

FIG. 16A is a perspective view of a drain line extension (1600) and FIG. 16B is an exploded perspective view of the drain line extension (1600). In some variations, the drain line extension (1600) may comprise one or more of a vessel (1610), cap (1620), fluid conduit (1630), first connector (1640), second connector (1642), first vent cap (1650), second vent cap (1652), vessel extension (1660), shut-off clamp (1670), and packaging holder (1680) (e.g., tape, strip, band). An inlet of the vessel (1610) may be coupled to the vent extension (1660) and an outlet of the vessel (1610) may be coupled to the cap (1620). The vent extension (1660) may have a length sufficient such that the first connector (1640) is external to a housing of a patient monitoring device when the drain line extension (1600) is coupled to a patient monitoring device. An inlet of the vent extension (1660) may be coupled to the first connector (1640) (e.g., male dialysis connector). The first vent cap (1650) may couple to the first connector (1640). An outlet of the cap (1620) may couple to an inlet of the fluid conduit (1630). An outlet of the fluid conduit (1630) may couple to the second connector (1642) (e.g., female dialysis connector), and a second vent cap (1652). In some variations, at least a portion of the fluid conduit (1630), vessel extension (1660) and/or other vent caps, connectors, etc. may be non-transparent to further block or otherwise control entry of ambient light into the drain line extension.

Figure 17A:
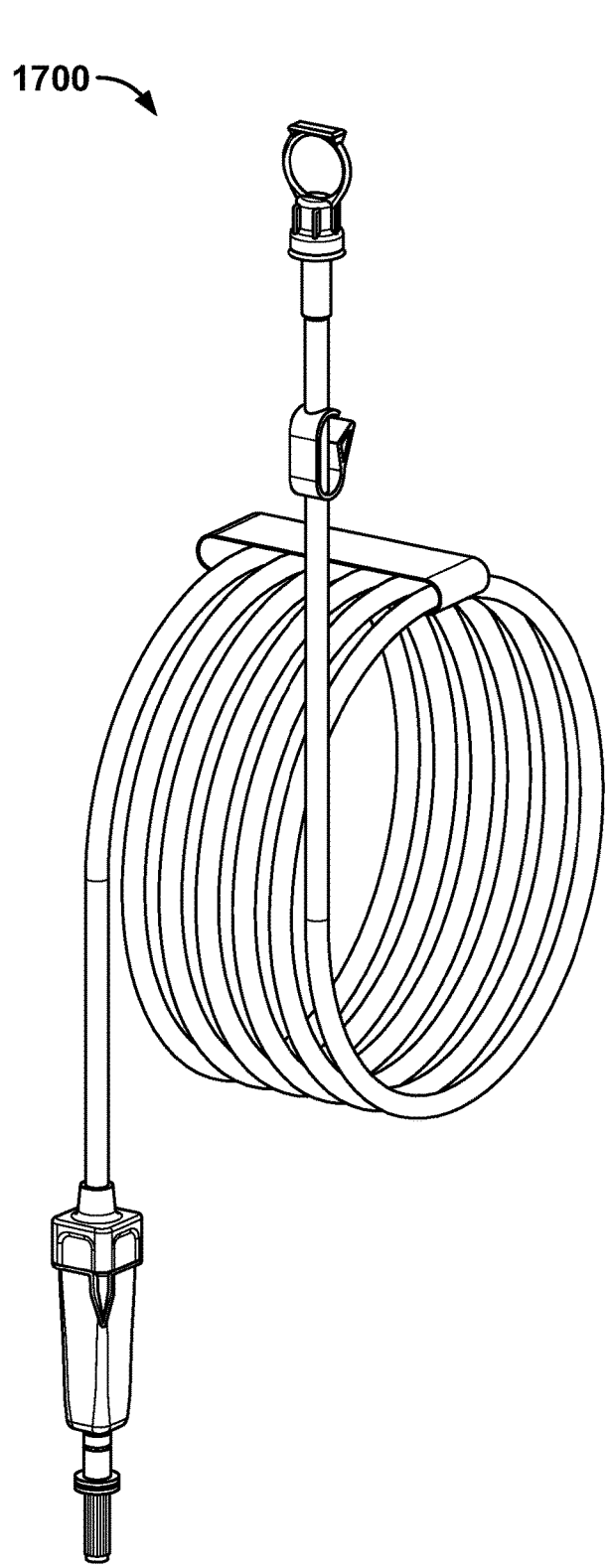
FIG. 17A is a perspective view of another illustrative variation of a drain line extension.
Figure 17B:
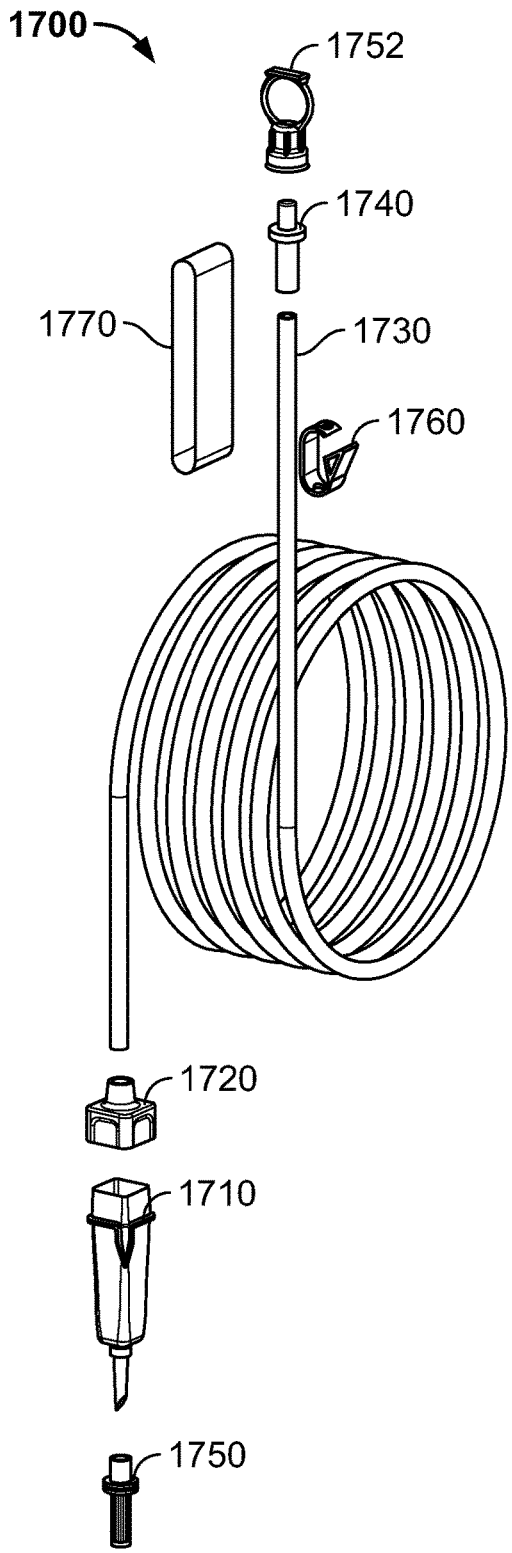
FIG. 17B is an exploded perspective view of the drain line extension depicted in FIG. 17A.

FIG. 17A is a perspective view of a drain line extension (1700) and FIG. 17B is an exploded perspective view of the drain line extension (1700). In some variations, the drain line extension (1700) may comprise one or more of a vessel (1710), cap (1720), fluid conduit (1730), connector (1740) (e.g., bushing), first vent cap (1750), second vent cap (1752), shut-off clamp (1760), and packaging holder (1770) (e.g., tape). An inlet of the vessel (1710) may be coupled to the first vent cap (1750) (e.g., spike vent cap) and an outlet of the vessel (1710) may be coupled to the cap (1720). An outlet of the cap (1720) may couple to an inlet of the fluid conduit (1730). An outlet of the fluid conduit (1730) may couple to the connector (1740) and a second vent cap (1752). In some variations, at least a portion of the fluid conduit (1730) and/or other vent caps, connectors, etc. may be non-transparent to further block or otherwise control entry of ambient light into the drain line extension.

Figure 17C:
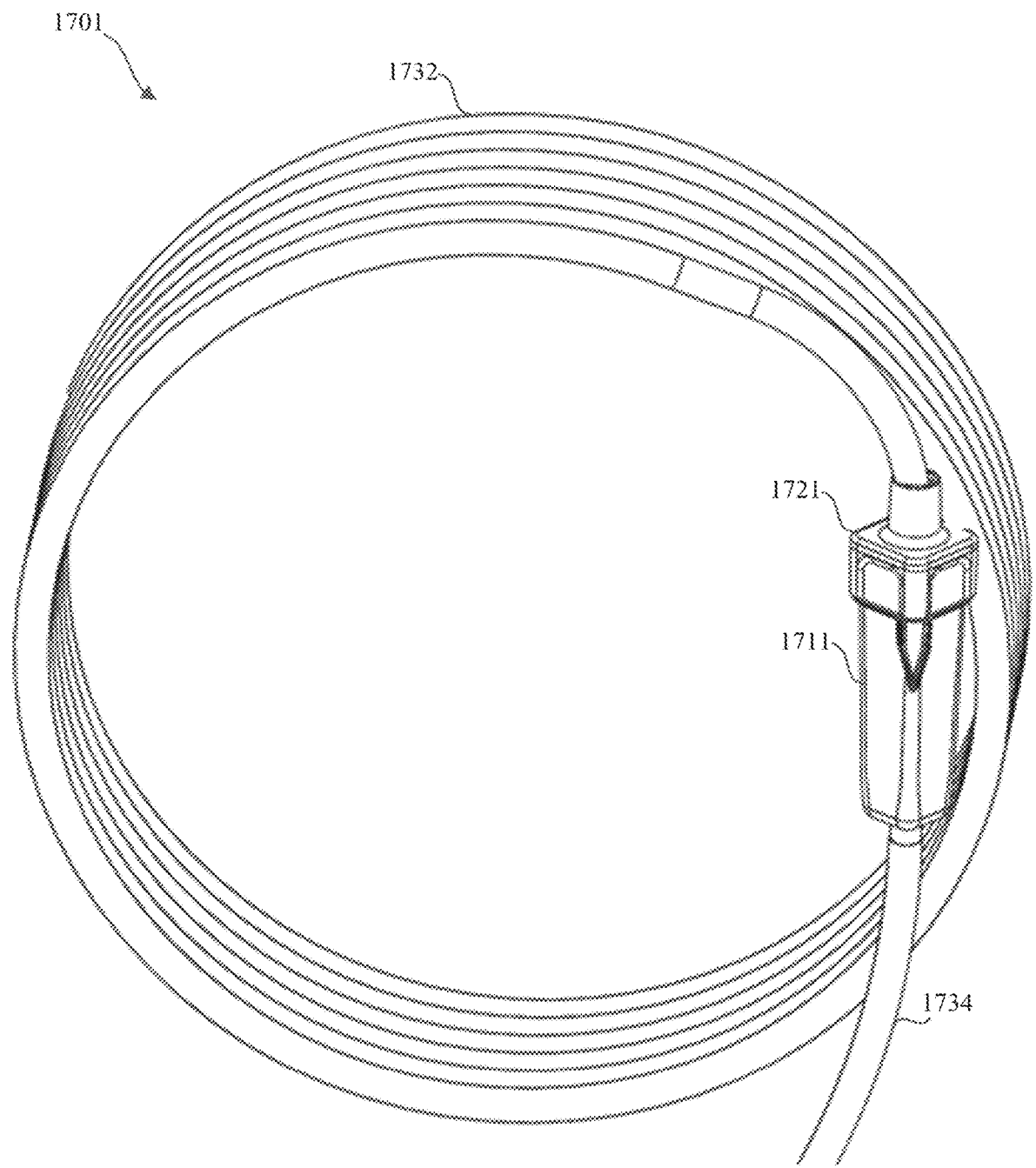
FIG. 17C is a perspective view of another illustrative variation of a drain line.
Figure 18A:
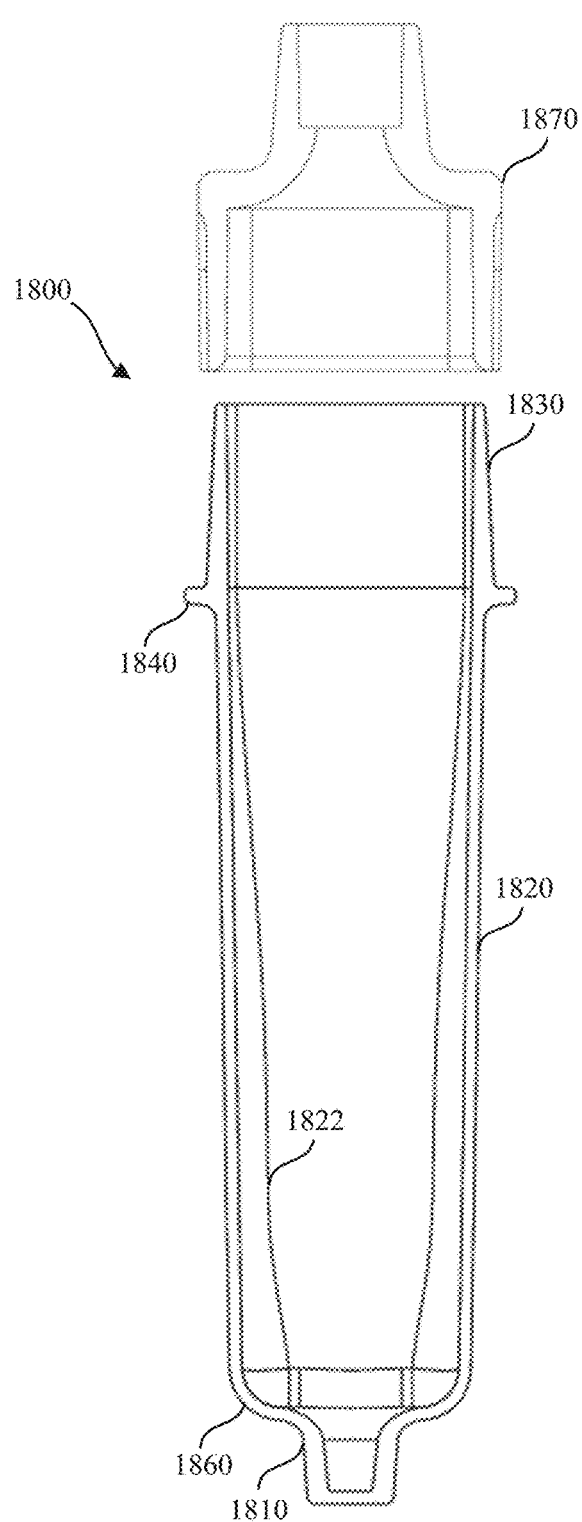
Figure 18B:
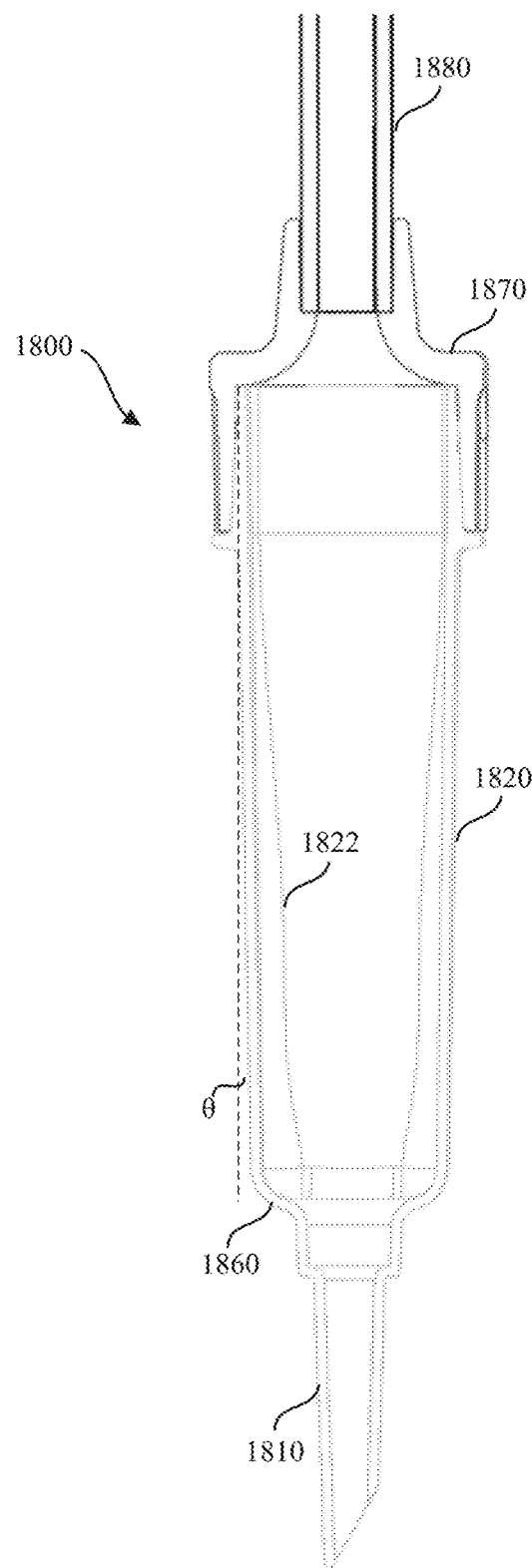
Figures 18C, 18D:
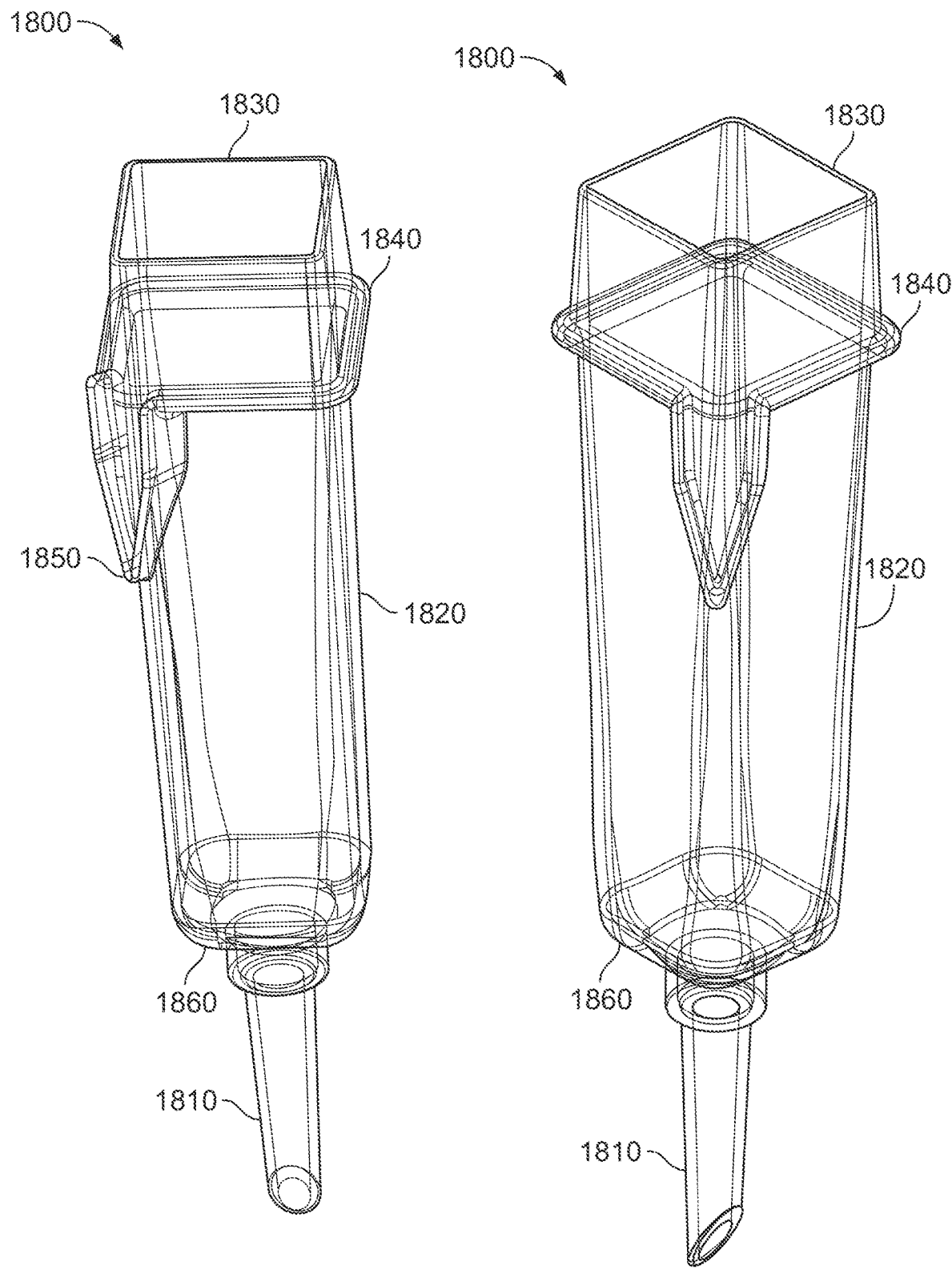
Figures 18E, 18F:
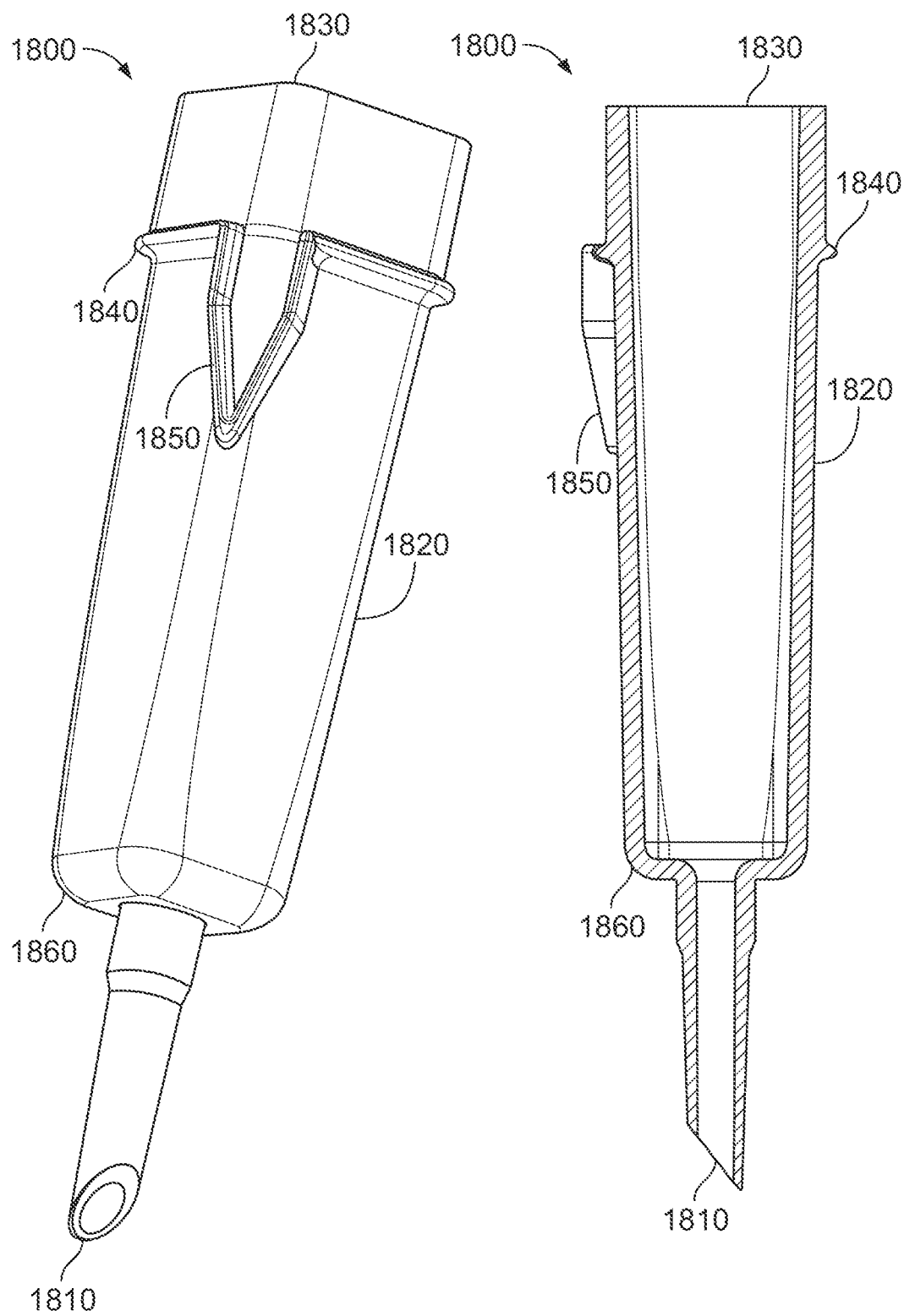

Although FIGS. 17A and 17B depict a drain line extension including an optically transparent vessel configured for illumination and optical measurement, it should be understood that in other variations an optically transparent vessel may additionally or alternatively be arranged along any portion of a fluid conduit in fluidic communication with a drainage output of a cycler. For example, in some variations, a drain line that is part of a base tubing set (rather than a drain line extension) may include an optically transparent vessel or optically transparent measurement portion. For example, FIG. 17C is a perspective view of an exemplary variation of a cycler drain line (1701) assembled with a vessel (1711). The cycler drain line (1701) may comprise a first portion (1734) (e.g., inlet) and a second portion (1732) (e.g., outlet). For example, a vessel (1711) comprising an optically transparent measurement portion as described herein may be assembled in-line with the drain line (e.g., tubing set) (1701). In some variations, the vessel (1711) may be configured to attach to the drain line (1701) using a solvent bond and/or adhesive as described herein. The integrated drain line (1701) depicted in FIG. 17C may, for example, reduce the number of assembly steps in CCPD treatment and therefore may increase patient compliance and sterility.

In some variations, a fluid vessel (e.g., optically transparent measurement portion) may be disposed within one or more portions of a drain line or drain line extension (e.g., proximal, distal, and in-between). In some variations, an optically transparent measurement portion may be disposed within an end portion (e.g., proximal portion, distal portion) of a drain line. For example, a CAPD system may comprise a drain line coupled between a Y-connector and a drainage vessel where a proximal portion of the drain line may comprise an optically transparent measurement portion adjacent to (e.g., downstream of) the Y-connector. As another example, a proximal end of an in-dwelling catheter may comprise a fluid vessel as described herein. In a CCPD system, an optically transparent measurement portion of the in-dwelling catheter may be coupled adjacent to the drain line of the cycler tubing set. An optically transparent measurement portion disposed at an end of a drain line may reduce manufacturing complexity and therefore reduce associated costs.

The drain line extensions described herein may be compatible with standard connectors and/or adapters. The vent caps may be configured to protect a lumen of the fluid conduit and vessel from contamination. For example, a spike vent cap may be configured to protect a packaging of the drain line extension from being punctured by the sharp tip of the vessel. One or more of the vent caps may additionally or alternatively include anti-contamination features such as tortuous channels to help prevent passage of contaminants into the drain line fluid conduit. In some variations, one or more outer surfaces of the drain line extension, except for an optical measurement region of the vessel, may be textured so as to prevent sticking and/or reduce ambient light leakage into the vessel. In some variations, one or more portions of the drain line extension, except for an optical measurement region of the vessel, may be non-transparent to reduce ambient light leakage into the vessel. For example, the cap may be opaque and the fluid conduit may be translucent. The inlet and outlet portions of the vessel may be non-transparent as well.

The drain line extension may further include a measurement vessel, which may define a volume receiving patient fluid for measurement by the patient monitoring device. Conventional cuvettes used for fluid analysis generally have precise dimensions and must meet strict manufacturing tolerances that do not allow for injection molding and similar cost-effective techniques. However, in contrast, the vessels described herein may comprise a number of structural features which may be formed utilizing high yield, low-cost manufacturing techniques such as injection molding and solvent bonding, while enabling high quality optical measurements, as further described below.

FIGS. 18A-18I are various views of a vessel (1800) for use in a fluid conduit comprising an inlet (1810) (e.g., spike), outlet (1830), and an optically transparent measurement portion (1820) between the inlet (1820) and outlet (1830). The measurement portion (1820) may comprise an internal volume configured to receive fluid such as patient fluid. During use of the vessel (1800), patient fluid may pass into the measurement portion (1820) through the inlet (1810) and pass out of the measurement portion (1820) through the outlet (1830). For example, the patient fluid may be continuously pumped through the vessel (1800) during a measurement period. At least one cap (1870) may be coupled to an outlet (1830) and/or inlet of the vessel. A fluid conduit (1880) may be coupled to an outlet of the cap (1870). A drain line or other tubing may be coupled to the inlet (1820).

In some variations, the vessel (1800) may be comprise one or more optical features configured to aid optical measurement of patient fluid through the vessel (1800). The measurement portion (1820) may comprise at least two substantially planar surfaces that may be orthogonal to each other or opposite to each other. Such planar or flat surfaces may be advantageous for the devices and methods described herein, because less light bending is incurred by flat surfaces (compared to conventional, round-surfaced cuvettes). As shown in FIG. 18G, the measurement portion (1820) may comprise a square cross-section. The substantially planar surfaces and square cross-section may reduce refraction relative to a cylindrical conduit and may improve the consistency and quality of optical measurement through the vessel (1800). The square cross-section may further aid alignment of the vessel (1800) with an optical sensor arrangement of a patient monitoring device.

In some variations, the internal volume of the measurement portion (1820) may comprise one or more bubble mitigation features that may reduce the generation and presence of bubbles within the vessel (1800), and thus increase a signal-to-noise ratio of optical measurements using the vessel (1800). For example, the internal volume may comprise bubble mitigation features such as radiused corners (1860) and a taper (1822). Radiused corners may reduce the number of sharp transitions and edges where bubbles may form and accumulate (e.g., during an initial fluid fill, during continuous flow, etc.).

In some variations, the vessel (1800) may comprise one or more ambient light reduction features to reduce ambient light leakage into the measurement portion (1820) of the vessel. For example, one or more of the inlet (1810) and outlet (1830) may include a non-transparent (e.g., opaque, translucent) material and/or coating. One or more of the inlet (1810) and outlet (1830) may comprise texturing to provide a grip interface for a patient and/or form a light seal. Furthermore, a non-transparent connector may be coupleable to the inlet (1810) and/or the outlet (1830).

In some variations, the vessel (1800) may comprise one or more alignment features configured to aid engagement and positioning of the vessel (1800) relative to an optical sensor arrangement of a patient monitoring device. For example, the vessel (1800) may comprise a depth alignment feature (1840) and/or a rotational alignment feature (1850). In some variations, the depth alignment feature (1840) may be disposed around a perimeter of the vessel (1840). The depth alignment feature (1840) may engage with a shoulder or other mating or interfering feature of the holder in the patient monitoring device (e.g., shoulders (1253) of the patient monitoring device (1200) shown in FIG. 12A). The rotational alignment feature (1850) may engage with a slot or recess of the holder in the patient monitoring device (e.g., engagement feature (1012) of the holder shown in FIG. 10A). In some variations, the rotational alignment feature (1850) may be formed so to not overlie regions of the measurement portion (1820) that will be aligned with the illumination sources and optical sensors in the patient monitoring device when the vessel is placed in the patient monitoring device. Accordingly, in these variations, the placement of the rotational alignment feature (1850) is selected as to avoid interfering with optical measurements. For example, as shown in FIGS. 18C-18F, the rotational alignment feature (1850) may be arranged over a corner of the measurement portion (1820) rather than over one of the planar surfaces. The depth alignment feature (1840) and/or rotational alignment feature (1850) may comprise protrusions.

In some variations, the vessel (1800) may comprise one or more features configured to aid manufacturing of the vessel (1800). In some variations, at least a portion of the measurement portion (1820) may be tapered. For example, the measurement portion (1820) may comprise a draft angle (θ) of between about 0.5 degrees and 2 degrees. Moreover, injection molded parting lines may be located above and below the optical measurement portion (e.g., along the depth alignment feature). In some variations, the vessel (1800) may be coupled to a cap (1870) (such as that described below) by solvent bonding. Solvent bonding may be a cost-effective and efficient manufacturing technique. For example, the solvent may comprise a cyclohexanone and/or methyl ethyl ketone.

In some variations, the vessel (1800) may be composed of a material having good optical clarity and high transmission properties of desired wavelengths of light. For example, the vessel may comprise one or more of copolyester, acrylonitrile butadiene styrene, polycarbonate, acrylic, cyclic olefin copolymers, cyclic olefin polymers, polyester, polystyrene, ultem, polyethylene glycol-coated silicone, zwitterionic coated polyurethane, polyethylene oxide-coated polyvinyl chloride, and polyamphiphilic silicone. For example, the vessel (1800) may be composed of VLD-100 Acrylic, Cyro H15-011 acrylic, Acritherm HS Acrylic HS3125, Acrylic V825, Acritherm HS3, Cyclo-Olefin Polymer Zeonex E48R, Cyclo-Olefin Polymer Zeonex 1020R, Cyclo-Olefin Polymer 1060R, Cyclo-Olefin Polymer TPX RT-18, COC Topas, Polycarbonate LExan 1130-112, Lexan HSP6-1125, Polyester OKP4, Dow 685D Polystyrene, and Ultem 1010-1000.

In some variations, a cap may be coupled to an end (e.g., inlet, outlet) of a vessel and may function as a connector for a fluid conduit. For example, the cap may provide a transition between the vessel cross-section and a cross-section of the rest of the fluidic conduit (e.g., from a square cross-section of the vessel to a circular cross-section of the fluidic conduit). FIGS. 19A-19D are various views of a cap (1900) for a vessel comprising an outlet (1910), inlet (1920), and grip (1930). In some variations, the cap (1900) may comprise one or more ambient light reduction features to reduce ambient light propagation from tubing of the fluid conduit into the vessel. For example, the cap (1900) may include a non-transparent material and/or coating (e.g., opaque, translucent). Furthermore, an outer surface of the grip (1930) may comprise texturing to provide a grip interface for a patient and/or form an ambient light seal. For example, the grip (1930) on the cap (with the cap coupled to the vessel) may allow the patient to handle the vessel without touching and contaminating the optically sensitive transparent sidewalls. In some variations, the grip may include one or more recesses that are configured to receive a finger, though in other variations the grip may additionally or alternatively include outwardly projecting texturing such as ribs, etc.

In some variations, the cap (1900) may be coupled to the vessel via an interference fit. In some variations, the cap (1900) may have a vessel-interfacing surface that is configured to fit over an end (outlet or inlet) of the vessel, and is undersized relative to the end of the vessel to promote an interference fit. Alternatively, in other variations, the cap (1900) may have a vessel-interfacing surface that is configured to fit within an end (outlet or inlet) of the vessel, and is oversized relative to the end of the vessel to promote an interference fit. Furthermore, in these variations the cap (1900) may include a material that is less rigid (e.g., semi-rigid) than the vessel to further enable the interference fit between the cap (1900) and vessel. Additionally or alternatively, the cap may be coupled to the vessel via solvent bonding. In some variations, the cap (1900) may comprise a semi-rigid material such as PVC (e.g. shore hardness 90A), the vessel may comprise a rigid material such as Copolyester (e.g., Tritan MX731), and the cap (1900) may be further solvent bonded to the vessel with solvent-cyclohexanone and/or methyl ethyl ketone.

Figure 19A:
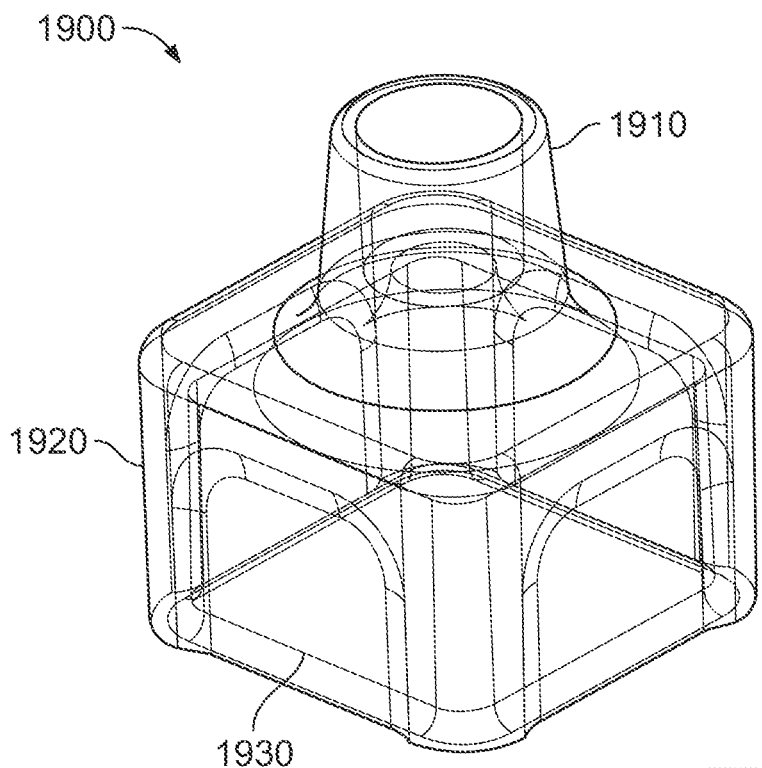
FIGS. 19A and 19B are perspective views of an illustrative variation of a cap.
Figure 19B:
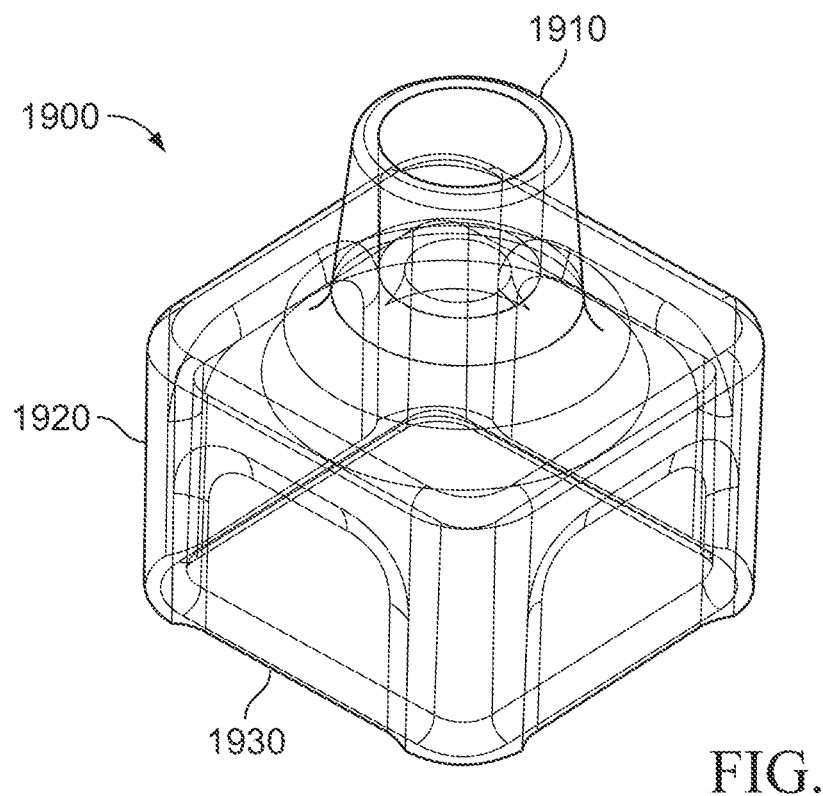
Figure 19C:
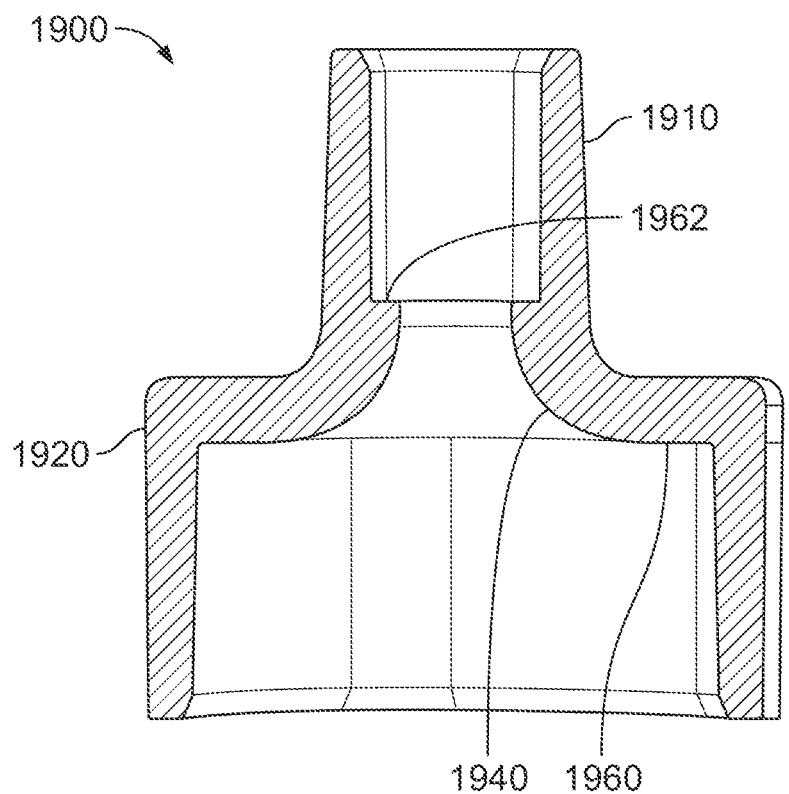
FIG. 19C is a cross-sectional side view of an illustrative variation of a cap.
Figure 19D:
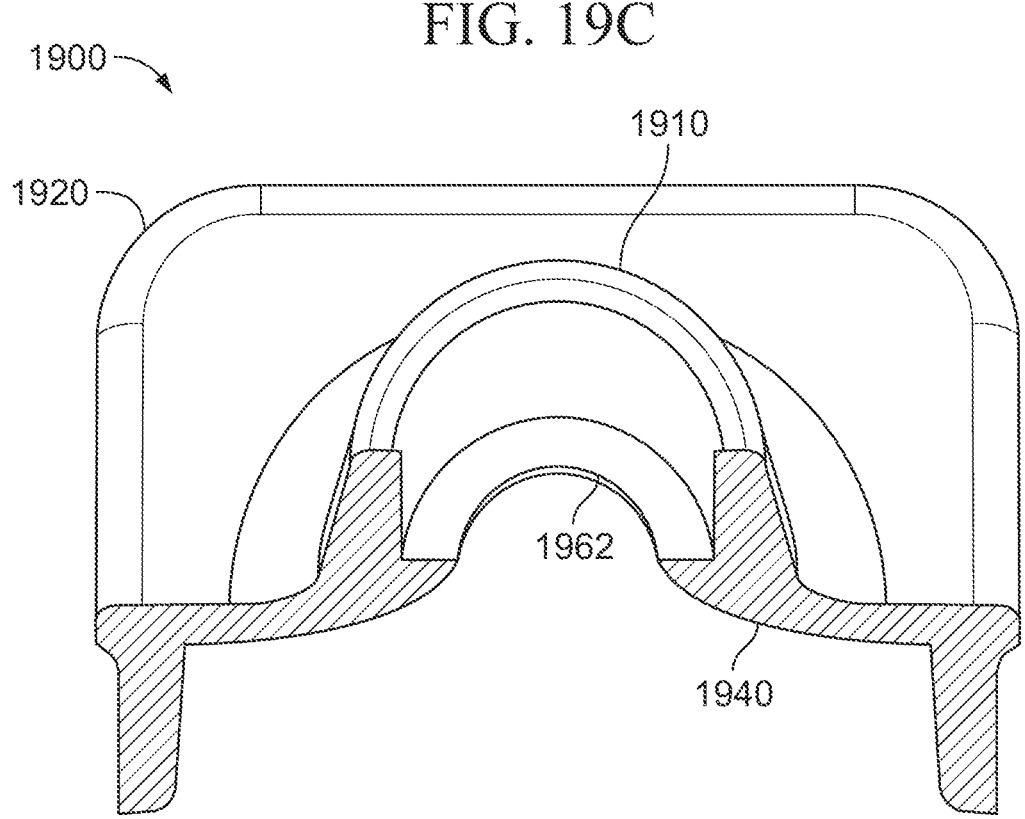
FIG. 19D is a cross-sectional perspective view of the cap depicted in FIG. 19C.

As shown in FIGS. 19C and 19D, in some variations, an internal volume of the cap (1900) may comprise one or more interfaces (1960, 1962) configured to provide an internal stop for engagement to an outlet of a vessel or fluid conduit. For example, the cap (1900) may include a vessel-interfacing stop (1960) configured to engage or mate with an end of the vessel, and/or a conduit-interfacing stop (1962) configured to engage or mate with an end of a fluidic conduit. In some variations, the cap may be coupled to the end of a fluidic conduit with solvent bonding, similar to that described above.

In some variations, the internal volume may further comprise one or more bubble mitigation features similar to that described above for the vessel, such as radiused corners (1940) and/or tapered transitions in shape.

Patient Monitoring Methods

Also described here are methods for monitoring a patient fluid using the systems and devices described herein. For example, methods may comprise one or more of predicting infection of a patient, estimating particle concentration of a fluid, estimating fluid flow, and bubble detection. These methods may be useful for monitoring peritoneal dialysis patients that use in-dwelling catheters that are susceptible to infection complications. It should be appreciated that any of systems and devices described herein may be used in the methods described herein.

Infection Prediction

Generally, the methods for predicting infection may be based on optical measurements of patient fluid. For example, optical scatter and/or obscuration of the patient fluid may be measured through an optically transparent vessel. These optical measurements may be used to estimate turbidity values of the patient fluid. Furthermore, specific particle concentrations may be estimated based on light absorption patterns across specific wavelengths and the resultant variations in light scatter sensor outputs. An infection score may be generated based on the estimated optical properties (e.g., turbidity) and/or the change of the optical properties over time. A prediction that a patient is infected may be based on one or more of the infection score and a set of predetermined criteria.

As described above, generally, infection may be correlated with concentration of one or more particle types, such as leukocytes, in the patient fluid. Concentration of leukocytes and/or other particle types may be estimated or measured based on a turbidity of the patient fluid, as estimated or measured using methods and devices such as those described herein.

In some variations, a method of predicting infection may include illuminating a patient fluid in a fluid conduit from a plurality of illumination directions. For example, the illumination directions may be generally orthogonal to each other, or approximately 180 degrees offset from each other.

In some variations, illumination output from a single illumination source enables a scatter angle light intensity measurement (e.g., 90 degrees) and an absorption/obscuration/attenuation angle light intensity measurement (e.g., 180 degrees). For example, in FIG. 14A, the first optical sensor (1420) may be configured to measure 180 degree scatter angle (e.g., attenuation) light intensity measurements of patient fluid ($T_1$) based on illumination output from the first illumination light source (1410). The first optical sensor (1420) may further measure 90 degree scatter angle light intensity measurements of patient fluid ($N_2$) based on illumination output from the second illumination light source (1412). Similarly, the second optical sensor (1422) may be configured to subsequently measure 180 degree scatter angle light intensity measurements of patient fluid ($T_2$) based on illumination output from the second illumination light source (1412). The second optical sensor (1422) may further measure 90 degree scatter angle light intensity measurements of patient fluid ($N_1$) based on illumination output from the first illumination light source (1410). The light intensity measurements ($T_n$, $N_n$) may be measured separately (e.g., sequentially) such that an optical sensor measures light intensity from a single illumination source and not a plurality of illumination sources at the same time.

In some variations, the first illumination source (1410) and the second illumination source (1412) may illuminate the patient fluid in a first plane such that a first illumination direction of the first illumination source (1410) and a second illumination direction of the second illumination source (1412) are substantially coplanar. In some variations, the patient fluid may be illuminated through a plurality of parallel illumination planes (e.g., first plane, second plane, third plane) substantially orthogonal to a fluid conduit.

In some variations, each illumination source in an illumination plane (e.g., first plane, second plane, third plane) may illuminate patient fluid at a same wavelength such that the illumination sources in the illumination plane output redundant wavelengths. A plurality of illumination sources illuminating the patient fluid at the same wavelength may improve optical sensor measurements by canceling out erroneous signals, for example.

In some variations, sensor measurement error detection may be performed to exclude unreliable light intensity measurements that may result from sources of error such as damaged, malfunctioning, or dirty optical components (e.g., illumination source, optical sensor) in the optical system. In some variations, paired light intensity measurements may also be used to validate the light intensity measurements. For example, light intensity measurements of patient fluid $N_1$ and $N_2$ may be used to calculate a percentage difference (e.g., (N2−N1)/N1×100). In some variations, both of the light intensity measurements may be invalidated (e.g., not used) if the percentage difference exceeds a predetermined threshold (e.g., 10%). In other variations, the higher light intensity measurement may be invalidated (e.g., not used) if the percentage difference exceeds a predetermined threshold (e.g., 10%), and only the lower value measurement would be used.

In some variations, an illumination source such as an LED may emit light based on pulse width modulation (PWM). In some variations, a first illumination source using PWM may emit multiple light pulses (pulse "ON" phase) during which a first optical sensor may synchronously measure the light intensity during the pulse ON phase, followed by measurements using a second optical sensor. The first illumination source may turn OFF and a second illumination source using PWM may emit multiple light pulses (pulse "ON" phase), during which the second optical sensor may synchronously measure the output during the pulse ON phase, followed by measurements using the first optical sensor. During each PWM ON sequence, a single measurement or a plurality of measurements may be taken by the optical sensors. Multiple measurements allow for statistical processing of the measurements, such as deriving the measurement's average, median, standard deviation, minimum, maximum, or more complex statistical modeling such as outlier analysis and removal. During the PWM ON sequence, the optical sensors may be configured to add a delay before measuring within each pulse ON phase to account for the warm-up stabilization time of the illumination source in order to provide more accurate optical measurements. The delay for warm-up stabilization may comprise a portion of a single pulse or multiple pulses.

Generally, the measured optical characteristics may be used to estimate turbidity of the patient fluid, which may be correlated to particle (e.g., leukocyte) concentration in order to provide an indication of infection state (e.g., based on empirical correlations). The 180 degree scatter angle light intensity measurements ($T_1$, $T_2$) are more sensitive to changes in illumination intensity than for 90 degree scatter angle light intensity measurements ($N_1$, $N_2$). In some variations, the first illumination light source (1410) may illuminate the patient fluid and the first optical sensor (1420) may measure $T_1$ and the second optical sensor (1422) may measure $N_1$. Then, the second illumination light source (1412) may illuminate the patient fluid and the first optical sensor (1420) may measure $N_2$ and the second optical sensor (1422) may measure $T_2$. The time period between sequential optical measurements using the first and second illumination sources should be minimized to ensure measurement of the same portion of patient fluid. Based on these measurements, the turbidity of the patient fluid may be estimated based on the equations Turbidity$_1$ and Turbidity$_2$, below:

$$\text{Turbidity}_1 = \sqrt{(N_1 * N_2)/(T_1 * T_2)}$$

$$\text{Turbidity}_2 = \sqrt{(N_1 * N_2)}$$

The Turbidity$_1$ equation may provide high accuracy and the Turbidity$_2$ equation may be robust against changes in light intensity due to the light sources, and/or due to variances in the vessel (e.g., manufacturing variations). In some variations, the turbidity equation used to estimate a turbidity of the patient fluid may be selected based on a measured light intensity variation between the optical sensors. For example, if the measured $T_1$ and $T_2$ are within a predetermined range of each other (e.g., 75%, 80%, 85%, 90%, 95%, 98%, etc.), then turbidity may be estimated using the Turbidity equation. Otherwise, turbidity may be estimated using the Turbidity$_2$ equation. In some variations, turbidity may be estimated using both equations and some combination of the estimated turbidities may be used. For example, the estimated turbidities may be averaged and/or weighted. Furthermore, the estimated turbidities may be sampled over a predetermined time period with the set of samples being averaged and/or weighted. For example, a single turbidity value used for infection prediction may be generated for each drain cycle based on an averaging of a plurality of estimated turbidities during the drain cycle. In some variations, a sampling frequency of the patient fluid may be increased based on a predicted positive infection state.

In some variations, the measured optical characteristics of the patient fluid illuminated from a plurality of illumination directions may be used to calibrate the patient monitoring device. For example, a significant difference between the measured $T_1$ and $T_2$ may indicate that at least one of the illumination sources may be failing and should be replaced. In response, one or more of the patient, provider, and manufacturer may be notified that the patient monitoring device requires servicing and/or replacement. For example, the patient may be notified to "Call Provider" or "Replace Device" by the patient monitoring device. In some of these variations, the patient monitoring device may cease patient monitoring functions until calibration and/or servicing is performed.

In some variations, illumination output from a single illumination source enables a plurality of scatter angle light intensity measurements (e.g., 90 degrees). Although the optical sensors in this configuration do not provide 180 degree scatter angle light intensity measurements, they are configured to capture side scatter illumination from different illumination sources. For example, in FIG. 14B, the first optical sensor (1420) may be configured to separately measure 90 degree scatter angle light intensity measurements ($N_{1,1}$ and $N_{2,1}$) based on respective illumination output from the first illumination light source (1410) and the second illumination source (1412). Similarly, the second optical sensor (1422) may be configured to measure 90 degree scatter angle light intensity measurements ($N_{1,2}$ and $N_{2,2}$) based on respective illumination output from the first illumination light source (1410) and the second illumination light source (1412).

$$\text{Turbidity}_3 = \sqrt{(N_{1,2} * N_{2,2})/(N_{1,1} * N_{2,1})}$$

The Turbidity$_3$ equation may be robust against changes in light intensity relative to the Turbidity$_1$ equation.

In some variations, the turbidity (as determined by one or more of the above-described turbidity equations) may be correlated to an infection state (e.g., based on empirical correlations), which may be quantified with an infection score. The infection score may, for example, be expressed in terms of nephelometric turbidity units (NTU). In some variations, the estimated turbidity may be scaled (e.g., normalized) to an infection score scale, such as between 0-100. In another variation, an infection score may be based on the rate of change of turbidity measured of successive samples over a predetermined time period (e.g., 24 hours).

Additionally or alternatively, as further described below, any one or more of the above turbidity equations may be used to determine one or more other patient fluid characteristics, such as particle composition estimation, fluid flow estimation (e.g., detecting whether the cycler is ON or OFF), detecting bubbles in the patient fluid, etc.

Ambient Light Subtraction

Ambient light leakage or propagation through one or more of the housing of the patient monitoring device, fluid conduit, and the vessel may alter optical measurements due to factors such as manufacturing tolerances, wear, and environmental conditions. In some variations, an optical sensor may be calibrated at predetermined intervals to compensate for ambient light leakage. Accordingly, ambient light (e.g., not generated by an illumination source) may be removed from the measured signals to improve the estimated turbidity, infection prediction, and other analysis performed on the measured signals.

In some variations, ambient light noise may be measured and removed from subsequent optical measurements and signal processing. For example, a baseline optical measurement corresponding to ambient light levels may be performed. This baseline may be subtracted from the subsequent optical measurements and may, for example, improve the estimated turbidity and infection prediction. In some variations, the baseline optical measurement may be performed when the empty fluid conduit and vessel are initially attached and enclosed within a patient monitoring device and when the illumination sources are turned OFF. Any signal measured by the optical sensors during this baseline measurement ("dark" signal) may be attributed to ambient light leakage and/or electrical noise. Subsequent optical measurements may be calibrated against this baseline measurement where the baseline measurement is subtracted from each subsequent optical measurement ("light" signal). In other words, the "true" measurement specifically attributable to characteristics of the patient fluid may be determined as the difference between the "light" signal and the "dark" signal. In another variation, an optical measurement of the patient fluid may include a baseline measurement. For example, the following sequence may be used: While first and second illumination sources are OFF, a dark signal is be measured at the first and second optical sensors. The first illumination source is turned ON and light intensity is measured at the first and second optical sensors. The first illumination source is turned OFF and a dark signal is measured at the first and second optical sensors. The second illumination source is turned ON and light intensity is measured at the first and second optical sensors. This sequence may be repeated at a predetermined interval (e.g., every optical measurement of the patient fluid). In some variations, an optical sensor disposed on an external surface of a housing of a patient monitoring device may additionally or alternatively be used to generate or contribute to the baseline measurement.

In some variations, the baseline optical measurement may be performed at any time when the illumination sources are turned OFF and the patient fluid is static or flowing through the vessel. For example, such a calibration may be performed at the beginning of every cycle with the PD machine, or every time a door of the housing is closed. If at any point the baseline optical measurement exceeds a predetermined threshold, one or more of the patient, provider, and manufacturer may be notified to service and/or replace the patient monitoring device and/or fluid conduit as it may indicate calibration or device failure. Additionally or alternatively, the patient may be instructed to reduce the intensity of ambient light sources in the surrounding environment of the patient monitoring device.

In some variations, a baseline optical measurement may be performed when an empty vessel is first placed into the patient monitoring device. In other variations, a baseline optical measurement may be performed when a cycler is first set up and a cleaning fluid is primed through the drainage line. In some variations, a baseline optical measurement may be used to calibrate the patient monitoring device prior to measuring the patient effluent.

Particle Composition Estimation

In some variations, the particle composition of a patient fluid may be estimated based on measured optical characteristics of the patient fluid. For example, the type and/or concentration of particles (e.g., erythrocytes, leukocytes, triglycerides, protein, fibrin, etc.) in the patient fluid may be estimated based on optical measurements of particle settling characteristics of static patient fluid and/or optical measurements at a predetermined set of wavelength ranges.

In some variations, the estimated particle compensation may be used to improve the accuracy of detection of an infection state of the patient. For example, the characterization of particle composition using methods described below may be used to distinguish between "true positives" and "false positives" for infection state determination (e.g., false positives may be identified and excluded). For example, if the estimated turbidity calculated using one of the above-described turbidity equations exceeds a predetermined threshold corresponding to infection, but the estimated particle composition of the patient fluid is determined to be predominantly erythrocytes, then the prediction of infection may be considered a false positive.

Additionally or alternatively, the estimated particle compensation may be used to characterize the patient fluid and/or a patient status in other manners. For example, a determination that a patient fluid includes a high concentration of erythrocytes, the estimated turbidity of the patient fluid may be attributed to bleeding rather than leukocytes, rather than an infection.

Additionally, or alternatively, the particle type and/or concentration of particles in the patient fluid may be estimated by the changes successive sample measurements over time. For example, a patient may have five drainage sessions over a period of 24 hours. In the case of an infection, leukocyte counts may rapidly increase in concentration as part of a natural immune response. Therefore, measurement of successive samples may determine a rate of change in optical measurements characterized by a unique ramp-up profile of leukocytes corresponding to infection. In another example, triglyceride infusion may correspond to an acute, single measurement spike. Subsequent optical measurements may be characterized by a return to a low, normal baseline value. In yet another example, bleeding typically causes an immediate spike in measured fluid turbidity, and quickly reduces as clotting biological mechanisms take over.

Particle Settling

In some variations, a composition of a patient fluid may be estimated based on measured optical characteristics over time. For example, such optical characteristics of effluent dialysate may be measured during a CCPD exchange. In a typical CCPD exchange, there are three operational stages, including (1) filling the patient with dialysate fluid by feeding dialysate into a patient-entering line with a pump, (2) allowing the dialysate fluid to dwell in the patient while the pump is off, and (3) draining, in a drain cycle, effluent dialysate from the patient by feeding effluent dialysate into a drain line with the pump. The drain cycle typically includes several steps, including (3a) flushing prior fluid from the drain line, where the prior fluid may be effluent fluid, clean fluid from a prior priming and/or purging step, and/or some incidental new patient fluid, (3b) pumping new patient fluid into the drain line, and (3c) ceasing pumping and allowing the new patient fluid to become static in the drain line.

In some variations, one or more optical measurements may be performed during step (3b), when new patient fluid is being pumped through the drain line. For example, optical measurements may be performed at the beginning, middle, and end of this pumping cycle during step (3b), which may indicate how homogenous the new patient fluid is. Homogeneity, for example, may be estimated based on temporal uniformity of estimated turbidity as described above). Generally, bigger particles and clumps (e.g., fibrin) are likely to appear less homogenous than smaller particles like leukocytes. Thus, greater measured homogeneity may suggest a greater concentration of larger particles such as fibrin.

Figure 20:
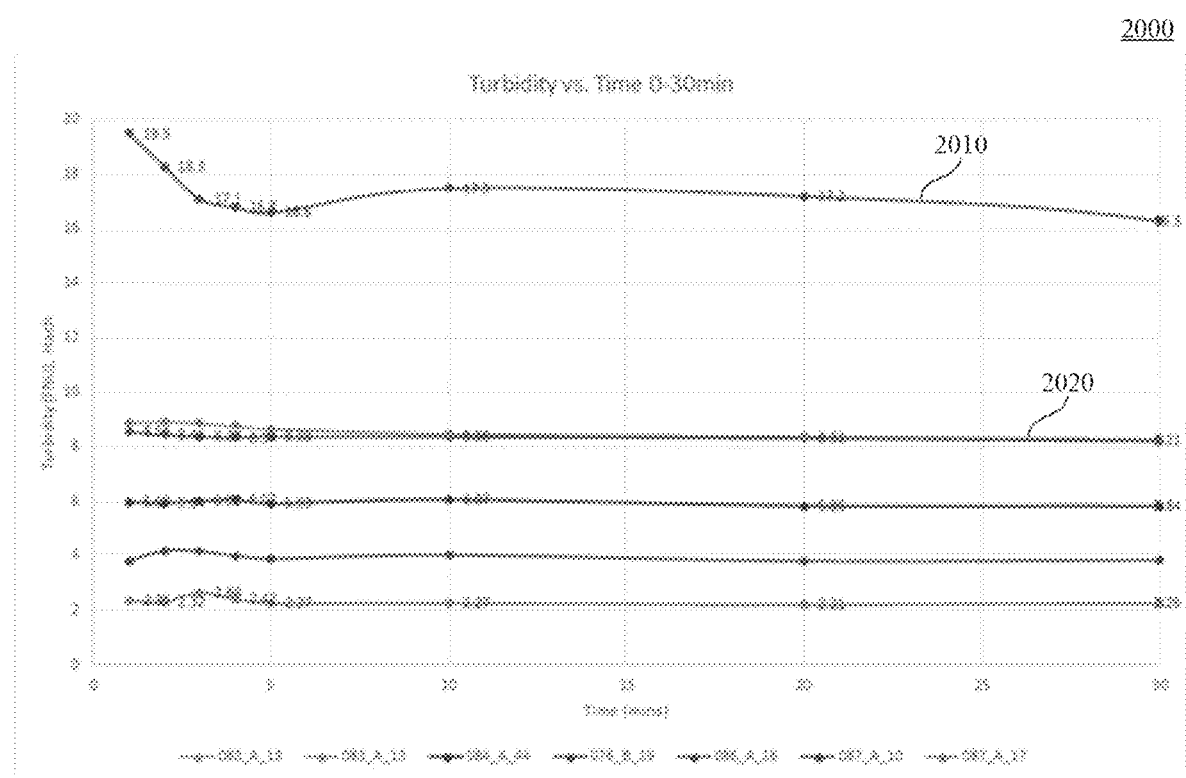
FIG. 20 is an illustrative graph of estimated turbidity plotted over time.

Additionally or alternatively, one or more optical measurements may be performed during step (3c), when the fluid flow of the new patient fluid ceases (e.g., a pump is turned OFF), and the new patient fluid becomes static in the drain line. From the point in time when the pump stops (time=0), optical characteristics of the patient fluid may be measured at predetermined intervals as the patient fluid settles. In some variations, the patient fluid may be measured at time=30 sec, 1 min, 2 min, 5 min, 15 min, 30 min, 60 min, and so on. Turbidity may be estimated using the measured signal data (as described above) at each predetermined interval. Particle properties including mass, buoyancy, density, size, shape, and the like affect the consistency and/or variance of turbidity measurements over time across these time series of measurements. That is, particle types exhibit unique settling properties. Accordingly, the type of particles dominant in a patient fluid may be estimated based on the settling characteristics of the patient fluid. For example, triglyceride content, having lower density than bodily cells, may remain suspended for relatively longer periods of time. Alternately, white blood cells, being larger and of different shape from red blood cells, may settle relatively faster. For example, FIG. 20 is a graph (2000) of turbidity of a set of exemplary settling patient fluids over time. In graph (2000), the difference in measured turbidity over time (which is a reflection of settling characteristics) of a first patient fluid (2010) and a second patient fluid (2020) suggest the first patient fluid (2010) and second patient fluid (2020) have different particle compositions.

System of Equations

In some variations, particle composition (e.g., particle concentrations) of a patient fluid may be estimated based at least in part on a system of equations using inputs including a set of optical measurements at a plurality of wavelength ranges. For example, optical characteristics (e.g., attenuation or scatter signal $A_{\lambda,n}$) of a patient fluid measured at four wavelength ranges ($\lambda_1$, $\lambda_2$, $\lambda_3$, $\lambda_4$) enables the particle concentrations of leukocytes, erythrocytes, protein (e.g., fibrin), and triglycerides ($\epsilon_l$, $\epsilon_e$, $\epsilon_p$, $\epsilon_t$) to be estimated using the below system of equations:

$$A_{\lambda_1} = c_l \epsilon_{l,\lambda_1} + c_e \epsilon_{e,\lambda_1} + c_p \epsilon_{p,\lambda_1} + c_t \epsilon_{t,\lambda_1}$$

$$A_{\lambda_2} = c_l \epsilon_{l,\lambda_2} + c_e \epsilon_{e,\lambda_2} + c_p \epsilon_{p,\lambda_2} + c_t \epsilon_{t,\lambda_2}$$

$$A_{\lambda_3} = c_l \epsilon_{l,\lambda_3} + c_e \epsilon_{e,\lambda_3} + c_p \epsilon_{p,\lambda_3} + c_t \epsilon_{t,\lambda_3}$$

$$A_{\lambda_4} = c_l \epsilon_{l,\lambda_4} + c_e \epsilon_{e,\lambda_4} + c_p \epsilon_{p,\lambda_4} + c_t \epsilon_{t,\lambda_4}$$

The optical characteristic $A_{\lambda,n}$ may be measured at each of a set of wavelengths $\lambda_1$, $\lambda_2$, $\lambda_3$, and $\lambda_4$. Coefficients $C_l$, $C_e$, $C_p$, and $C_t$, may be derived empirically through data models. Thus, for any given patient (or other) fluid, the system of equations may thus be solved for the particle concentrations ($\epsilon_l$, $\epsilon_e$, $\epsilon_p$, $\epsilon_t$).

In some variations, the set of wavelengths comprises a first wavelength between about 400 nm and about 450 nm (e.g., 415 nm), a second wavelength between about 500 nm and about 550 nm (e.g., 525 nm), a third wavelength between about 230 nm and about 290 nm (e.g., 260 nm), and a fourth wavelength between about 860 nm and about 890 nm (e.g., 870 nm). In some variations, the patient fluid may be illuminated sequentially at the four wavelength ranges in any predetermined order. Furthermore, illumination at these wavelengths may be provided by the same illumination sources as those providing for turbidity measurements as described above, or may be provided at least in part by a distinct and separate set of illumination sources.

FIGS. 23A-23D illustrates histograms (2300, 2310, 2320, 2330) of particle concentration estimation errors of four particle types for a set of patient fluid samples using the above-described system of equations approach. The particle concentrations were estimated based on the system of equations with four particles (leukocytes, erythrocytes, protein, triglycerides) measured at corresponding wavelengths (415 nm, 525 nm, 575 nm, 870 nm). The estimation errors were calculated by comparing the predicted particle concentrations against the actual particle concentrations determined using spectroscopy. As shown in FIGS. 23A-23D, the distributions of particle concentration estimation errors for the four particles types were generally centered around zero or a similarly low number, which suggests that the system of equations approach may be an accurate and viable way of estimating particle composition of a patient fluid.

Machine Learning

Additionally or alternatively, one or more trained machine learning models (or deep learning models, etc.) may be used to determine particle composition of patient fluid based at least in part on one or more measured optical characteristics, such as a light absorption pattern. For example, one or more suitable machine learning models may be trained on a suitable training data set including known particle concentrations, such that the trained machine learning model(s) may be able to identify a "signature" in the light absorption pattern suggesting a particle composition. Such optical characteristics may be measured at a single point in time, or dynamically to generate a time series of data. It should be understood also that any of the above-described variations of determining particle composition may be supplemented with suitable machine learning methods.

Patient Infection Onset and Resolution

In some variations, methods for predicting infection may include tracking a set of infection scores over time. A turbidity of the patient fluid may be estimated based on the measured optical characteristics, and infection scores may be generated based on the estimated turbidity (e.g., expressed in terms of NTU or similar units). In some variations, the estimated turbidity may be scaled to an infection score scale.

In some variations, an infection score (which may be generated for each PD cycle, or per day, etc.) may be compared to a set of predetermined infection onset criteria to predict onset of an infection state. For example, a positive infection state may be predicted in response to the infection score exceeding a predetermined threshold (e.g., over a predetermined number of consecutive positive infection samples) and/or increasing relative to a patient-specific baseline over time. For example, infection may be predicted in response to an infection score exceeding a predetermined threshold during each of one or more successive measurement time periods. In contrast, in some variations, an absence of infection may be predicted when the number of positive infection scores is below a predetermined threshold. In some variations, a false positive infection state may be identified when the infection score does not exceed the predetermined threshold over one or more successive measurement time periods. For example, a false positive may be identified if an infection score threshold is not met for three sample measurements in a row.

Figure 21A:
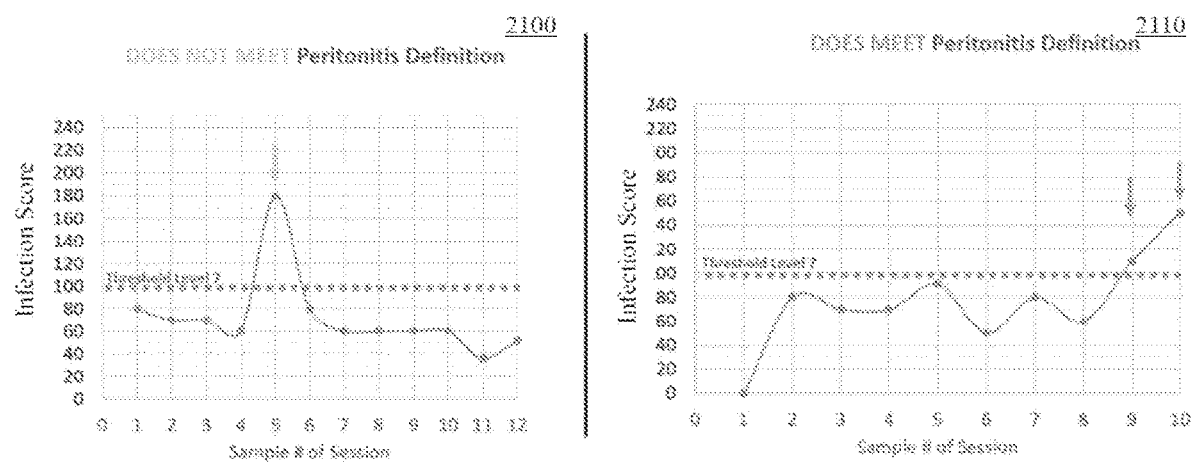
FIG. 21A depicts illustrative infection detection graphs of infection score plotted over time.

By tracking an infection score over time instead of relying upon a single, discrete sample, the sensitivity and specificity of an infection diagnosis may be improved by reducing false positives. For example, FIG. 21A illustrates infection detection graphs of an infection score plotted over time. An infection score of 100 may correspond to the International Society for Peritoneal Dialysis (ISPD) threshold for positive patient infection. The first graph (2100) shows that only one sample among twelve sequential samples has an infection score above the ISPD threshold. However, a single sample that exceeds the ISPD threshold may represent a false positive.

In contrast, in some variations of the methods and systems described herein, infection onset prediction criteria may comprise a number of infection scores above a predetermined threshold. Specifically, an onset of a positive infection state may be predicted when the number of consecutive positive infection scores is above the predetermined threshold (e.g., 2 samples). Additionally or alternatively, infection onset prediction criteria may comprise a sign and/or rate of change of the infection scores. For example, the second graph (2110) shows a plurality of samples having an infection score above the ISPD threshold. Furthermore, the samples above the ISPD threshold are sequential and have a positive slope such that the onset of infection state of the patient is predicted with high confidence. In some variations, an indication of the predicted infection state may be output to a patient using, for example, a display of a patient monitoring device and/or a GUI display on a computing device.

Figure 21B:
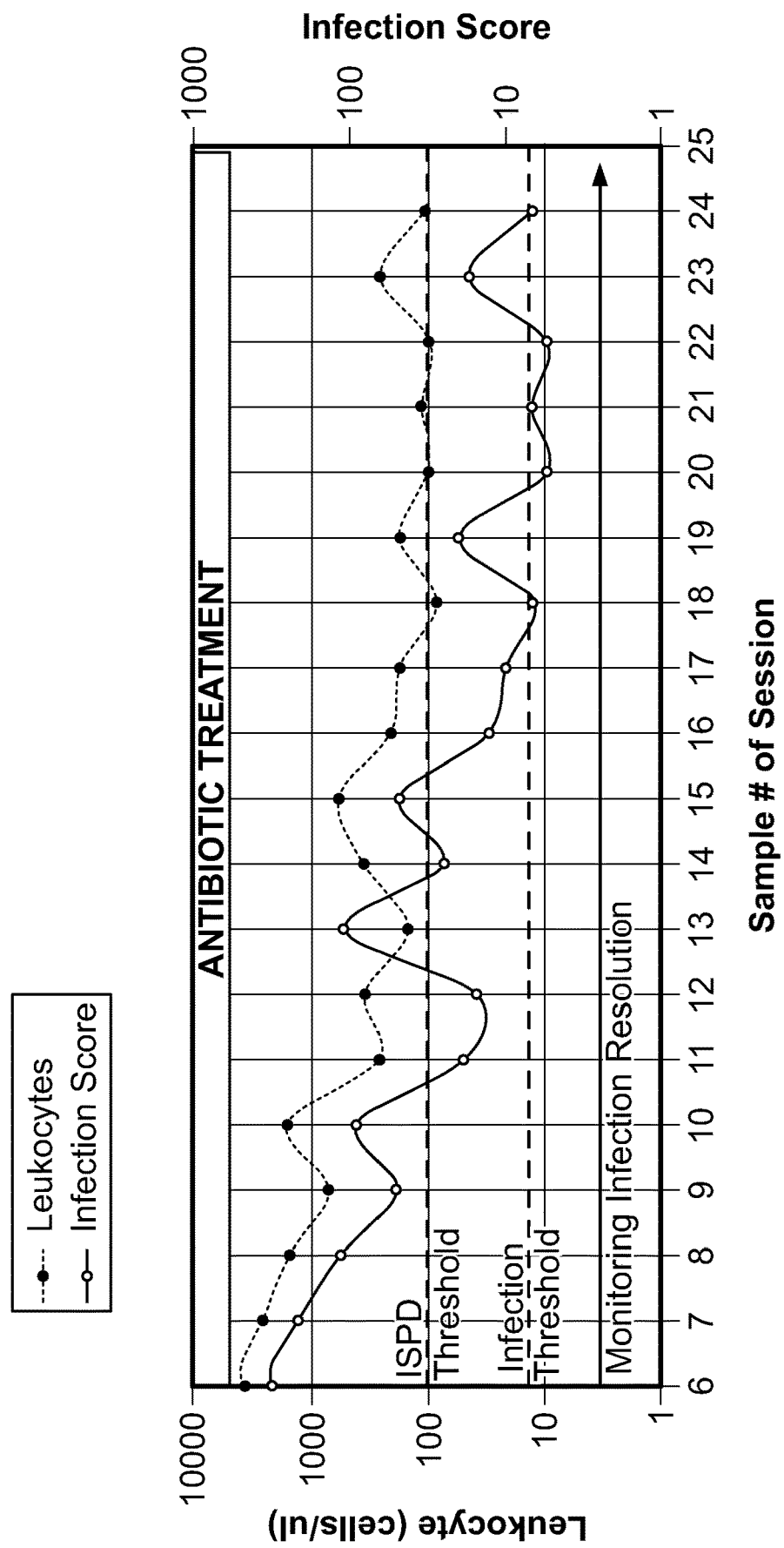
FIG. 21B is an illustrative infection detection graph of cell concentration and infection score plotted over time.

Additionally or alternatively, an infection score (which may be generated for each PD cycle, or per day, etc.) may be tracked to predict resolution of an infection state. For example, FIG. 21B is an infection detection graph (2120) of leukocyte concentration of patient fluid (as measured with a conventional method ("Leukocytes") and as estimated with infection scores as described herein ("Infection Score")) plotted over time for a patient receiving antimicrobial treatment. The infection score closely tracks the downward trend in measured leukocyte count, which helps indicate that the methods described herein may be used to predict infection resolution of a patient. Specifically, as shown in FIG. 21B, the actual leukocyte count of the patient initially exceeds the ISPD threshold for peritonitis. Over time, the leukocyte count decreases due to antimicrobial treatment and is maintained around the ISPD threshold of about 100 cells/µL. Similarly, a set of generated infection scores initially exceeds a predetermined threshold and then decreases until reaching an equilibrium state around a predetermined optical score threshold. Therefore, the correlation between an infection score and leukocyte count suggests that the infection score may be a proxy for leukocyte count.

In some variations, a set of criteria (e.g., threshold, parameters) used to predict infection may be generated based on one or more machine learning techniques such a random forest model. In some variations, the set of predetermined criteria may be generated based on multi-target linear regression that relates a set of inputs (e.g., 90 degree- and 180 degree-offset light intensity measurements at three wavelengths for a predetermined number of samples). to the concentration or leukocytes, erythrocytes, triglycerides, proteins and more. These continuous variable predictions may be converted to binary outcomes (negative infection, positive infection) based on a set infection thresholds.

In some variations, the set of predetermined criteria may be generated based on single-target random forest classification that relates a set of inputs to a single binary target. An infection threshold may be initially defined by a leukocyte concentration of about 100 cells/µL and/or a polymorphonuclear cells family (PMN) neutrophil concentration of about 50%. Additionally or alternatively, methods and devices described herein may be used with any data modeling and/or machine learning algorithm and/or model, including but not limited to multi-target regression and classification, decision tree models, deep neural network models, Bayesian networks, clustering models, and/or other algorithms and/or models.

Fluid Flow Estimation

In some variations, estimating a fluid flow rate (e.g., flow ON, flow OFF) of patient fluid through a fluid conduit may enable independent determination of an operating state (e.g., pumping state) of a cycler, such as to determine when a unique drain cycle has begun and ceased (and initiate the optical measurement of the fluid). Furthermore, power consumption and optical sensor usage of a patient monitoring device may be optimized based on a flow state of the patient fluid. For example, the optical sensor may measure patient fluid more frequently when the night cycler is pumping new fluid through a fluid conduit and reduce optical sensor usage when patient fluid is static in the fluid conduit. This may increase a lifespan of one or more components of the patient monitoring device such as an illumination source. In some variations, one or more fluid flow estimation methods may be selected based on predetermined conditions (e.g., power state, schedule, processing load). As another example, knowledge of the fluid flow rate (ON or OFF) may be used to coordinate processes for estimating particle concentrations in the patient fluid based on particle settling characteristics (when the cycler pump is OFF), as described above.

In some variations, a fluid flow rate of patient fluid may be estimated based on one or more optical measurements of the patient fluid using the optical sensors described herein. For example, one or more 180 degree scatter angle light intensity measurements of the patient fluid may be measured when estimating fluid flow rate, as a 180 degree measurement may have a relatively high signal-to-noise ratio when compared to scatter signals at other angles. In some variations, the patient fluid may be sampled at a rate of about 50 Hz to reduce aliasing.

Figure 22A:
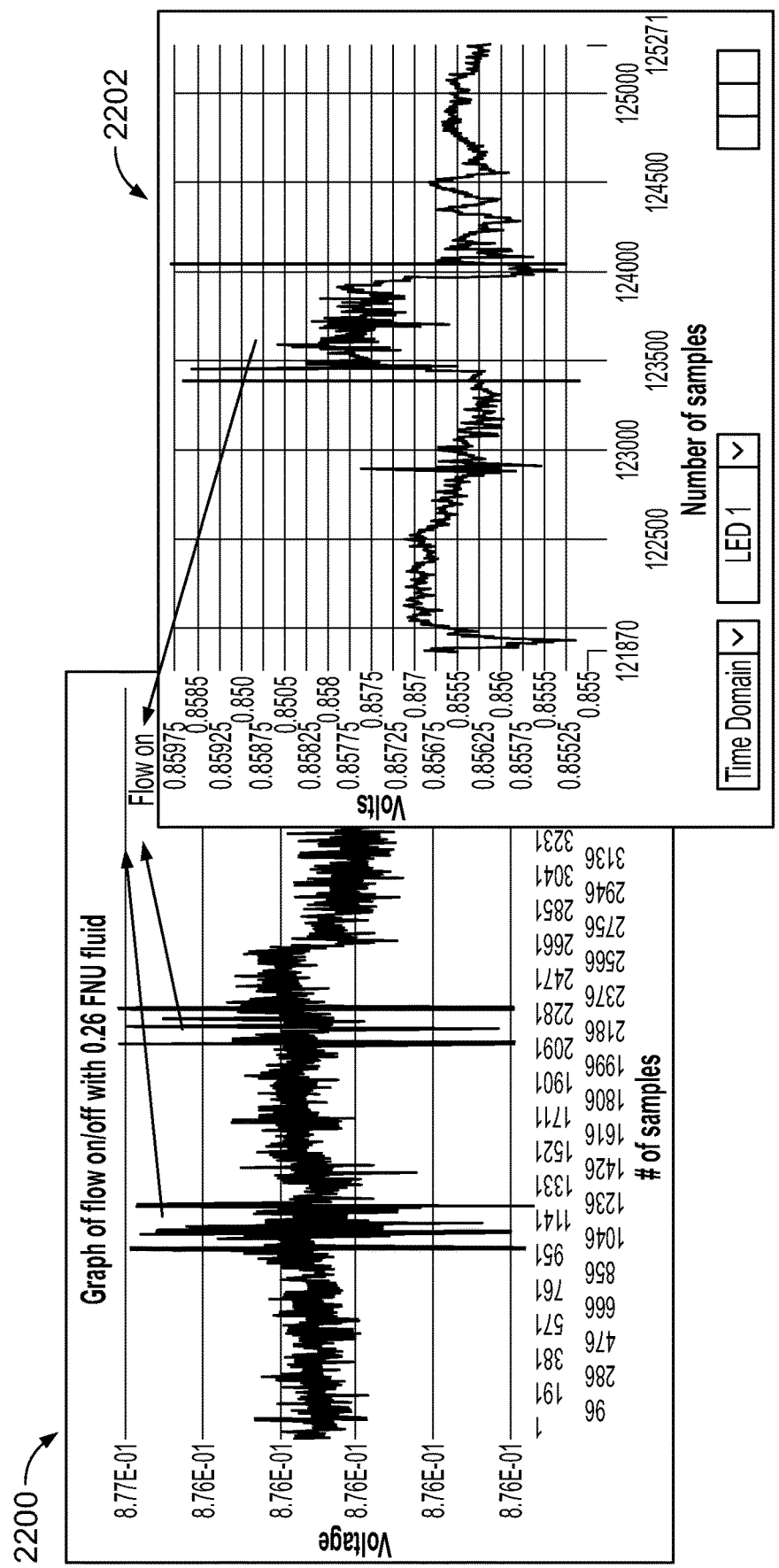
FIGS. 22A and 22B are illustrative fluid flow graphs of optical sensor measurements plotted over time and a corresponding frequency response plot.
Figure 22B:
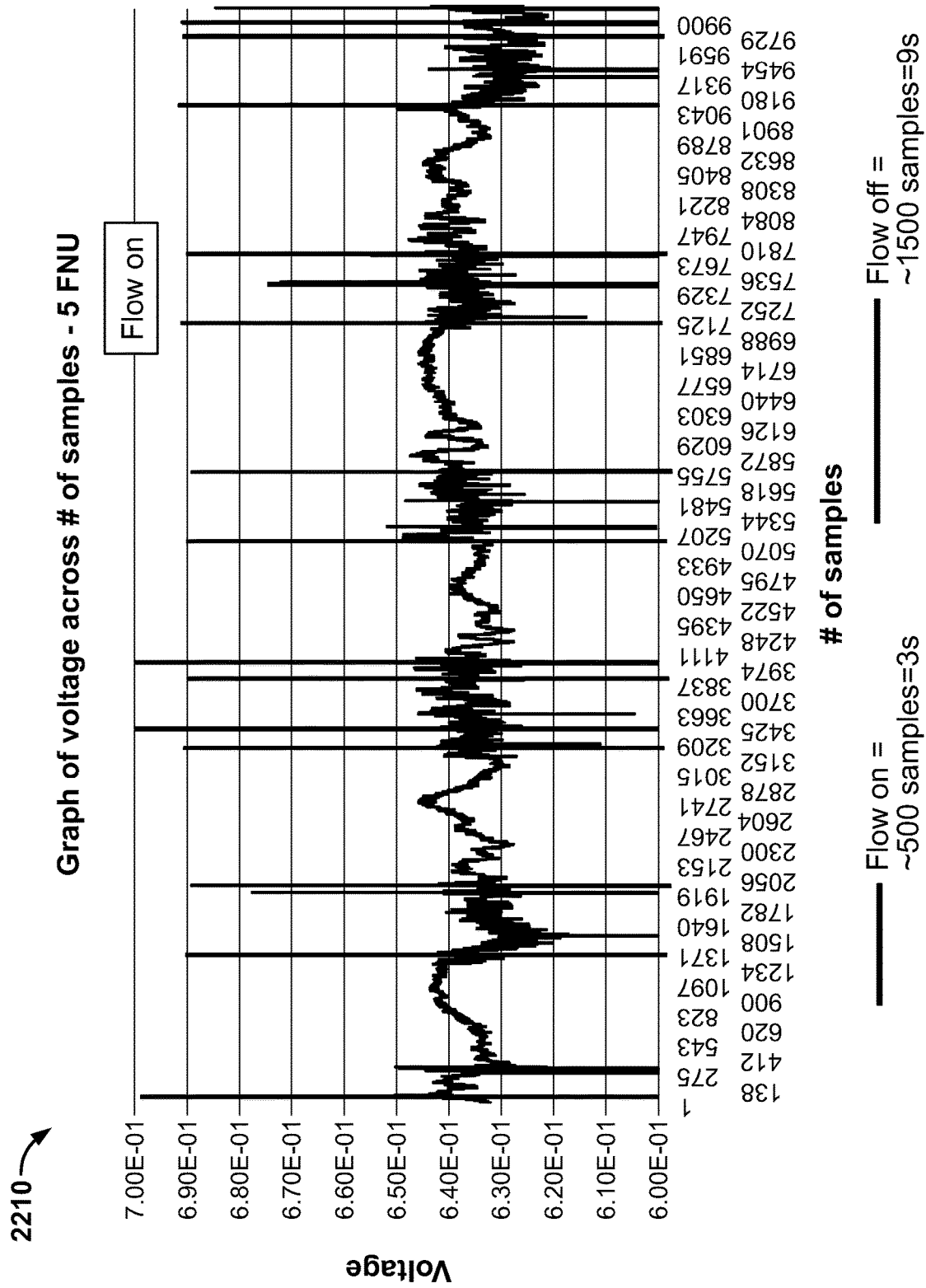
Figure 23A:
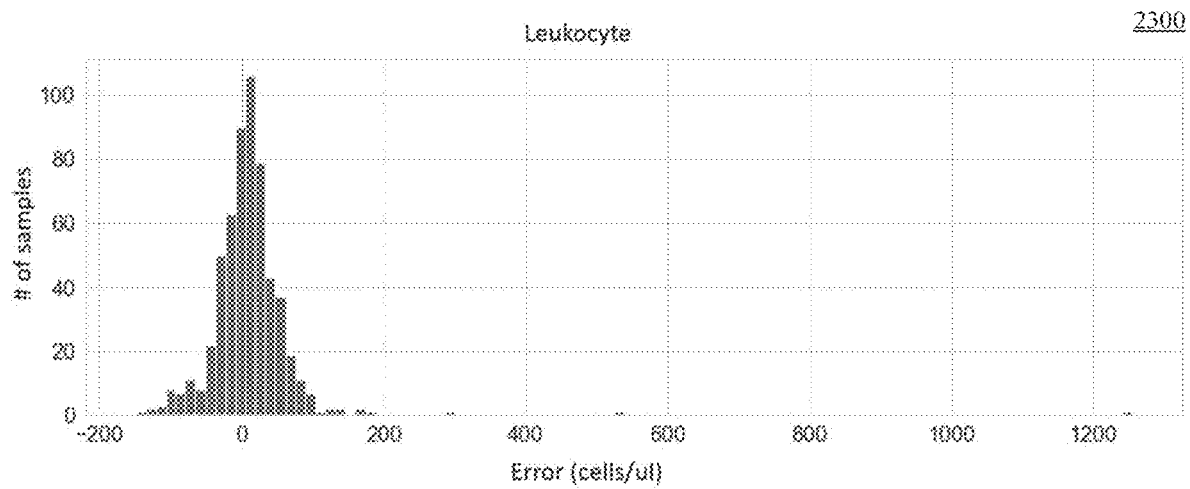
FIGS. 23A, 23B, 23C, and 23D are illustrative error measurement graphs for respective leukocytes, erythrocytes, proteins, and triglycerides.
Figure 23B:
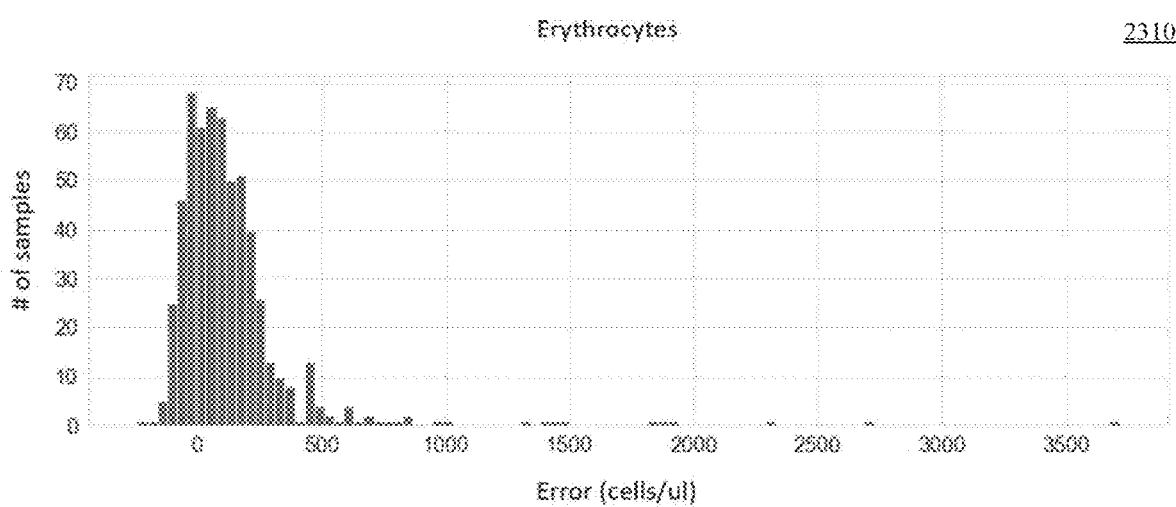
Figure 23C:
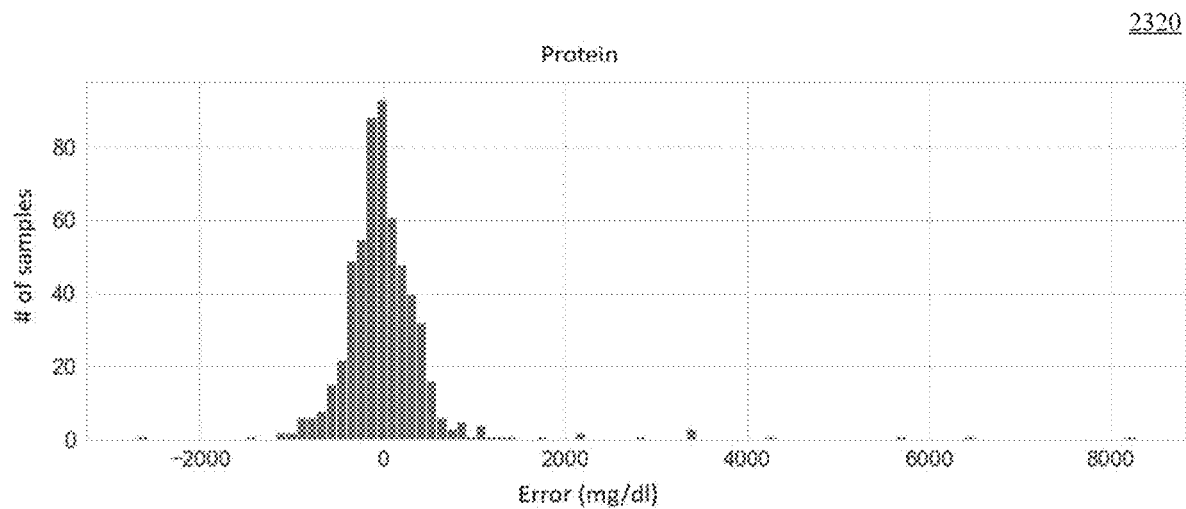
Figure 23D:
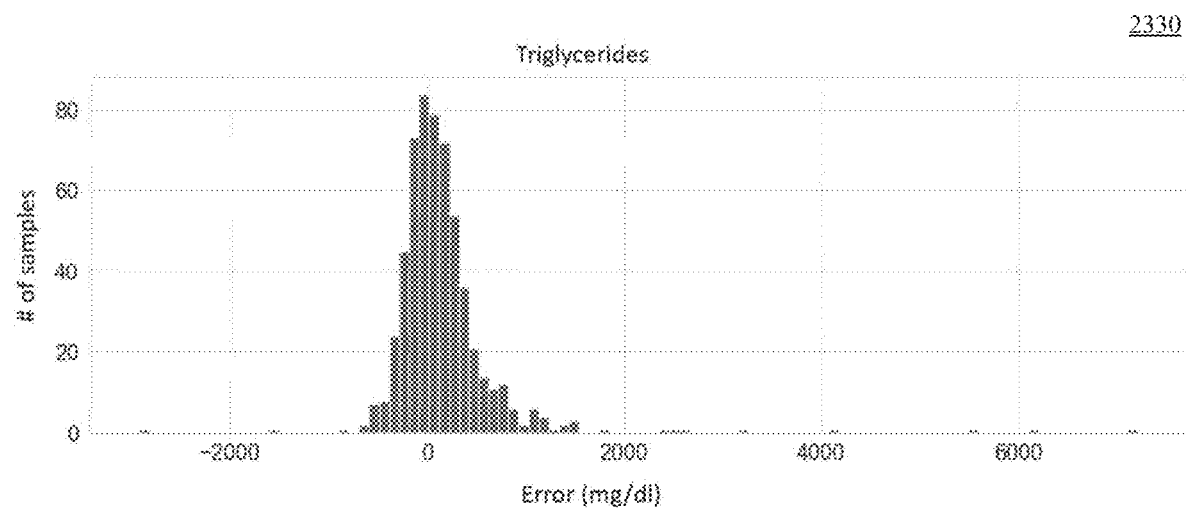

A frequency response of the optical measurement(s) may then be generated and used to estimate the fluid flow rate. For example, a Fast Fourier Transform (FFT) may be applied to a set of optical measurements to determine whether the frequency of the pulse signal in the optical measurement(s) is approximating a known pump frequency of the cycler. For example, conventional cyclers may pump fluid with a flow ON/OFF cycling frequency of between about 0.05 Hz to about 2 Hz. FIGS. 22A and 22B are fluid flow graphs (2200, 2202, 2210) of optical sensor measurements of fluid plotted over. The optical measurements comprise variable fluid flow rates (ON, OFF) due to cycler pumping. For example, the flow ON intervals are annotated in each of FIGS. 22A and 22B. Independently, a Fast Fourier Transform (FFT) may be applied to the set of optical measurements to determine whether at any measured point(s) in time the frequency of the optical measurement signal (voltage) is between about 0.05 Hz and about 0.2 Hz, which can be used to indicate the occurrence of a flow ON interval. Conversely, the FFT may be used to determine whether the frequency of the optical measurement signal is not between about 0.05 Hz and about 0.2 Hz, which can be used to indicate the occurrence of a flow OFF interval.

In some variations, a fluid flow rate of patient fluid may be estimated using one or more filters. For example, a fluid flow rate may be estimated using one or more low pass filters and/or high pass filters. Fluid flow estimation based on low pass and/or high pass filters may reduce computational load relative to, for example, FFT based fluid flow estimation algorithms. For example, a low pass filter may comprise a frequency between about 75 Hz and about 90 Hz, and a high pass filter may comprise a frequency between about 50 Hz and about 70 Hz. The optical measurement signal passed through one or more of the filters may be analyzed to determine a fluid flow ON/OFF state. For example, a filtered signal comprising a predetermined number of pulses (e.g., 3 pulses) above a predetermined threshold may correspond to a fluid flow ON state.

Thus, in some variations, an ON or OFF fluid flow state may be determined based on the estimated fluid flow rate. In some variations, the patient fluid may be illuminated and measured in response to detecting the ON state (such as to estimate turbidity) and illumination may be ceased in response to detecting the OFF state (to conserve energy). This may reduce power consumption and increase a lifespan of an illumination source by reducing unnecessary and/or constant optical measurements.

For example, optical measurements for fluid flow rate estimation may be performed at predetermined intervals. For example, such optical measurements may be performed for about thirty seconds in a "listening" state. If the flow is off, then a follow-up set of optical measurements for fluid flow rate estimation may repeat after another predetermined rest interval, such as five minutes. However, if flow is ON, then optical measurements may be performed for turbidity estimation such as by using methods described above.

As another example, the patient fluid may be measured and fluid flow rate may be estimated at predetermined intervals throughout a drain cycle. For example, the predetermined intervals may comprise the beginning, middle, and end of new fluid pumping through the fluid conduit during a drain cycle. In some cases, the predetermined intervals may comprise a set of intervals (e.g., 1 minute, 2 minutes, 3 minutes, 4, minutes, 5 minutes, 10 minutes, etc.) when new fluid becomes static in the fluid conduit. Additionally or alternatively, fluid flow rate may be estimated using one or more non-optical sensors. For example, an accelerometer may be configured to measure vibrations of the fluid conduit corresponding to a fluid flow state. As another example, a pressure sensor may be configured to measure periodic or intermittent pressure cycling within a fluidic conduit. As another example, a microphone may be configured to measure audio corresponding to pump operation.

In some variations, the system may be configured to distinguish between a true fluid flow ON state and a "false positive" fluid flow ON state, such as during one or more cycler setup steps. For example, a false positive fluid flow ON state may be generated due to a priming step of a CCPD exchange where fluid intermittently flows through a drain line. Because measurement and sensing during such a priming step (or after any other brief fluid flow not part of a drain cycle) utilizes the device unnecessarily, identification of such false positive fluid flow may help optimize device resources and/or usage life (e.g., reduce power consumption, reduce memory storage use, reduce unnecessary consumption of optical sensor lifetime, etc.). In some variations, a false positive fluid flow ON state may be identified based on detecting one or more of a predetermined number of measured pump pulses over a predetermined duration of fluid flow. Additionally or alternatively, in some variations, a false positive may be identified when a fluid flow ON state is not identified over two or more successive time periods. For example, a measurement of three pump pulses within a first measurement time period having a duration of about 30 seconds may correspond to a fluid flow ON state. However, a false positive may be identified if a pump pulse threshold is not met (e.g., three pulses) within a second measurement time period having a duration of about 30 seconds measured after the first time period. In some variations, a predetermined test delay time period (e.g., 30 seconds) may be applied between the first time period and second time period measurements. If pulses are detected and a false positive fluid flow ON state has not been identified, the system may proceed with the assumption that the fluid flow is indeed in the ON state, and subsequent optical characteristics of the fluid may be measured and analyzed as described herein.

In some variations, a measurement time period as described above (e.g., first measurement time period, second measurement time period) may be between about 10 seconds and about 15 minutes, between about 20 seconds and 5 minutes, between about 20 seconds and about 2 minutes, between about 20 seconds and about 1 minute, between about 20 seconds and 40 seconds, including all ranges and sub-values in-between. In some variations, a test delay time period may be between about 10 seconds and about 15 minutes, between about 20 seconds and 5 minutes, between about 20 seconds and about 2 minutes, between about 20 seconds and about 1 minute, between about 20 seconds and 40 seconds, including all ranges and sub-values in-between.

Bubble Detection

Figure 24:
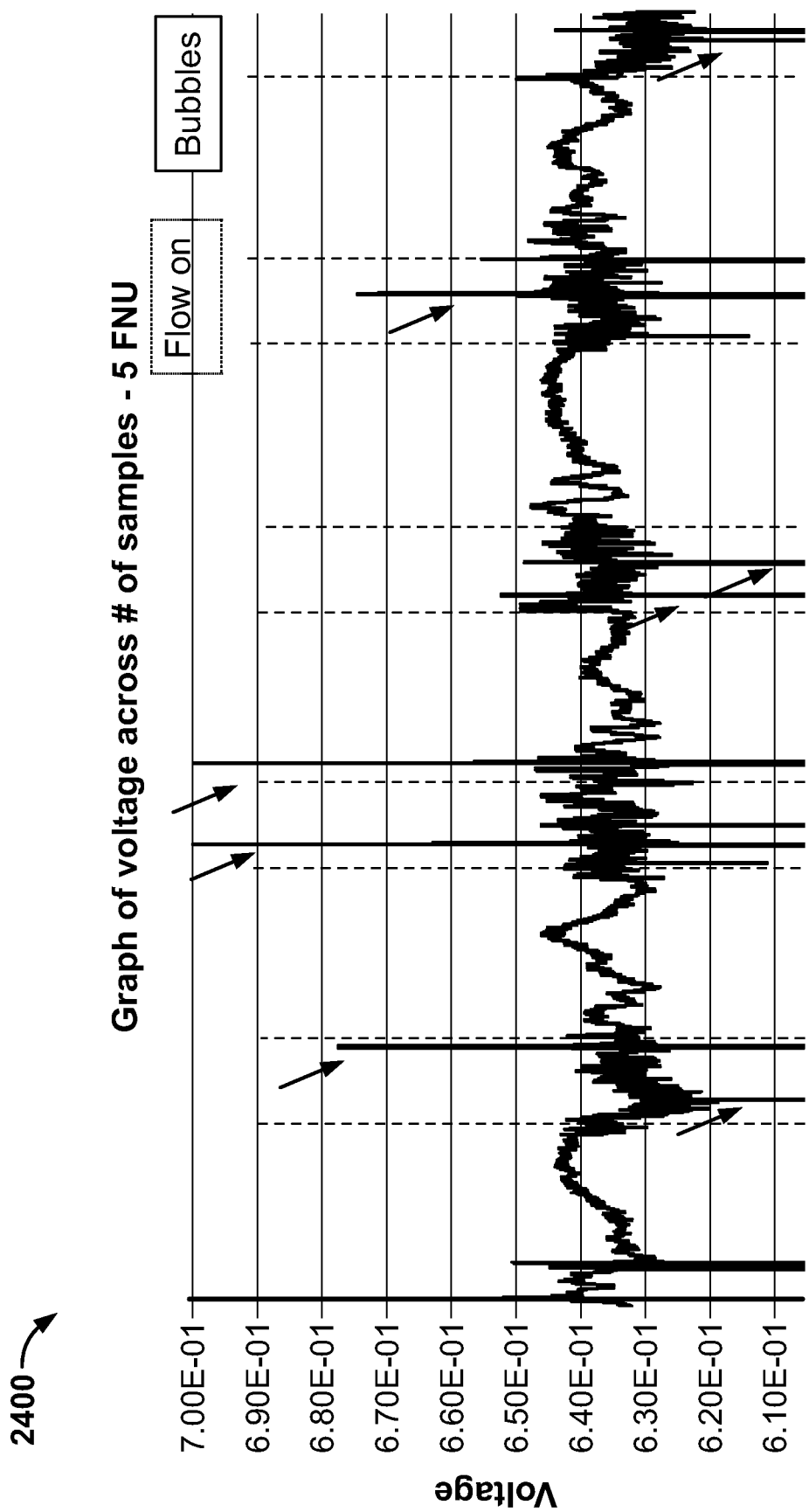
FIG. 24 is an illustrative graph of optical sensor measurements plotted over time for depiction of bubbles.

In some variations, the patient fluid may comprise non-homogenous objects such as bubbles that add noise to optical measurements and subsequent fluid analysis. In some variations, bubbles in the fluid conduit may be detected based at least in part on optical measurements using the sensors described herein. FIG. 24 is a bubble graph (2300) of optical sensor measurements plotted over time. For example, the flow ON intervals and bubbles are annotated in FIG. 24. In some variations, a frequency response of the optical measurement may be used to detect bubbles. For example, a Fast Fourier Transform (FFT) may be applied to the optical measurement to generate a corresponding frequency response plot (not shown). Furthermore, a filter (e.g., low pass filter) may be applied to differentiate bubbles from flow ON/OFF transitions. Patient fluid including any detected bubbles may be excluded from analysis for infection, etc. In some variations, a patient may be notified of and/or instructed to remove the bubbles in the fluid conduit.

Other Monitoring Applications

In some variations, methods for predicting an immune response of the patient may be based at least in part on the measured optical characteristics. For example, an increased leukocyte count may indicate comorbidities causing a high immune response not limited to infections, such as from cancer. Immune responses due to different sources typically corresponds to a unique differential count profile of one or more types of leukocytes. Infections, for example, have a higher polymorphonuclear cell differential count. The optical characteristics of polymorphonuclear cells vary from other types of leukocytes, such as eosinophils and basophils, which have different sizes and/or shapes. Thus, optical profiles for specific leukocyte types may aid in diagnosis of the root cause of elevated leukocyte levels.

In some variations, methods for predicting bleeding of the patient may be based on the measured optical characteristics. For example, an overall turbidity of patient fluid measured above a first predetermined threshold in combination with an estimated leukocyte count below a second predetermined threshold may indicate bleeding. The overall turbidity may be measured at a non-cell-specific wavelength (e.g., 800-900 nm) and the estimated leukocyte count may be measured based on optical measurements taken at a leukocyte-specific wavelength range. In some variations, one or more of the patient and provider may be notified of possible bleeding.

In some variations, methods for predicting a fibrin concentration may be based on the measured optical characteristics. For example, high variance optical measurements may indicate large particulate matter (e.g., solids, clumps, chunks) present in the patient fluid. High fibrin content may increase a risk of clogging of the fluid conduit.

In some variations, methods for predicting an infection onset for an ascites drainage patient may be based the measured optical characteristics. Ascites drainage involves either a permanently affixed device (e.g., a peritoneal port or catheter or central venous catheter) or temporarily invasive hospital procedures, such as large volume paracentesis.

Catheter leakage or obstruction may be detected by the flow rate or pressure of the drainage compared to a baseline. For patients with frequent ascites drainage (e.g., more than once a week), a patient-specific baseline may be developed over about 3 months or after about 25 drainage sessions are measured. For patients with less frequent drainage, such as on a monthly basis, then comparing the characteristics of the drainage of the patient against a population baseline may be more practical. For less frequently drained individuals, data could still be collected to establish an individualized baseline. When a patient monitoring device is attached to a drainage line, an infection may be monitored via measurement of the patient fluid and comparing this to the baseline values of the individual patient.

Remote Monitoring and Clinical Workflow

In some variations, a medical care provider may remotely monitor patients using methods and systems such as those described herein, which may enable early detection and treatment of patients (e.g., with antibiotics for infection treatment, other antimicrobial, etc.). Such early detection and treatment may in turn help avoid progression of infection and/or other conditions, thereby reducing infection-driven hospitalization. Although the below description refers primarily to a treatment regimen including administration of an antibiotic, it should be understood that similarly such remote monitoring may be performed with respect to a treatment regimen including administration of any suitable antimicrobial (e.g., antibiotic, antifungal, antiviral, etc.).

Figure 27A:
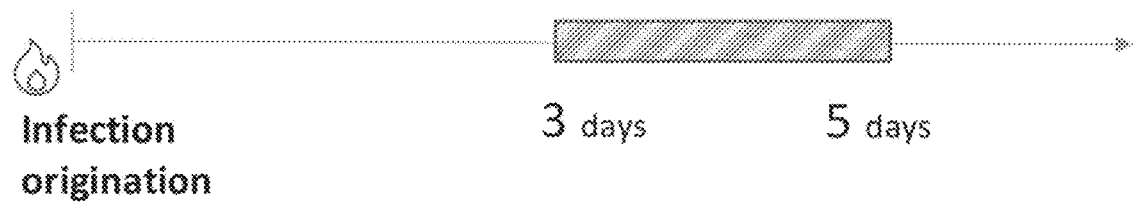
FIG. 27A is a schematic diagram of an illustrative clinical workflow in convention standard of care.

For example, FIG. 27A illustrates a typical timeline for conventional standard of care for a patient with peritonitis. Typically, a patient contacts their medical care provider upon noticing a visibly cloudy sample of effluent dialysate (e.g., as suspected as the result of a "newspaper" test in which a written text sample is not easily visible through a volume of effluent dialysate). The point at which effluent dialysate is visibly cloudy is typically 3-5 days after infection has originated, and in response the medical care provider typically prescribes a single broad spectrum antibiotic treatment to address the progressed infection. However, this approach has a limited success rate of about 72%, as about 28% of patients still end up hospitalized as a result of a failed antibiotic treatment. Furthermore, hospitalization mortality rate among such hospitalized patients is about 3.5%. Thus, the conventional standard of care not only relies upon patient compliance to actively monitor for visibly cloudiness of their samples, but also still leads to a significant portion of the patient population experiencing adverse patient outcomes such as hospitalization or even death.

Figure 27B:
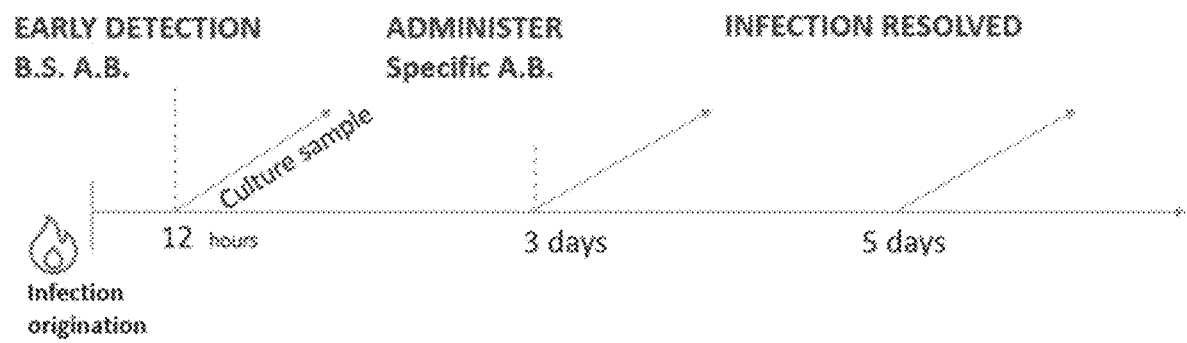
FIG. 27B is a schematic diagram of an illustrative clinical workflow using systems and methods described herein.

In contrast, remote patient monitoring using methods and systems described herein may be used to effectively detect infection soon after infection origination and permit prompt courses of action to prevent progression of infection and other conditions. For example, as illustrated in FIG. 27B, a medical care provider may receive a notification of a predicted patient infection state (e.g., probability of infection) in about 8-12 hours after infection origination. The patient is then prompted (or taken) into the clinic for culture sample withdrawal, and receives antibiotic treatment (e.g., broad spectrum antibiotic), similar to what typically occurs 3-5 days later under conventional standard of care. After the administration of broad spectrum antibiotic, the patient may continue dialyzing at home, and efficacy of the antibiotic may be remotely monitored as described above. In other words, the medical care provider may be able to determine remotely whether the broad spectrum antibiotic was successful in treating the infection. The success rate for the broad spectrum antibiotic generally is greater if administered earlier rather than later, so such early detection provided by the methods and systems described herein helps efficacy of the broad spectrum antibiotic. If the patient was successfully treated with the broad spectrum antibiotic, then the patient may be classified as healthy (e.g., case is resolved). If the patient's infection appears to continue to progress (e.g., determined using methods and systems described herein), then results from the culture sample (e.g., between about 36 hours-48 hours after infection origination) may be used by the medical care provider to shift treatment toward a more targeted or specific antibiotic. At this point in the clinical workflow, the patient's infection may be combated with a specific antibiotic sooner after infection origination, compared to conventional standard of care where the first treatment steps were delayed due to delayed infection detection.

During the administration of a specific antibiotic, the patient may again continue dialyzing at home, and efficacy of the antibiotic may be continued to be remotely monitored as described above. In other words, the patient's medical care provider may continue to monitor the patient's infection state (e.g., based on the real-time, device-generated infection score) to confirm whether the infection subsides. If the infection is bacterial, then the patient's infection is expected to be resolves given the specificity of the antibiotic (e.g., around 5 days after infection origination, depending on resilience of bacteria, etc.). Only fungal infections, which are nonresponsive to antibiotics, are expected to lead to a hospitalization. Thus, remote patient monitoring using methods and systems described herein may be used to address patient bacterial infections early and effectively, leaving only a small proportion of fungal infection patients (around 3% of cases) requiring more drastic treatments such as hospitalization.

Figure 28:
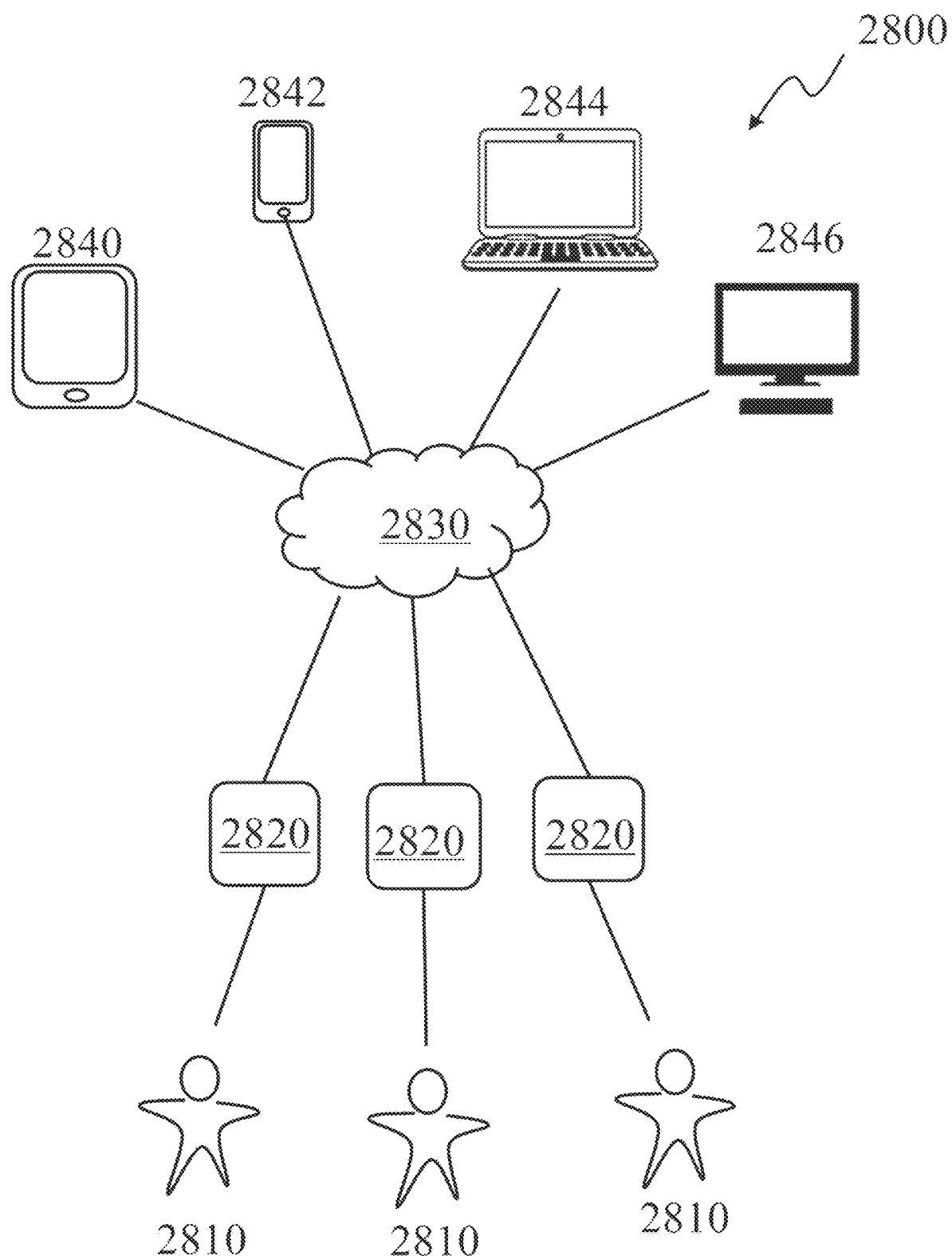
FIG. 28 is a schematic diagram of a system for patient monitoring including one or more patient monitoring devices such as that described herein.

FIG. 28 illustrates a system implemented in a clinical workflow using methods and systems described herein. Generally, a system (2800) for monitoring patients (2810) may include a patient monitoring device (2820) that interfaces with the patient (2810) and may be configured to communicate in a wireless or wired manner with a network (2830) (e.g., cloud-based network or other suitable network of computing device), such that data received from the patient monitoring device (2820) may be analyzed remotely (non-locally) from the patient. Multiple patients (2810) may each have their own patient monitoring device (2820) that communicates in this manner. Alternatively, some patients may share a patient monitoring device (2820) (e.g., multiple patients in a single household), where data from different patients may be distinguished using patient identification info or the like. Alternatively, data from the patient monitoring device (2820) may be communicated to one or more intervening computing devices (not shown) which in turn may communicate data to the network (2830). Furthermore, in some variations, data may be analyzed locally by one or more processors on the intervening computing device(s). Patient data (and/or information derived from the medical-related data) received by the network may be stored, for example, on one or more servers.

In some variations, patient data (and/or information derived from the patient data) may be accessible by one or more third party computing devices. For example, as shown in FIG. 28, such data or information may be accessible by a third party computer device (e.g., tablet (2840), mobile phone (2842), laptop computer (2844), desktop computer (2846), etc.) that is in communication with the network (2830). It should also be understood that any other computing device operated by the patient may similarly access the information over the network (2830). For example, in some variations, a user (e.g., medical care provider, patient, etc.) may access and/or be notified of patient data through a portal or other suitable graphical user interface. The information (and use thereof) that may be accessible to other computing devices is further described below.

Figure 29:
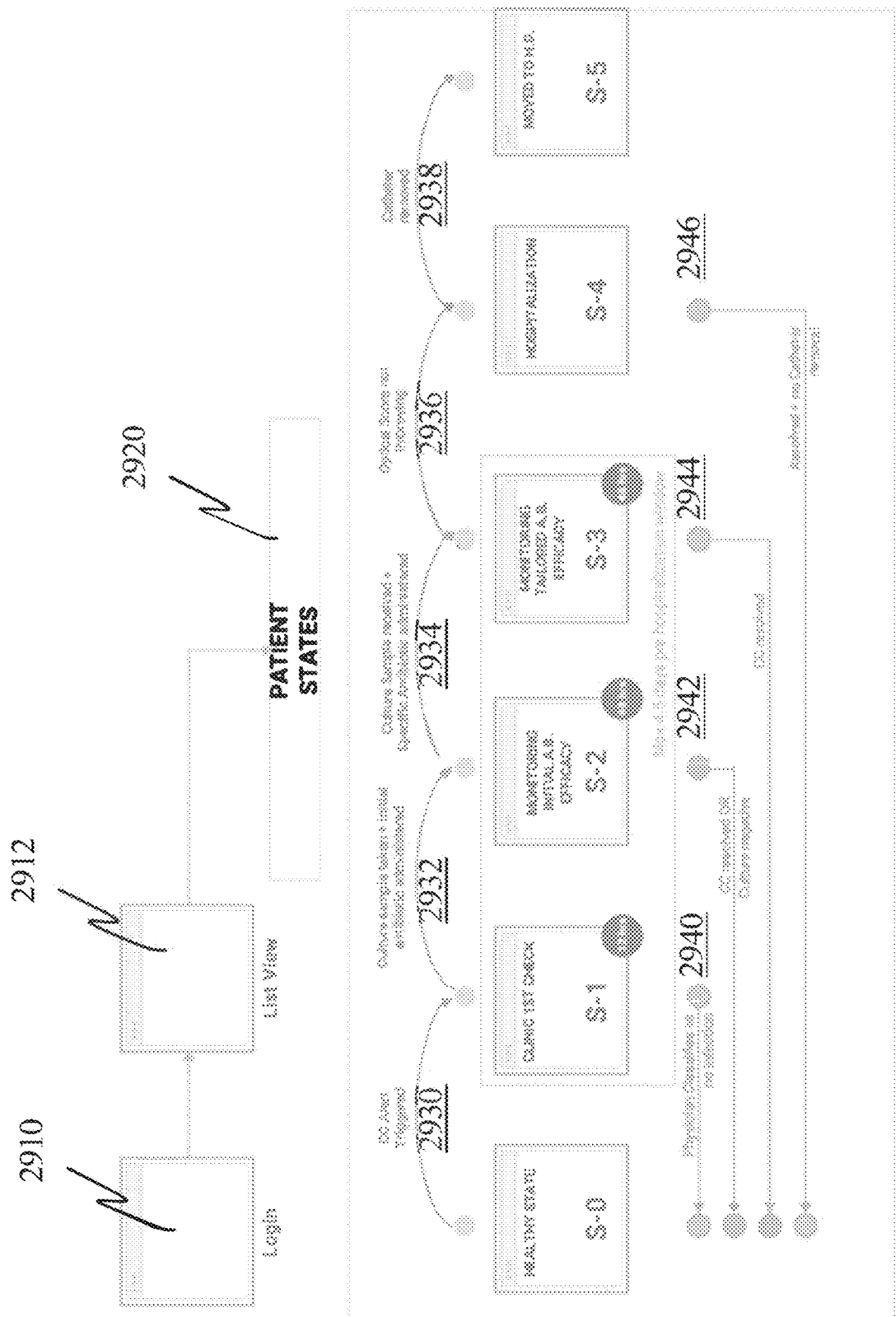
FIG. 29 is a schematic diagram of patient stages in an illustrative variation of a patient state diagram.

FIG. 29 illustrates, in more detail, a state-based clinical workflow using methods and systems described herein. Patient states and other patient information may be tracked through a graphical user interface (GUI) to permit a user such as a medical care provider to manage remotely monitored patients. For example, as shown in FIG. 29, the user may access a database of patients using a login (2910) (e.g., user ID and password, other suitable authentication schemes, etc.). A list of accessible patients (2912) may be provided to the user for selection and viewing of information (e.g., name, contact info, medical history, current medications, predicted infection status, etc.) associated with those patients. The patients that are accessible to the user may be personalized or otherwise limited. For example, a user who is a medical care provider (e.g., doctor or clinic administrator) may be limited to access a patient list (2912) including only patients under his or her care. As another example, a user associated with a medical institution (e.g., clinic) may be limited to access a patient list (2912) including patients receiving treatment at the medical institution. The patient list (2912) may be filtered based on factors such as patient personal characteristics (e.g., age, sex, duration of PD treatment, frequency of infection, etc.) and/or patient states (2920) or other patient statuses (e.g., as described in further detail below). Furthermore, the GUI and/or other communication system may provide notifications and/or enable note-taking relating to patient status.

FIG. 29 also illustrates an exemplary state diagram of multiple patient states referred to herein as Stage S-0 to Stage S-5. A patient may generally progress from Stage S-0 to Stage S-5 as their condition worsens (e.g., as infection increases).

Stage S-0 corresponds to a healthy patient state (e.g., no infection predicted). An infection of the patient may be predicted (e.g., using the devices and methods described herein), which moves the patient from Stage S-0 ("HEALTHY STATE") to Stage S-1 ("CLINIC $1^{ST}$ CHECK") relating to a patient state requiring an initial clinic check. In some variations, the transition (2930) between Stage S-0 to Stage S-1 may occur about 8-12 hours after infection origination.

When in Stage S-1, the patient may be brought into the clinic within about 12 hours for a culture sample withdrawal. The patient may be tested at the clinic for infection. If there is no infection, then patient may return to Stage S-0 (2940). If there is an infection, the patient may receive broad spectrum antibiotic, along with any other suitable initial treatments. After receiving initial antibiotic treatment, the patient may be moved (2932) to Stage S-2 ("MONITORING INITIAL A.B. EFFICACY").

During Stage S-2, the patient may spend a period of time (e.g., 48 hours) at home dialyzing and using patient monitoring devices and methods described herein. A medical care provider may remotely determine whether the broad spectrum antibiotic was successful at resolving the infection (e.g., tracking infection score). If the infection becomes resolved (e.g., based on decreasing trend in infection score), then the patient may return (2942) to Stage S-0. If the infection appears to progress (e.g., based on increasing trend in infection score), then the patient may receive a more targeted or specific antibiotic (e.g., after a 48-hour period). The specific antibiotic may be determined based at least in part on the culture sample results for the patient. In some variations, if the culture sample results suggest a fungal infection, the patient may be moved directly to Stage S-4 (described below), such as at the discretion of the medical care procedure. Otherwise, after receiving a specific antibiotic, the patient may be moved (2934) to Stage S-3 ("MONITORING TAILORED A.B. EFFICACY")

During Stage S-3, the patient may be at home dialyzing and using patient monitoring systems and methods described herein. During this time, similar to Stage S-2, a medical care provider may remotely determine whether the specific antibiotic was successful at resolving the infection (e.g., tracking infection score). In many cases, given the specificity of the antibiotic administered, the patient's infection will become resolved (e.g., reflected in decreasing trend in infection score). If the infection becomes resolved, then the patient may return (2944) to Stage S-0. If the infection, however, continues to progress (e.g., based on increasing trend in infection score), then the patient may become hospitalized and be moved (2936) to Stage S-4 ("HOSPITALIZATION"). In many cases, only fungal infections may lead to patient hospitalization.

While in Stage S-4, the patient may receive suitable hospital treatment. If the patient's infection becomes resolved (e.g., as determined by medical care provider(s)), then the patient may return (2046) to Stage S-0. If the infection, however, continues to progress (e.g., as determined by medical care provider(s)) and catheter removal is determined to be necessary, then the patient's catheter may be removed and the patient may be moved (2938) to Stage S-5 ("MOVED TO H.D.") for hemodialysis. In some variations, the shift to Stage S-5 for hemodialysis treatment may be permanent, and patients in Stage S-5 might not return to peritoneal dialysis. For example, patients permanently classified as Stage S-5 may be classified in the patient monitoring system as a former patient or the like.

Thus, early identification or prediction of a patient's infection using patient monitoring methods and systems described herein, alone or in combination with remote monitoring and clinical workflow as described above, may enable early intervention using appropriate treatment, and help avoid advanced patient states such as those requiring hospitalization or hemodialysis.

As described above, the remote monitoring may additionally involve an interface for a user such as medical care provider, to monitor trends in patient infection score, patient state, etc., and/or otherwise assist in managing patient treatment. For example, FIGS. 28-33 depict exemplary variations of GUIs for providing patient information and assisting in patient management.

Figure 30:
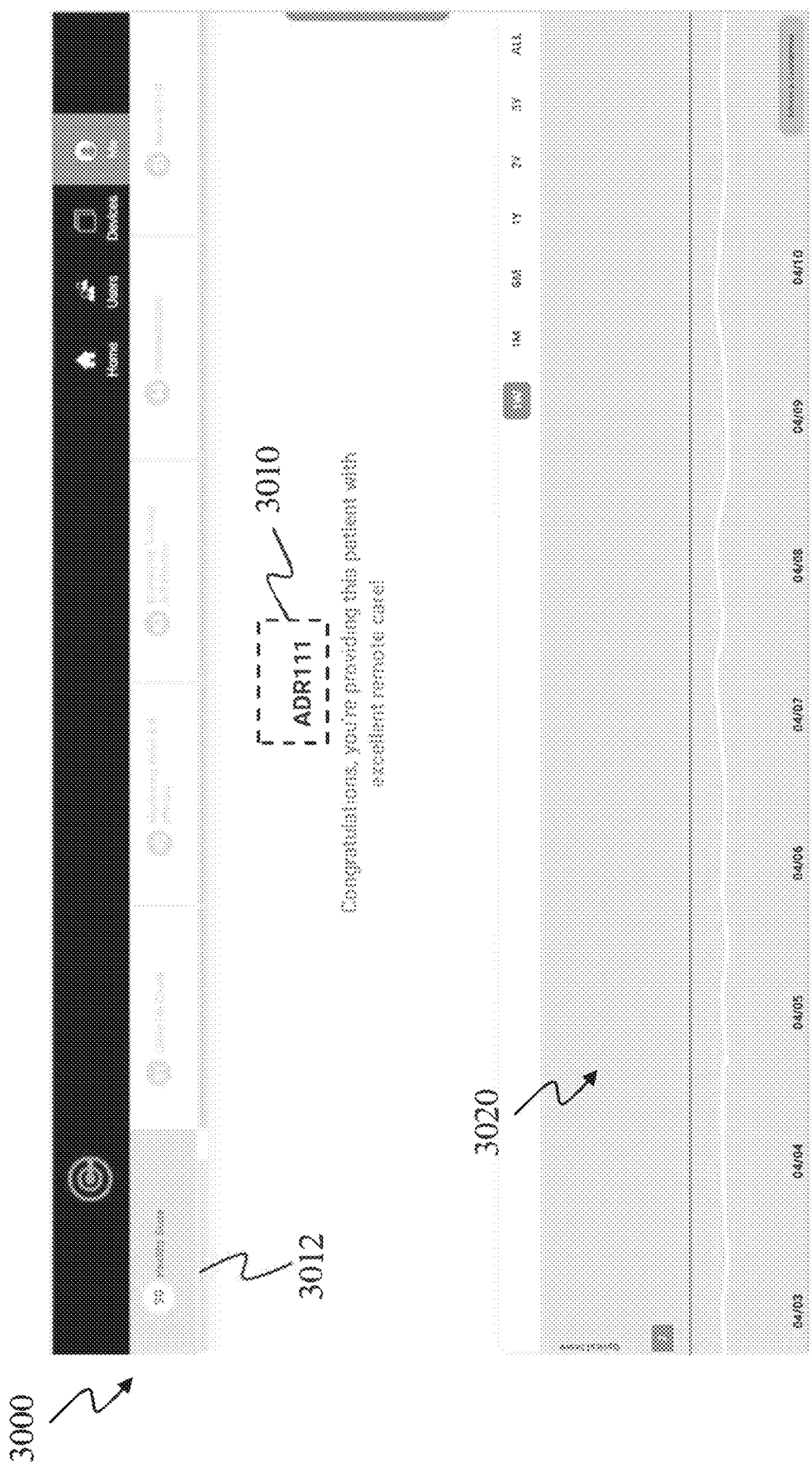
FIGS. 30-35 are exemplary graphical user interfaces (GUIs) for use in a system for patient monitoring.

FIG. 30 depicts an exemplary variation of a GUI (3000) depicting a record for a patient of interest in Stage S-0 ("HEALTHY STATE"). The record may include, for example, patient identification info (3010) such as code, name, electronic medical record, or the like associated with the patient of interest. A patient state (here, Stage S-0) may further be identified in a patient status bar (3012), and historical values of the patient's infection score may be displayed over time (3020). Overall, the patient in Stage S-0 is in a healthy state and the monitoring system is relatively passive or non-demanding from a user's point of view (e.g., care provider perspective) in that the user is not prompted or notified to perform daily monitoring or checks on the healthy patient of interest.

Figure 31:
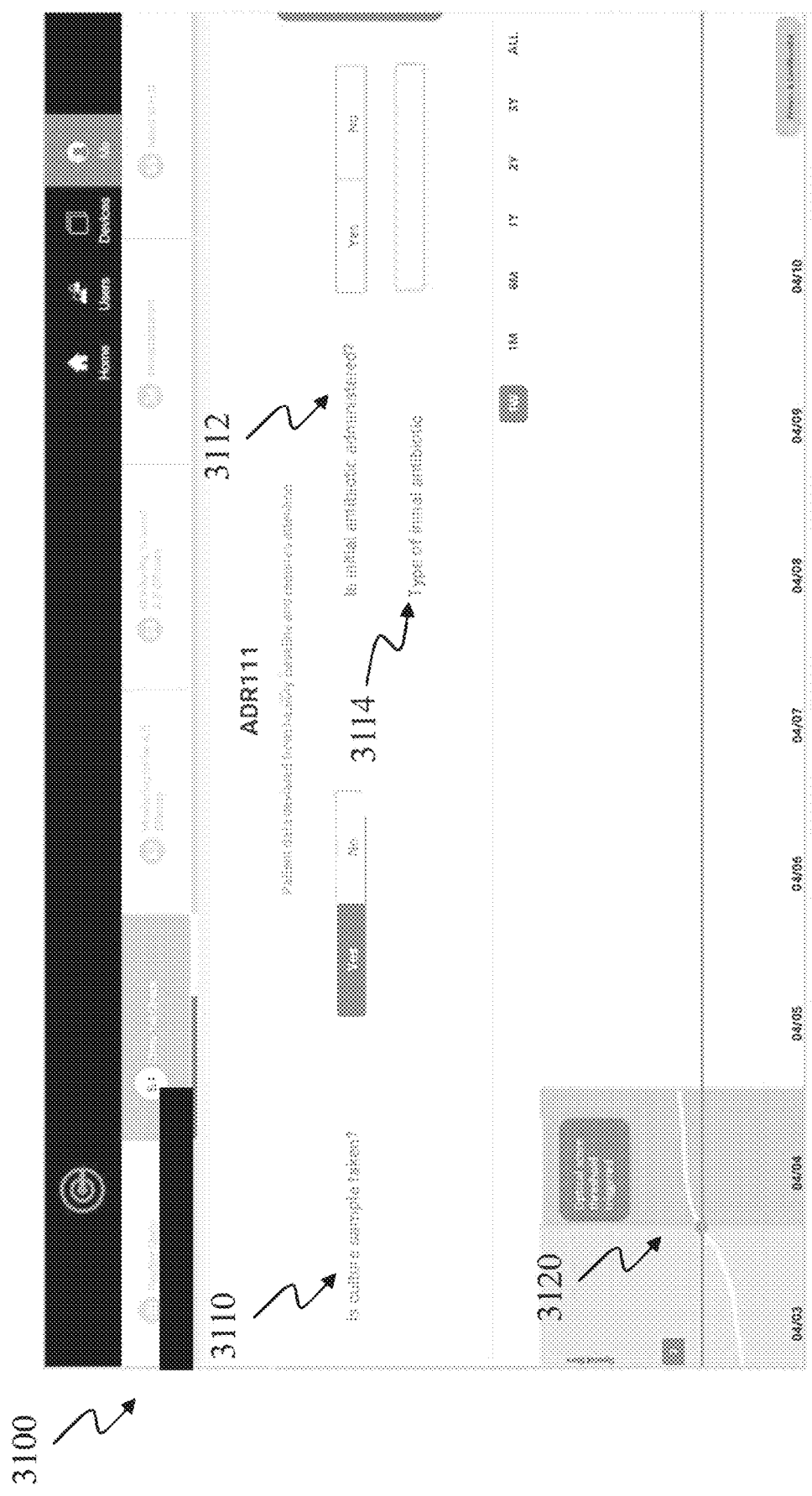

FIG. 31 depicts an exemplary variation of a GUI (3100) depicting a record for a patient of interest in Stage S-1

("CLINIC 1st CHECK"). GUI (3100) includes one or more fields configured to receive one or more user inputs (and/or pull from databases) to help manage procedural and/or administrative tasks associated with a patient during a clinic check, such as whether a culture sample has been taken (3110), whether an initial antibiotic has been administered (3112), and/or what type of initial antibiotic was administered (3114), if any. After this information has been provided and stored, the patient may be moved to Stage S-2 as described above. Furthermore, like the GUI depicted in FIG. 30, GUI (3100) may include historical values of the patient's infection score displayed over time (3120).

Figure 32A:
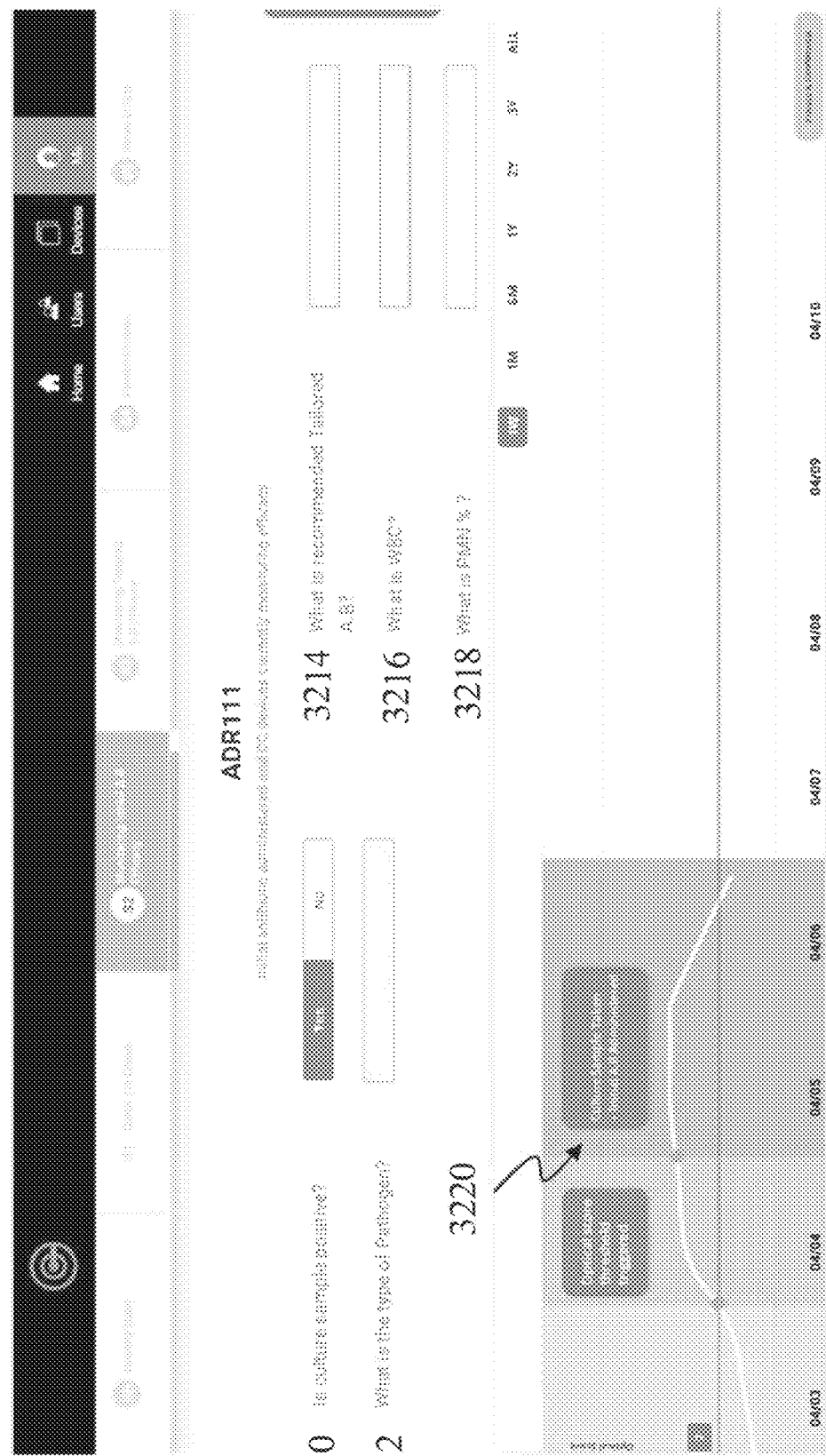
Figure 32B:
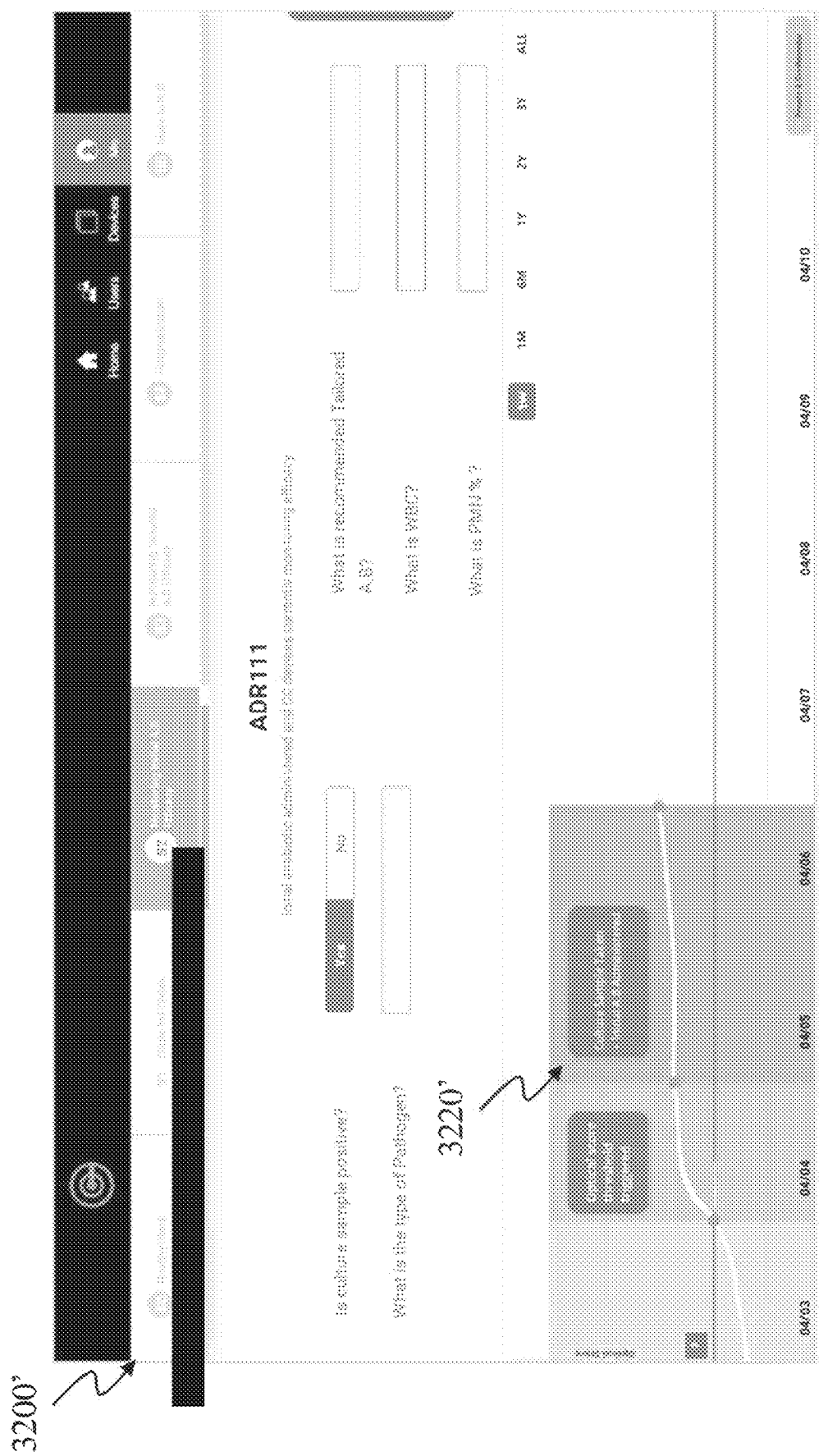

FIGS. 32A and 32B depict exemplary variations of a GUI (3200, 3200') depicting a record for a patient of interest in Stage S-2 ("MONITORING INITIAL A.B. EFFICACY"). GUI (3200) includes one or more fields configured to receive one or more user inputs to help manage patient treatment. For example, GUI (3200) may include fields to receive one or more user inputs (and/or pull from other databases) such as whether the culture sample was positive (3210), the type of pathogen was in the culture sample if so (3212), the type of recommended or prescribed specific (tailored) antibiotic (3214), white blood cell count (3216), and (PMN %) (3218). The patient may be remotely monitored using systems and methods described herein in order to assess efficacy of broad spectrum antibiotic treatment, while the patient dialyzes at home. Furthermore, GUI (3200) may include historical values of the patient's infection score displayed over time (3220). Here, GUI (3200) in FIG. 32A displays a declining trend (3220) of infection score for a patient who has responded positively to the broad spectrum antibiotic administered. GUI (3200') in FIG. 32B may be similar to GUI (3200), except that GUI (3200') depicts patient trend in infection score (3220') illustrating that the patient's infection has worsened, thereby causing the patient to move to Stage S-3.

Figure 33A:
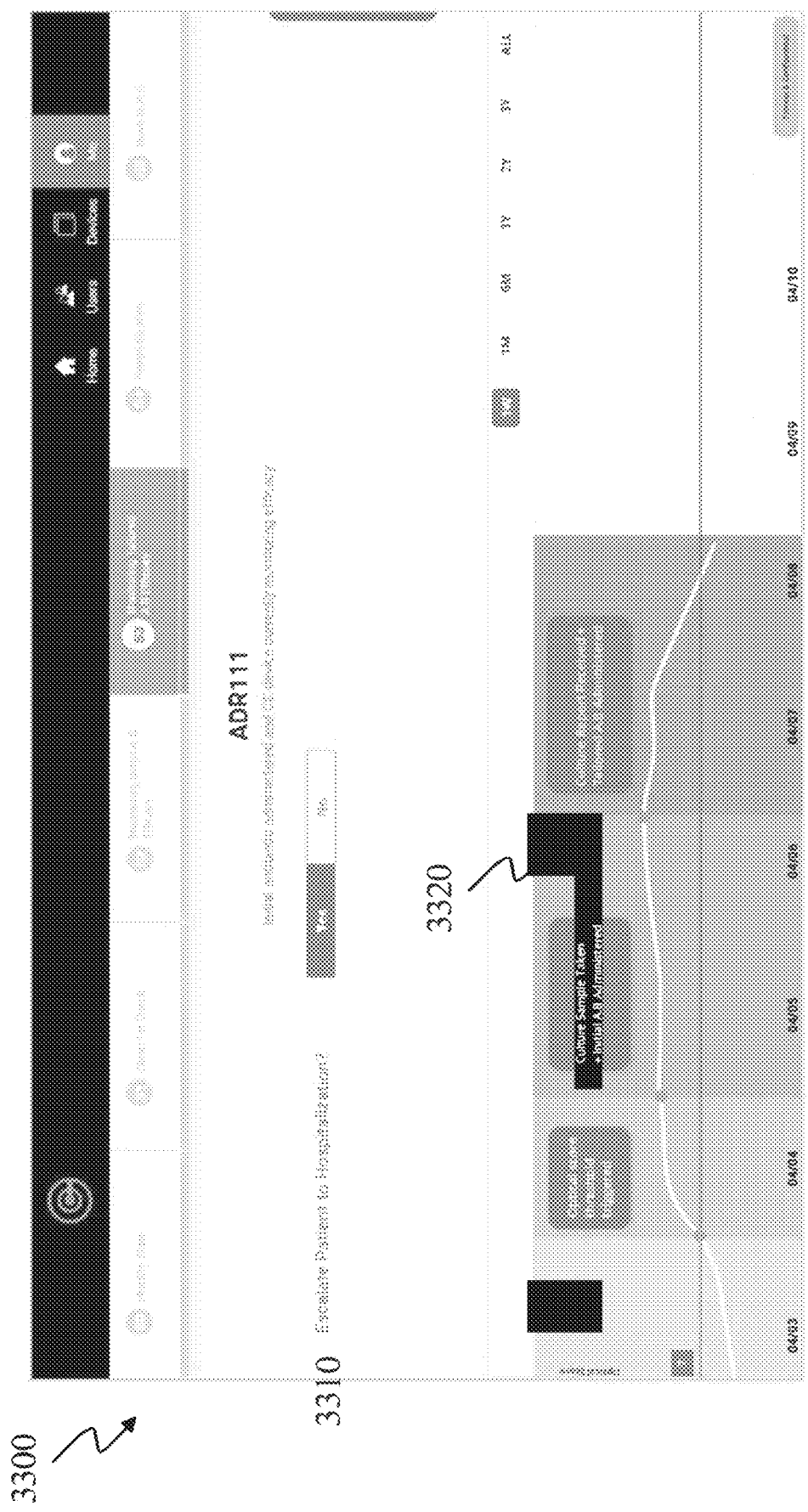
Figure 33B:
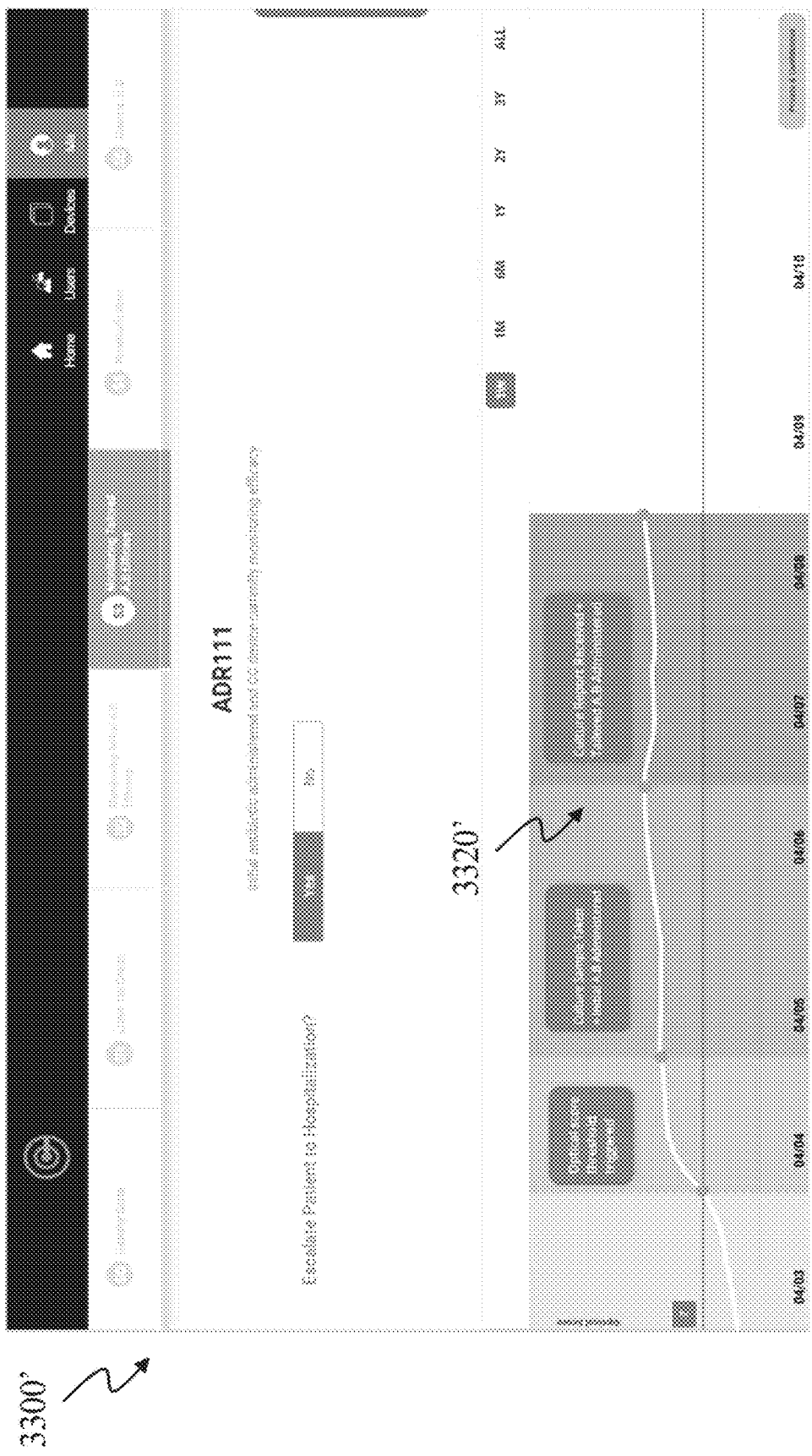

FIGS. 33A and 33B depict exemplary variations of a GUI (3300, 3300') depicting a record for a patient of interest in Stage S-3 ("MONITORING TAILORED A.B. EFFICACY"). GUI (3300) includes one or more fields configured to receive one or more user inputs to help manage patient treatment. For example, GUI (3300) may include a field to receive one or more user inputs (and/or pull from other databases) such as whether to escalate the patient to hospitalization (3310). The patient may be remotely monitored using systems and methods described herein in order to assess efficacy of specific antibiotic treatment, while the patient dialyzes at home. Furthermore, GUI (3300) displays a declining trend (3320) of infection score for a patient who has responded positively to the specific antibiotic administered. GUI (3300') may be similar to GUI (3300), except that GUI (3300') depicts patient trend in infection score (3320') illustrating that the patient's infection has worsened, thereby causing the patient to move to Stage S-4.

Figure 34:
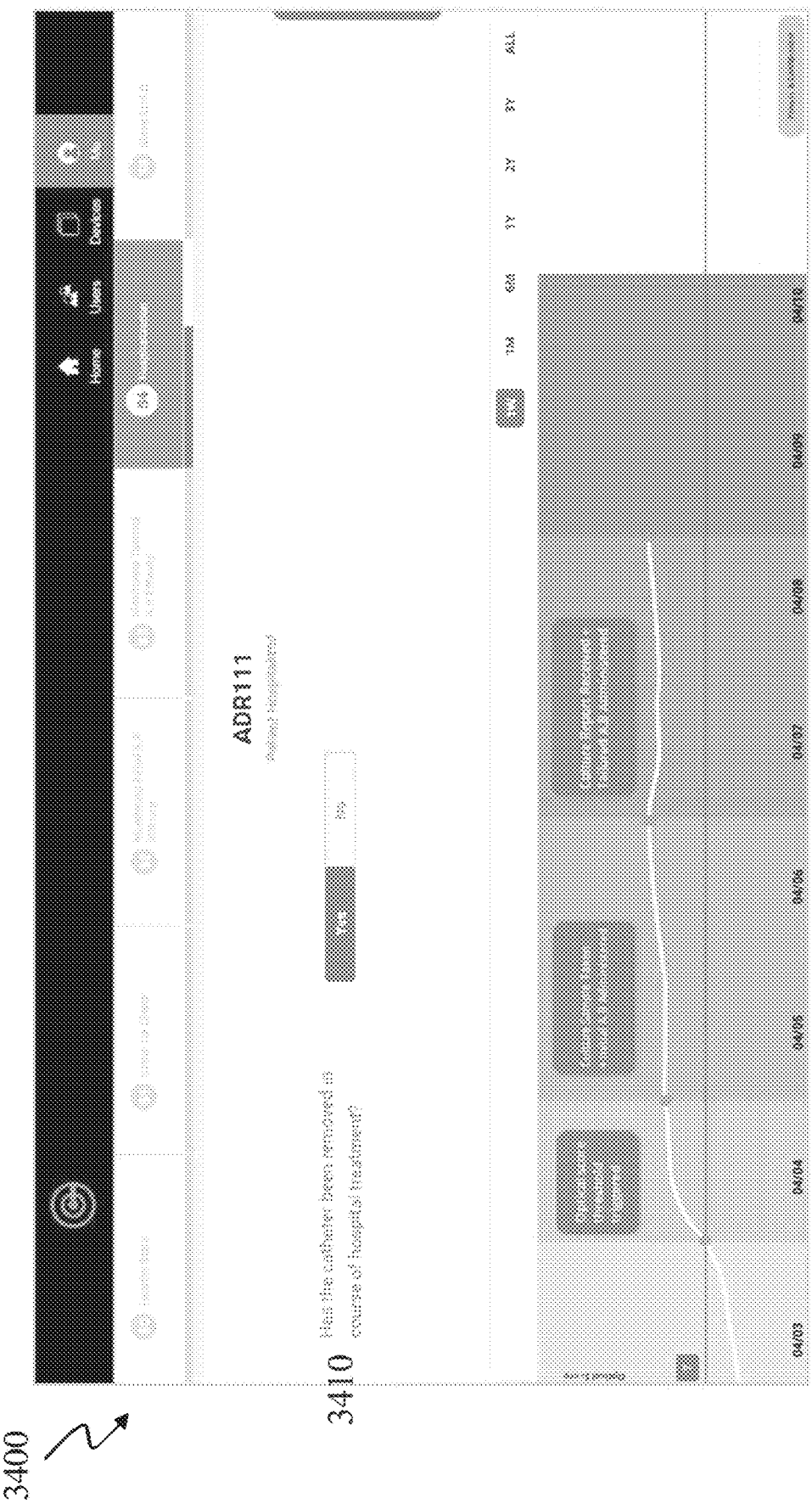

FIG. 34 depicts an exemplary variation of a GUI (3400) depicting a record for a patient of interest in Stage S-4 ("HOSPITALIZATION") receiving treatment in the hospital. Various patient characteristics and/or medical treatment details may be displayed in GUI (3400), such as a record of whether the patient's catheter has been removed in the course of hospital treatment (3410). If, upon completion of hospital treatment the input in response to this question is "No," then the patient may be moved to Stage S-0. If the input in response to this question is "Yes", then the patient may be moved to Stage S-5.

Figure 35:
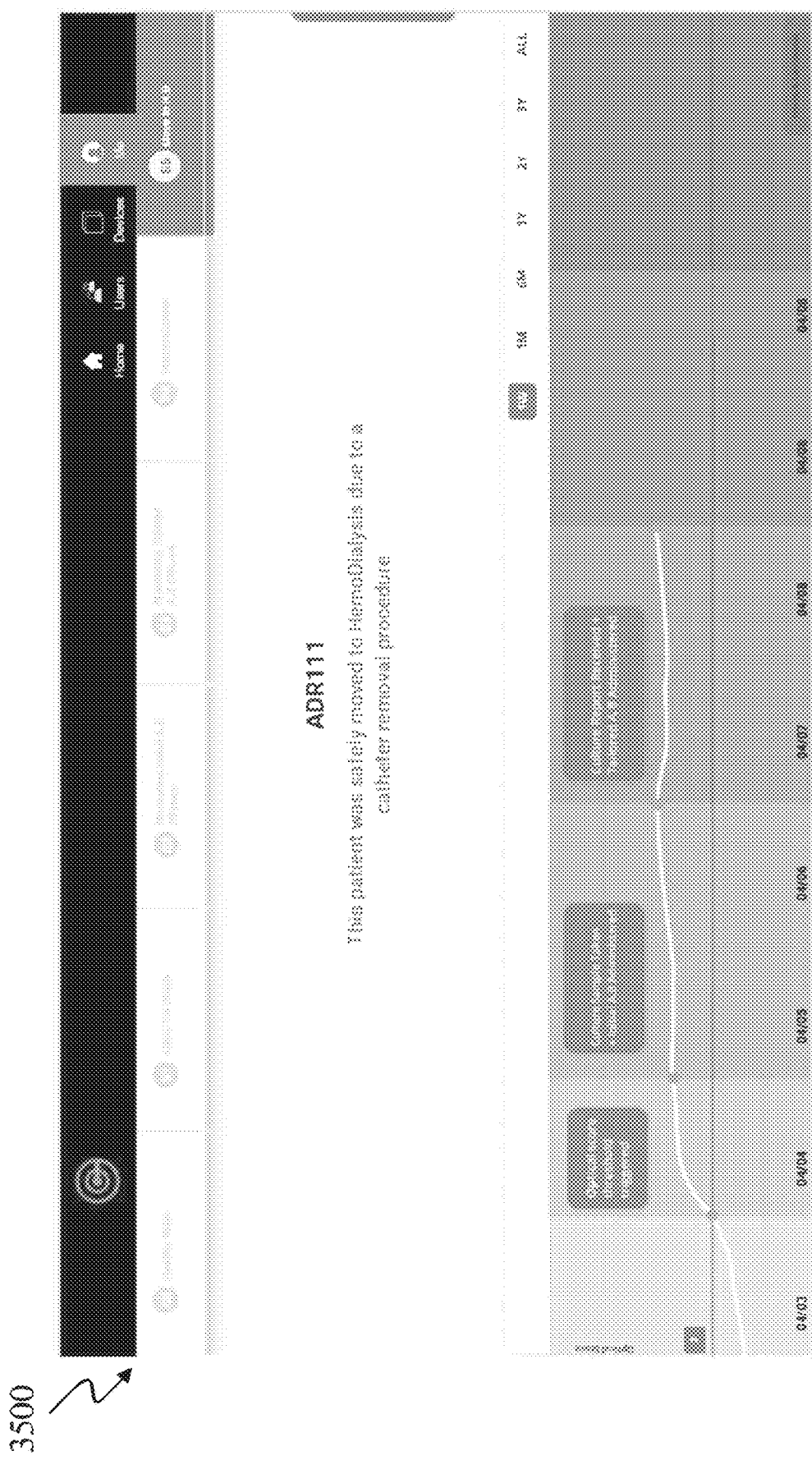

FIG. 35 depicts an exemplary variation of a GUI (3500) depicting a record for a patient of interest in Stage S-5 ("MOVED TO H.D."). In this example, the GUI (3500) indicates this disposition of this patient of interest in Stage S-5 as permanently moved to hemodialysis after having their catheter removed. In some variations, GUI (3500) may remain as a permanent record of the status of the patient of interest even though the patient of interest is no longer being remotely monitored for peritonitis. In other variations, the record for this patient of interest may be deleted after a predetermined period of time (e.g., 6 months, 1 year, 5 years, etc.) and/or as part of database cleanup and maintenance, etc.

EXEMPLARY EMBODIMENTS

Embodiment A1. A method of predicting infection of a patient, comprising:
 illuminating a patient fluid in a fluid conduit from a plurality of illumination directions;
 measuring an optical characteristic of the illuminated patient fluid using one or more sensors; and
 predicting an infection state of the patient based at least in part on the measured optical characteristic.

Embodiment A2. The method of claim A1, wherein the plurality of illumination directions comprises a first illumination direction and a second illumination direction orthogonal to the first illumination direction.

Embodiment A3. The method of claim A2, wherein the predicted infection state of the patient is based at least in part on one or more 90-degree scatter angle light intensity measurements from the one or more sensors.

Embodiment A4. The method of claim A3, wherein the predicted infection state of the patient is further based at least in part on one or more 180-degree attenuation light intensity measurements from the one or more sensors.

Embodiment A5. The method of claim A1, wherein the plurality of illumination directions comprises a first illumination direction and a second illumination direction 180 degrees offset from the first illumination direction.

Embodiment A6. The method of claim A1, wherein illuminating the patient fluid comprises illuminating the patient fluid at a first wavelength from a first illumination direction and at the first wavelength from a second illumination direction, wherein the first and second illumination directions extend along a first plane.

Embodiment A7. The method of claim A6, wherein illuminating the patient fluid comprises illuminating the patient fluid along at least the first plane and along a second plane substantially parallel to the first plane.

Embodiment A8. The method of claim A1, wherein illuminating the patient fluid comprises illuminating the patient fluid at a first wavelength between about 800 nm and about 900 nm.

Embodiment A9. The method of claim A8, wherein illuminating the patient fluid comprises illuminating the patient fluid sequentially at a plurality of wavelengths including the first wavelength.

Embodiment A10. The method of claim A9, wherein the plurality of wavelengths comprises a second wavelength between about 400 nm and about 450 nm, and a third wavelength between about 500 nm and about 550 nm Embodiment A11. The method of claim A10, wherein illuminating the patient fluid comprises sequentially illuminating the patient fluid at the third wavelength, the first wavelength, and then the second wavelength.

Embodiment A12. The method of claim A10, wherein the plurality of wavelengths comprises a fourth wavelength between about 230 nm and about 290 nm.

Embodiment A13. The method of claim A1, wherein the optical characteristic comprises one or more of optical scatter and attenuation detection angles.

Embodiment 14. The method of claim A1, wherein predicting the infection state comprises generating an infection score.

Embodiment A15. The method of claim A14, further comprising estimating turbidity of the patient fluid based at least in part on the measured optical characteristic, wherein the infection score is based at least in part on the estimated turbidity.

Embodiment A16. The method of claim A15, wherein predicting the infection state comprises predicting infection in response to the infection score exceeding a predetermined threshold during each of one or more successive measurement time periods.

Embodiment A17. The method of claim A15, wherein predicting the infection state comprises predicting infection in response to the infection score increasing from a patient baseline over time.

Embodiment A18. The method of claim A15, wherein predicting the infection state comprises predicting infection based on a rate of change of the infection score over time.

Embodiment A19. The method of claim A15, wherein predicting the infection state comprises predicting infection in response to any one or more of the following: the infection score exceeding a predetermined threshold during each of one or more successive measurement time periods, the infection score increasing from a patient baseline over time, and the infection score having an increasing rate of change over time.

Embodiment A20. The method of claim A1, wherein predicting the infection state comprises predicting a probability of infection.

Embodiment A21. The method of claim A1, wherein the fluid conduit is coupled to a peritoneal dialysis device fluid path.

Embodiment A22. The method of claim A1, wherein the fluid conduit is coupled to a peritoneal dialysis device tubing set.

Embodiment A23. The method of claim A1, wherein the fluid conduit is coupled to an inlet of the peritoneal dialysis device tubing set.

Embodiment A24. The method of claim A1, wherein the fluid conduit is coupled to an outlet of the peritoneal dialysis device tubing set.

Embodiment A25. The method of claim A1, wherein the fluid conduit is coupled to a drain line of a peritoneal dialysis cycler tubing set.

Embodiment A26. The method of claim A1, wherein the fluid conduit is coupled to a drain line extension configured to couple to a peritoneal dialysis cycler tubing set drain line.

Embodiment A27. The method of claim A1, wherein the fluid conduit is coupled to a patient line of a peritoneal dialysis cycler tubing set.

Embodiment A28. The method of claim A1, further comprising estimating a fluid flow rate in the fluid conduit based at least in part on the measured optical characteristic, wherein illuminating the patient fluid comprises activating illumination based on the estimated fluid flow rate.

Embodiment A29. The method of claim A28, further comprising determining a fluid flow state comprising detecting at least one of an ON state and an OFF state based on the estimated fluid flow rate, wherein illuminating the patient fluid comprises activating illumination in response to detecting the ON state and ceasing illumination in response to detecting the OFF state.

Embodiment A30. The method of claim A28, further comprising identifying a false positive fluid flow state based on the estimated fluid flow rate.

Embodiment A31. The method of claim A29, wherein identifying the false positive fluid flow state comprises detecting a predetermined number of pulses during less than each of two or more successive measurement time periods.

Embodiment A32. The method of claim A29, wherein detecting the ON state comprises detecting a predetermined number of pulses during each of two or more successive measurement time periods.

Embodiment A33. The method of claim A32, wherein the two or more successive measurement time periods are separated by a predetermined delay time period.

Embodiment A34. The method of claim A29, wherein estimating the fluid flow rate is based at least in part on applying one or more of a low pass filter and a high pass filter to the measured optical characteristic.

Embodiment A35. The method of claim A1, further comprising initiating illuminating the patient fluid and measuring the optical characteristic based on a user input.

Embodiment A36. The method of claim A1, further comprising detecting a bubble in the fluid conduit based at least in part on the optical measurement.

Embodiment A37. The method of claim A1, further comprising providing an indication of the predicted infection state to a user.

Embodiment A38. The method of claim A1, further comprising predicting a particle concentration of the patient fluid based at least in part on the measured optical characteristic.

Embodiment A39. The method of claim A1, further comprising predicting bleeding of the patient based at least in part on the measured optical characteristic.

Embodiment A40. The method of claim A1, further comprising predicting an immune response of the patient based at least in part on the measured optical characteristic.

Embodiment A41. The method of claim A1, further comprising predicting infection onset for ascites drainage patients based at least in part on the measured optical characteristic.

Embodiment A42. The method of claim A1, further comprising predicting a fibrin content of the patient fluid based at least in part on the measured optical characteristic.

Embodiment B1. A vessel for use in a fluid conduit, comprising:
 an inlet portion;
 an outlet portion; and
 an optically transparent measurement portion between the inlet portion and the outlet portion, wherein the measurement portion comprises at least two substantially planar surfaces, a rotational alignment feature, and a depth alignment feature.

Embodiment B2. The vessel of claim B1, wherein the measurement portion comprises an internal volume configured to receive fluid, wherein the internal volume comprises radiused corners.

Embodiment B3. The vessel of claim B1, wherein the at least two substantially planar surfaces comprise a first planar surface generally orthogonal to a second planar surface.

Embodiment B4. The vessel of claim B1, wherein the at least two substantially planar surfaces comprise a first planar surface opposite to a second planar surface.

Embodiment B5. The vessel of claim B4, wherein the measurement portion comprises a generally square cross-section.

Embodiment B6. The vessel of claim B1, wherein at least a portion of the measurement portion is tapered.

Embodiment B7. The vessel of claim B1, wherein the measurement portion comprises one or more of copolyester, acrylonitrile butadiene styrene, polycarbonate, acrylic, cyclic olefin copolymer, cyclic olefin polymer, polyester, polystyrene, ultem, polyethylene glycol-coated silicone, zwitterionic coated polyurethane, polyethylene oxide-coated polyvinyl chloride, and polyamphiphilic silicone.

Embodiment B8. The vessel of claim B1, further comprising an opaque connector coupleable to the inlet portion or the outlet portion.

Embodiment B9. The vessel of claim B8, wherein at least one of the inlet portion and the outlet portion is coupleable to the fluid conduit.

Embodiment B10. The vessel of claim B9, further comprising one or more of a vent cap, clamp, and connector coupled to the fluid conduit.

Embodiment B11. The vessel of claim B9, wherein the vessel is coupled to a peritoneal dialysis drain set extension tubing.

Embodiment B12. The vessel of claim B9, wherein the vessel is coupled to a peritoneal dialysis cycler tubing cassette.

Embodiment B13. The vessel of claim B9, wherein the vessel is coupled to an inlet of a peritoneal dialysis cycler tubing cassette.

Embodiment B14. The vessel of claim B9, wherein the vessel is coupled to a peritoneal dialysis drain bag connector.

Embodiment B15. The vessel of claim B9, wherein the vessel is coupled to a proximal end of a peritoneal dialysis drain bag connector.

Embodiment B16. The vessel of claim B9, wherein the vessel is coupled to a urinary catheter or Foley catheter drain bag.

Embodiment B17. The vessel of claim B9, wherein the vessel is coupled to a central venous drain line.

Embodiment B18. The vessel of claim B9, wherein the vessel is coupled to a hemodialysis blood circulation tube set.

Embodiment B19. The vessel of claim B9, wherein the vessel is coupled to an in-dwelling catheter.

Embodiment B20. The vessel of claim B9, wherein the vessel is coupled to a proximal end of the in-dwelling catheter Embodiment C1. A patient monitoring device, comprising:
a housing comprising:
a holder configured to releasably receive a portion of a fluid conduit;
at least one illumination source configured to illuminate the received portion of the fluid conduit; and
at least one optical sensor configured to generate a signal, wherein the holder comprise one or more engagement features configured to orient the received portion of the fluid conduit in a predetermined rotational and vertical orientation relative to the at least one illumination source and the at least one optical sensor.

Embodiment C2. The device of claim C1, wherein the housing comprises alight seal.

Embodiment C3. The device of claim C1, wherein the one or more engagement features is configured to orient the received portion of the fluid conduit by mating with an alignment feature of the received portion of the fluid conduit.

Embodiment C4. The device of claim C1, wherein the one or more engagement features comprises an open slot.

Embodiment C5. The device of claim C1, wherein the at least one illumination source comprises a plurality of illumination sources.

Embodiment C6. The device of claim C5, wherein the illumination sources are configured to illuminate in a first illumination direction and a second illumination direction orthogonal to the first illumination direction.

Embodiment C7. The device of claim C5, wherein at least two of the illumination sources are configured to illuminate along a first plane at a first wavelength.

Embodiment C8. The device of claim C5, wherein at least another two of the illumination sources are configured to illuminate along a second plane substantially parallel to the first plane.

Embodiment C9. The device of claim C5, wherein the illumination sources are configured to illuminate in a first illumination direction and a second illumination direction opposite the first direction.

Embodiment C10. The device of claim C1, wherein the illumination sources are configured to illuminate in a first illumination direction and a second illumination direction 180 degrees offset from the first direction.

Embodiment C11. The device of claim C1, wherein the illumination sources comprise a first illumination source configured to emit light at a first wavelength between about 800 nm and about 900 nm.

Embodiment C12. The device of claim C1, wherein the illumination sources comprise a second illumination source configured to emit light at a second wavelength between about 400 nm and about 450 nm.

Embodiment C13. The device of claim C1, wherein the illumination sources comprise a third illumination source configured to emit light at a third wavelength between about 500 nm and about 550 nm.

Embodiment C14. The device of claim C1, wherein the illumination sources comprise a fourth illumination source configured to emit light at a third wavelength between about 230 nm and about 290 nm.

Embodiment C15. The device of claim C1, wherein the at least one optical sensor comprises a plurality of optical sensors.

Embodiment C16. The device of claim C1, wherein one or more of the at least one illumination source and the at least one optical sensor comprises an anti-reflective coating.

Embodiment C17. The device of claim C1, wherein the holder defines a longitudinal axis, and wherein the at least one optical sensor comprises a plurality of optical sensors spaced apart parallel to the longitudinal axis.

Embodiment C18. The device of claim C1, further comprising a controller configured to generate patient data based at least in part on the signal.

Embodiment C19. The device of claim C1, wherein the patient data comprises an infection state.

Embodiment C20. The device of claim C1, further comprising a display.

Embodiment C21. The device of claim C1, further comprising abase, wherein the housing is offset and spaced apart from the base.

Embodiment C22. The device of claim C1, wherein the housing comprises a peritoneal dialysis cycler.

Embodiment C23. The device of claim C1, wherein the housing comprises a hemodialysis device.

Embodiment C24. The device of claim C1, wherein the housing is configured to couple to one or more of a patient platform and medical cart.

Embodiment C25. The device of claim C1, wherein the housing comprises a peritoneal dialysis device fluid path.

Embodiment C26. The device of claim C1, wherein the fluid conduit is coupled to a peritoneal dialysis tubing set.

Embodiment C27. The device of claim C1, wherein the fluid conduit is coupled to a peritoneal dialysis cycler tubing set.

Embodiment C28. The device of claim C1, wherein the fluid conduit is coupled to a peritoneal dialysis drain bag connector.

Embodiment C29. The device of claim C1, wherein the fluid conduit comprises:
 an inlet portion;
 an outlet portion; and
 an optically transparent measurement portion between the inlet portion and the outlet portion, wherein the measurement portion comprises at least two substantially planar surfaces, a rotational alignment feature, and a depth alignment feature.

Embodiment C30. The device of claim C29, wherein at least one of the rotational alignment feature and the depth alignment feature is configured to mate with the one or more engagement features of the holder.

Embodiment C31. The device of claim C1, further comprising a controller configured to generate patient data based at least in part on the signal.

Embodiment C32. The device of claim C1, wherein the controller is located remote from the housing, and wherein the device further comprises a communication device configured to transmit data representative of the signal to the controller.

Embodiment C33. The device of claim C32, wherein the controller is configured to predict an infection score of a patient based at least in part on the signal.

Embodiment C34. The device of claim C32, wherein the controller is configured to predict an infection state of a patient in response to any one or more of the following: the infection score exceeding a predetermined threshold during each of one or more successive measurement time periods, the infection score increasing from a patient baseline over time, and the infection score having an increasing rate of change over time.

Embodiment C35. The device of claim C34, wherein the infection state comprises a probability of infection.

Embodiment C36. The device of claim C32, wherein the fluid conduit is configured to receive a patient fluid and the controller is configured to estimate turbidity of the patient fluid based at least in part on the signal, wherein the infection score is based at least in part on the estimated turbidity.

Embodiment C37. The device of claim C32, wherein the controller is configured to monitor a trend in infection score predicting infection resolution of the patient.

Embodiment C38. The device of claim C32, wherein the controller is configured to monitor a trend in infection score predicting infection resolution of the patient by predicting infection resolution in response to any one or more of the following: the infection score falling below a predetermined threshold during each of one or more successive measurement time periods, the infection score decreasing from a patient baseline over time, and the infection score having a decreasing rate of change over time.

Embodiment D1. A method for remote monitoring of a patient, comprising:
 at one or more processors:
  receiving an optical characteristic measurement of a patient fluid associated with the patient over a remote communication link;
  determining an infection score predicting infection of the patient, wherein the infection score is based at least in part on the received optical characteristic measurement; and
  associating the patient as one of a plurality of patient infection states based at least in part on the determined infection score.

Embodiment D2. The method of claim D1, further comprising notifying a user of the associated patient infection state.

Embodiment D3. The method of claim D1, further comprising prompting a user to perform one or more predetermined patient treatment actions based on the associated patient infection state.

Embodiment D4. The method of claim D3, wherein the one or more predetermined patient treatment actions comprises administering a broad spectrum antimicrobial to the patient.

Embodiment D5. The method of claim D3, wherein the one or more predetermined patient treatment actions comprises administering a pathogen-specific antimicrobial to the patient.

Embodiment D6. The method of claim D3, wherein the one or more predetermined patient treatment actions comprises remotely monitoring a trend in infection score predicting infection resolution of the patient.

Embodiment D7. The method of claim D3, wherein remotely monitoring the trend in infection score predicting infection resolution comprises predicting infection resolution in response to the infection score decreasing from a patient baseline over time.

Embodiment D8. The method of claim D7, wherein remotely monitoring the trend in infection score predicting infection resolution comprises predicting infection resolution based on a rate of change of the infection score over time.

Embodiment D9. The method of claim D7, wherein remotely monitoring the trend in infection score predicting infection resolution comprises predicting infection resolution in response to any one or more of the following: the infection score falling below a predetermined threshold during each of one or more successive measurement time periods, the infection score decreasing from a patient baseline over time, and the infection score having a decreasing rate of change over time.

Embodiment D10. The method of claim D1, wherein the plurality of patient infection states comprises a first patient infection state corresponding to a healthy patient.

Embodiment D11. The method of claim D1, wherein the plurality of patient infection states comprises a second patient infection state corresponding to a patient brought to a medical care provider.

Embodiment D12. The method of claim D1, wherein the plurality of patient infection states comprises a third patient infection state corresponding to a patient who has received a broad spectrum antibiotic treatment.

Embodiment D13. The method of claim D1, wherein the plurality of patient infection states comprises a third patient infection state corresponding to a patient who has received a pathogen-specific antimicrobial treatment.

Embodiment D14. The method of claim D1, wherein the plurality of patient infection states comprises a fourth patient infection state corresponding to a patient who has been hospitalized.

Embodiment D15. The method of claim D1, wherein the plurality of patient infection states comprises a fifth patient infection state corresponding to a patient who has been transitioned to hemodialysis.

Embodiment D16. The method of claim D1, wherein the predicted infection is peritonitis.

The foregoing description, for purposes of explanation, used specific nomenclature to provide a thorough understanding of the invention. However, it will be apparent to one skilled in the art that specific details are not required in order to practice the invention. Thus, the foregoing descriptions of specific variations of the invention are presented for purposes of illustration and description. They are not intended to be exhaustive or to limit the invention to the precise forms disclosed; obviously, many modifications and variations are possible in view of the above teachings. The variations were chosen and described in order to best explain the principles of the invention and its practical applications, and they thereby enable others skilled in the art to best utilize the invention and various implementations with various modifications as are suited to the particular use contemplated. It is intended that the following claims and their equivalents define the scope of the invention.

We claim:

1. A vessel for use with a fluid conduit, comprising:
   an inlet portion;
   an outlet portion; and
   an optically transparent measurement portion between the inlet portion and the outlet portion, wherein at least a portion of the measurement portion is tapered, and wherein the measurement portion comprises at least two substantially planar surfaces and a depth alignment feature.

2. The vessel of claim 1, wherein the measurement portion comprises an internal volume configured to receive fluid, wherein the internal volume comprises radiused internal orthogonal corners.

3. The vessel of claim 1, wherein the at least two substantially planar surfaces comprise a first planar surface generally orthogonal to a second planar surface.

4. The vessel of claim 1, wherein the at least two substantially planar surfaces comprise a first planar surface opposite to a second planar surface.

5. The vessel of claim 4, wherein the measurement portion comprises a generally square cross-section.

6. The vessel of claim 1, wherein the measurement portion is tapered along the entire measurement portion between the inlet portion and the outlet portion.

7. The vessel of claim 1, wherein the measurement portion comprises one or more materials configured for light transmission at a wavelength between about 230 nm and about 900 nm.

8. The vessel of claim 1, wherein one or more of the inlet portion and the outlet portion comprises an ambient light reduction feature.

9. The vessel of claim 1, further comprising an opaque connector coupled to the inlet portion or the outlet portion.

10. The vessel of claim 9, wherein the opaque connector comprises a textured grip configured for a patient to handle the vessel.

11. The vessel of claim 9, wherein the opaque connector couples the measurement portion comprising a square cross-section to a fluid conduit comprising a circular cross-section.

12. The vessel of claim 9, wherein the opaque connector is configured to provide strain relief to the fluid conduit.

13. The vessel of claim 9, wherein the measurement portion and the opaque connector are solvent bonded.

14. The vessel of claim 1, wherein the measurement portion comprises a rotational alignment feature.

15. The vessel of claim 14, wherein the rotational alignment feature is arranged over a corner of the measurement portion.

16. The vessel of claim 14, wherein one or more of the rotational alignment feature and the depth alignment feature comprises a protrusion.

17. The vessel of claim 1, wherein at least a portion of the rotational alignment feature is tapered.

18. The vessel of claim 1, wherein the depth alignment feature is disposed around at least a portion of the perimeter of the vessel.

19. The vessel of claim 1, wherein the fluid conduit comprises one or more of a vent cap, clamp, and connector.

20. The vessel of claim 1, wherein the vessel is coupled to a peritoneal dialysis drain set extension tubing.

21. The vessel of claim 1, wherein the vessel is coupled to a peritoneal dialysis cycler tubing cassette.

22. The vessel of claim 1, wherein the vessel is coupled to a continuous ambulatory peritoneal dialysis system.

23. The vessel of claim 1, wherein the vessel is coupled to a peritoneal dialysis drain bag.

24. The vessel of claim 1, wherein the vessel is coupled to a proximal end of an in-dwelling catheter.

25. The vessel of claim 1, wherein the vessel is coupled to one or more of an in-dwelling catheter, a urinary catheter, a urine collection bag, a central venous drain line, and a hemodialysis blood circulation tube set.

26. The vessel of claim 1, wherein a cross-section of the measurement portion is larger than a cross-section of the inlet portion.

27. The vessel of claim 1, wherein the taper of the measurement portion comprises a draft angle of between about 0.5 degrees and about 2 degrees.

* * * * *